United States Patent
Roemmele

(10) Patent No.: US 8,541,590 B2
(45) Date of Patent: Sep. 24, 2013

(54) PROTEASOME INHIBITORS AND PROCESSES FOR THEIR PREPARATION, PURIFICATION AND USE

(75) Inventor: Renee Caroline Roemmele, Maple Glen, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 13/528,147

(22) Filed: Jun. 20, 2012

(65) Prior Publication Data

US 2012/0270840 A1    Oct. 25, 2012

Related U.S. Application Data

(63) Continuation of application No. PCT/US2010/061695, filed on Dec. 22, 2010.

(60) Provisional application No. 61/288,957, filed on Dec. 22, 2009.

(51) Int. Cl.
*A61K 31/44* (2006.01)
*C07D 213/46* (2006.01)

(52) U.S. Cl.
USPC .......................................... 546/314; 514/354

(58) Field of Classification Search
None
See application file for complete search history.

(56) References Cited

U.S. PATENT DOCUMENTS

| | | |
|---|---|---|
| 4,499,082 A | 2/1985 | Shenvi et al. |
| 4,537,773 A | 8/1985 | Shenvi |
| 4,963,655 A | 10/1990 | Kinder et al. |
| 5,023,236 A | 6/1991 | Edgington et al. |
| 5,106,948 A | 4/1992 | Kinder et al. |
| 5,159,060 A | 10/1992 | Kinder et al. |
| 5,169,841 A | 12/1992 | Kleeman et al. |
| 5,187,157 A | 2/1993 | Kettner et al. |
| 5,242,904 A | 9/1993 | Kettner et al. |
| 5,250,720 A | 10/1993 | Kettner et al. |
| 5,470,864 A | 11/1995 | Duflos et al. |
| 5,550,262 A | 8/1996 | Iqbal et al. |
| 5,580,486 A | 12/1996 | Labeque et al. |
| 5,585,390 A | 12/1996 | Duflos et al. |
| 5,614,649 A | 3/1997 | Iqbal et al. |
| 5,658,885 A | 8/1997 | Lee et al. |
| 5,693,617 A | 12/1997 | Stein et al. |
| 5,780,454 A | 7/1998 | Adams et al. |
| 5,830,870 A | 11/1998 | Iqbal et al. |
| 5,834,487 A | 11/1998 | Lum et al. |
| 5,990,083 A | 11/1999 | Iqbal et al. |
| 6,066,730 A | 5/2000 | Adams et al. |
| 6,075,150 A | 6/2000 | Wang et al. |
| 6,083,903 A | 7/2000 | Adams et al. |
| 6,096,778 A | 8/2000 | Chatterjee et al. |
| 6,297,217 B1 | 10/2001 | Adams et al. |
| 6,310,057 B1 | 10/2001 | Chatterjee et al. |
| 6,372,883 B1 | 4/2002 | Attwood et al. |
| 6,465,433 B1 | 10/2002 | Adams et al. |
| 6,548,668 B2 | 4/2003 | Adams et al. |
| 7,223,745 B2 | 5/2007 | Chatterjee et al. |
| 7,442,830 B1 | 10/2008 | Olhava et al. |
| 7,468,383 B2 | 12/2008 | Bernardini et al. |
| 7,576,206 B2 | 8/2009 | Bernardini et al. |
| 7,915,236 B2 | 3/2011 | Bernardini et al. |
| 8,058,262 B2 | 11/2011 | Bernardini et al. |
| 8,283,367 B2 | 10/2012 | Bernardini et al. |
| 2001/0012354 A1 | 8/2001 | Siman et al. |
| 2002/0173488 A1 | 11/2002 | Adams et al. |
| 2002/0188100 A1 | 12/2002 | Plamondon et al. |
| 2003/0008828 A1 | 1/2003 | Priestley et al. |
| 2005/0101781 A1 | 5/2005 | Agoulnik et al. |
| 2005/0107307 A1 | 5/2005 | Bernadini et al. |
| 2005/0240047 A1 | 10/2005 | Pickersgill et al. |
| 2012/0041196 A1 | 2/2012 | Bernardini et al. |

FOREIGN PATENT DOCUMENTS

| | | |
|---|---|---|
| DE | 199 14 474 A1 | 10/1999 |
| EP | 293881 | 12/1988 |
| EP | 315574 | 5/1989 |
| EP | 354522 | 2/1990 |
| EP | 632026 | 6/1994 |
| EP | 0 995 757 | 4/2000 |
| EP | 01166781 | 2/2002 |
| WO | WO 89/09225 | 10/1989 |
| WO | WO 91/13904 | 9/1991 |

(Continued)

OTHER PUBLICATIONS

Adams et al., "Potent and Selective Inhibitors of the Proteasome: Dipeptidyl Boronic Acids," *Bioorganic & Medicinal Chemistry Letters*, 1998, vol. 8, Issue 4, pp. 333-338.
Aoyagi et al., "Structures and activities of protease inhibitors of microbial origin," *Proteases and Biological Control*, 1975, pp. 429-454.
Attwood et al., "The Design and Synthesis of Potent Inhibitors of Hepatitis C Virus NS3-4A Proteinase," *Antiviral Chemistry & Chemotherapy*, 1999, vol. 10, Issue 5, pp. 259-273.
Christie et al., Alzheimer's Disease: Correlation of the Suppression of β-Amyloid Peptide Secretion From Cultured Cells with Inhibition of the Chymotrypsin-Like Activity of the Proteasome, *J. of Neurochemistry*, 1999, vol. 73, Issue 1, pp. 195-204.
Dick at al., "Degradation of oxidized insulin B chain by the multiproteinase complex macropain (proteasome)," *Biochemistry*, Mar. 12, 1991;30(10):2725-34.
Dudson et al., "Solid Phase Synthesis of Aminoboronic Acids: Potent Inhibitors of the Hepatitis C Virus NS3 Proteinase," *Biorganic & Medicinal Chemistry Letters*, 2000, vol. 10, No. 14, pp. 1577-1579.
Evrard-Todeschi et al., "Conformations in Solution and Bound to Bacterial Ribonsomes of Ketolides, HMR 3647 (Telithromycin) and RU72366: A New Class of Highly Potent Antibacterials," *Bioorg. Med. Chem.* Jul. 2000;8(7):1579-97.
Fenteany at al., "Inhibition of proteasome activities an subunit-specific amino-terminal threonine modification by lactacystin," *Science*, May 5, 1995;268(5211):726-31.

(Continued)

*Primary Examiner* — Janet Andres
*Assistant Examiner* — Heidi Reese

(57) ABSTRACT

The invention provides boronic esters of Formula I

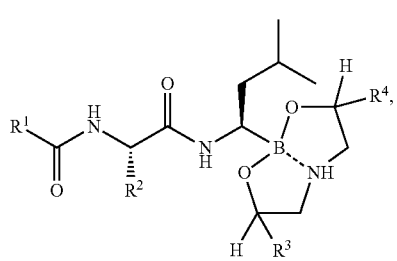

wherein $R^1$, $R^2$, $R^3$, and $R^4$ are as described herein, and methods for the preparation and purification thereof.

15 Claims, 4 Drawing Sheets

(56) References Cited

FOREIGN PATENT DOCUMENTS

| WO | WO 94/04653 | 3/1994 |
|---|---|---|
| WO | WO 94/17816 | 8/1994 |
| WO | WO 94/25049 | 11/1994 |
| WO | WO 94/25051 | 11/1994 |
| WO | WO 95/09634 | 4/1995 |
| WO | WO 95/09838 | 4/1995 |
| WO | WO 95/20603 | 8/1995 |
| WO | WO 95/25533 | 9/1995 |
| WO | WO 96/11697 | 4/1996 |
| WO | WO 96/12499 | 5/1996 |
| WO | WO 96/13266 | 5/1996 |
| WO | WO96/14857 | 5/1996 |
| WO | WO 96/14857 | 5/1996 |
| WO | WO 98/17679 | 4/1998 |
| WO | WO 98/22496 | 5/1998 |
| WO | WO 99/30707 | 6/1999 |
| WO | WO99/30707 | 6/1999 |
| WO | WO 00/02548 | 1/2000 |
| WO | WO 00/23614 | 4/2000 |
| WO | WO 00/64467 | 11/2000 |
| WO | WO 00/64863 | 11/2000 |
| WO | WO 00/66557 | 11/2000 |
| WO | WO 01/02424 | 1/2001 |
| WO | WO 01/20995 | 3/2001 |
| WO | WO 01/28579 | 4/2001 |
| WO | WO 02/08187 | 1/2002 |
| WO | WO 02/030455 | 4/2002 |
| WO | WO 02/059130 | 8/2002 |
| WO | WO 02/059131 | 8/2002 |
| WO | WO 02/082091 | 10/2002 |
| WO | WO 02/094857 | 11/2002 |
| WO | WO 02/096933 | 12/2002 |
| WO | WO 03/015706 | 2/2003 |
| WO | WO03/033507 | 4/2003 |
| WO | WO03/059898 | 7/2003 |
| WO | WO 03/059898 | 7/2003 |
| WO | WO2005/016859 | 2/2005 |
| WO | WO2005/021558 | 3/2005 |
| WO | WO2009/020448 | 2/2009 |
| WO | WO2010/114982 | 10/2010 |
| WO | WO 2010114982 A2 * | 10/2010 |

OTHER PUBLICATIONS

Fenteany et al., "A beta-lactone related to lactacystin induces neurite outgrowth in a neuroblastoma cell line and inhibits cell cycle progression in an osteosarcoma cell line" Proc Natl Aced Sci, Apr. 12, 1994;91(8):3358-62.

Garcia et al., "A new structural class of selective and non-covalent inhibitors of the chymotrypsin-like activity of the 20S proteasome," Bioorg Med Chem Lett., May 21, 2001:11(10):1317-9.

Gardner et al. "Characterization of peptidyl boronic acid inhibitors of mammalian 20S and 26S proteasomes and their inhibition of proteasomes in cultured cells," Biochem J., Mar. 1, 2000;346 Pt 2:447-54.

Goldberg et al. "The mechanism and functions of ATP-dependent proteases in bacterial and animal cells," Eur J Biochem., Jan. 15, 1992;203(1-2):9-23.

Goldberg et al., "Proteolysis, proteasomes and antigen presentation," Nature, Jun. 4, 1992;357(6377):375-9.

Iqbal et al., "Potent inhibitors of proteasome," J Med Chem., Jun. 23, 1995:38(13):2276-7.

Iqbal et al., "Potent α-Ketocarbonyl and Boronic Ester Derived Inhibitors of Proteasome," Bioorg. Med. Chem. Lett., 1996, vol. 6, pp. 287-290.

Kettner et al., "Inhibition of the serine proteases leukocyte elastase, pancreatic elastase, cathepsin G, and chymotrypsin by peptide boronic acids," J Biol Chem., Dec. 25, 1984:259(24):15106-14.

Kisselev et al., "Proteasome inhibitors: from research tools to drug candidates," Chem Biol., Aug. 2001;8(8):739-58.

Li et al., Isolation and characterization of a novel endogenous inhibitor of the proteasome, Biochemistry, Oct. 8, 1991;30(40):9709-15.

Matteson et al., "99% Chirally Selective Synthesis Via Pinanediol Boronic Esters: Insect Pheromones, Diols, and an Amino Alcohol," J. Am. Chem. Soc., 1986, vol. 108, pp. 810-819.

Murakami et al., "Endogenous inhibitor of nonlysosomal high molecular weight protease and calcium-dependent protease," Proc Nall Acad Sci., Oct. 1986;83(20):7588-92.

Nkemgu-Njinkeng et al., "Antitrypanosomal Activities of Proteasome Inhibitors," Antimicrob. Agents Chemother., Jun. 2002;46(6):2038-40.

Orlowski et al., "The multicatalytic proteinase complex, a major extralysosomal proteolytic system," Biochemistry, Nov. 13, 1990;29(45):10289-97.

Purandare et al., "Identification of a Potent and Rapidly Reversible Inhibitor of the 20S-Proteasome," Bioorganic & Medicinal Chemistry Letters, 2004, pp. 1-4.

Rivett et al. "The multicatalytic proteinase of mammalian cells," Arch Biochem Biophys., Jan. 1989;268(1):1-8.

Rivett et al., "The multicatalytic proteinase. Multiple proteolytic activities," J. Biol. Chem., Jul. 25, 1989;264(21):12215-9.

Rock et al., "Inhibitors of the proteasome block the degradation of most cell proteins and the generation of peptides presented on MHC class I molecules," Cell., Sep. 9, 1994;78(5):761-71.

Tanaka et al., "Proteasome protein and gene structures," New Biol., 1992, vol. 4(3):173-187.

Tsubuki et al., "Purification and characterization of a Z-Leu-Leu-Leu-MCA degrading protease expected to regulate neurite formation: a novel catalytic activity in proteasome," Biochem Biophys Res Commun., 1993, No. 15;196(3):1195-201.

Vinitsky et al., "Inhibition of the chymotrypsin-like activity of the pituitary multicatalytic proteinase complex," Biochemistry, Oct. 6, 1992;31(39):9421-8.

Wu et al., "Proteasome Inhibitors Stimulate Activator Protein-1 Pathway Via Reactive Oxygen Species Production," FEBS Letters, 2002, vol. 526, Issue 1, pp. 101-105.

Zembower et al., "Versatile Synthetic Ligands for Affinity Chromatography of Serine Proteinases," In't'l J. of Peptide & Protein Research, 1996, vol. 47, Issue 5, pp. 405-413.

Simov, Biljana Peric. et al., Chiral Carbanions, Part 4: Borylation of (Trimethysily)methyl N,N-Dialkyl-carbamates-Diasteroselectivity and Structural Studies, Synthesis, 2004, No. 16, pp. 2704-2710.

Notice of Opposition against European Patent EP 1680507 B9 (corresponding to instant application), May 4, 2010.

"Protective Groups in Organic Synthesis," $3^{rd}$ edition, edited by Greene and Wuts, pp. 531-537, published in 1999.

Adams, "Proteasome inhibition: a novel approach to cancer therapy," Trends in Molecular Medicine, 2002, vol. 8(4), pp. S49-S54.

Bold et al., "Chemosensitization of Pancreatic Cancer by Inhibition of the 26S Proteasome," J. Surg. Res., 2001, vol. 100, pp. 11-17.

Cecil's Textbook of Medicine (2000). Principles of Cancer Therapy.

Dou et al., "Proteasome inhibitors as potential novel anticancer agents," Drug Resistance Updates, 1999, vol. 3, pp. 215-223.

Golub et al. "Molecular Classification of Cancer: Class Discovery and Class Prediction by Gene Expression Monitoring," Science, 1999, vol. 286, pp. 531-537.

King et al., "How Proteolysis Drives the Cell Cycle," Science, 1996, vol. 274, pp. 1652-1659.

Kupperman et al., "Evaluation of the Proteasome Inhibitor MLN9708 in Preclinical Models of Human Cancer," Cancer Research, 2010, vol. 70(5), pp. 1970-1980.

Lind et al., "Nuclear factor kB is upregulated in colorectal cancer," Surgery, 2001, vol. 130(2), pp. 363-369.

Mimnaugh et al., "Prevention of Cisplatin-DNA Adduct Repair and Potentiation of Cisplatin-Induced Apoptosis in Ovarian Carcinoma Cells by Proteasome Inhibitors," Biochemical Pharmacology, 2000, vol. 60, pp. 1343-1354.

Nabel, "Challenges and Opportunities for Development of an AIDS Vaccine," Nature, 2001, vol. 410, pp. 1002-1007.

Pantaleo et al., "Correlates of Immune Protection in HIV-1 Infection: what we know, what we don't know and what we should know," Nature Medicine, 2004, vol. 10(8), pp. 806-810.

Song et al., "Mitogen-activated Protein Kinase is Involved in the Degradation of p53 Protein in the Bryostatin-1-induced Differentiation of the Acute Promyelocytic Leukemia NB4 Cell Line," J. Biological Chem., 1999, vol. 274(3), pp. 1677-1682.

Velcade full prescribing information—Millennium.

European Opposition—Proprietor's Submissions, Sep. 5, 2011.

European Opposition—Main Request, Sep. 5, 2011.
European Opposition—Auxiliary Request 1, Sep. 5, 2011.
European Opposition—Auxiliary Request 2, Sep. 5, 2011.
European Opposition—Opponent's Reply, Sep. 19, 2011.
European Opposition—Proprietor's Response to Notice of Opposition, Jan. 17, 2011.
European Opposition—Proprietor's Amended Claims, Jan. 17, 2011.
European Opposition—Proprietor's Response 1 to Opponent's Reply, Sep. 21, 2011.
European Opposition—Main Request Replacement Page, Sep. 21, 2011.
European Opposition—Auxiliary Request 1 Replacement Page, Sep. 21, 2011.
European Opposition—Auxiliary Request 2 Replacement Page, Sep. 21, 2011.
European Opposition—Proprietor's Response 2 to Opponent's Reply, Sep. 21, 2011.
European Opposition—Hearing Minutes, Nov. 2, 2011.
European Opposition—Opponent Request to Correct Hearing Minutes, Nov. 20, 2011.
European Opposition—Proprietor Response to Opponent Request to Correct Hearing Minutes, Nov. 29, 2011.
European Opposition—Opposition Division Decision on Hearing Minutes, Dec. 5, 2011.
European Opposition—Opponent Response to Proprietor Response to Opponent Request, Dec. 7, 2011.
European Opposition—Opposition Division Opposition Decision, Dec. 14, 2011.
European Opposition—Text Approved by Opposition Division, Dec. 14, 2011.
European Opposition—Notices of Appeal, Feb. 23, 2012.
European Opposition—Opponent Grounds of Appeal, Apr. 23, 2012.
Hoffmann et al., Chemische Berichte 123 (1990), pp. 2387-2394.
Andersen et al., Chemische Berichte 122 (1989), pp. 1777-1782.
Wallace and Zong, Tetrahedron Letters 33(46), (1992), pp. 6941-6944.
European Opposition—Proprietor Main Request, Apr. 24, 2012.
European Opposition—Proprietor Grounds of Appeal, Apr. 24, 2012.
European Opposition—Proprietor First Auxiliary Request, Apr. 24, 2012.
European Opposition—Proprietor Second Auxiliary Request, Apr. 24, 2012.

* cited by examiner

PROTEASOME INHIBITORS AND PROCESSES FOR THEIR PREPARATION, PURIFICATION AND USE

CROSS REFERENCE TO RELATED APPLICATIONS

This application is a continuation of International Application No. PCT/US2010/061695, filed Dec. 22, 2010, which claims the benefit of U.S. Provisional Application No. 61/288,957, filed Dec. 22, 2009, the disclosures of which are incorporated herein by reference in their entireties.

FIELD OF THE INVENTION

The invention pertains to proteasome inhibitors and to processes for their preparation, purification and use.

BACKGROUND OF THE INVENTION

[(1R)-1-[[(2S,3R)-3-hydroxy-2-[6-phenyl-pyridine-2-carbonyl)amino]-1-oxobutyl]amino]-3-methylbutylboronic acid (Compound 1) is a reversible proteasome inhibitor in the peptide boronic acid class, which may be useful in the treatment of multiple myeloma. Compound 1 and analogs thereof are described in U.S. Pat. No. 7,576,206 (the '206 patent). The chemical structure of Compound 1 is provided below.

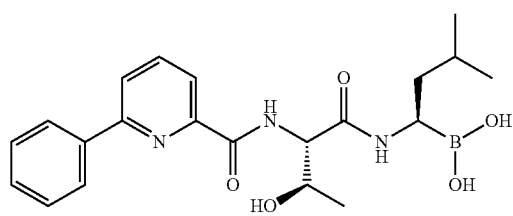

Compound 1

Compound 1 is challenging to work with from a pharmaceutical perspective. First, it is obtained in only about 25% yield in four steps from the chiral pinanediol derivative, (1R)-1-[(3aS,4S,6S,7aR)-hexahydro-3a,5,5-trimethyl-4,6-methano-1,3,2-benzodioxaborol-2-yl]-3-methylbutylamine

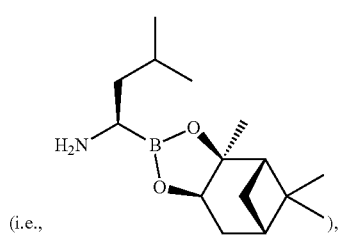 [SMILES: CC(C)C[C@H](N)B1O[C@@H]2C[C@@H]3C[C@@H](C3(C)C)[C@]2(C)O1]

(i.e.,            ), when synthesized according to the method described in the '206 patent, and only one of the prepared intermediates is crystalline. Second, Compound 1 is non-crystalline and hygroscopic, which presents purification and handling issues. For example, chromatographic purification of the Compound 1 obtained from the method of the '206 patent results in a purity of only 96-98%. Third, the immediate precursor to Compound 1 in method of the '206 patent is the pinanediol boronic ester derivative of Compound 1, which is obtained as a non-crystalline glassy foam, and only with difficulty and inefficiency can its diastereomeric purity be improved by chromatography. Therefore, the chiral pinanediol derivative starting material used to prepare the immediate precursor to Compound 1 must be prepared with high chiral purity, and the subsequent reactions must be rigorously controlled to avoid chiral scrambling, which are difficult tasks. Fourth, Compound 1 is unstable and subject to degradation upon exposure to air and/or light, with some batches degrading when stored at temperatures as low as 5° C. For that reason, the standard storage temperature for Compound 1 is −20° C. Fifth, Compound 1 has an occupational exposure limit (OEL) of only 0.3 μg/m$^3$, and therefore requires rigorous, expensive controls during manufacturing to prevent personnel exposure.

Bortezomib ([(1R)-3-methyl-1-({(2S)-3-phenyl-2-[(pyrazin-2-ylcarbonyl)amino]propanoyl}amino) butyl]boronic acid; marketed by Millennium Pharmaceuticals under the trade name Velcade®) is also a reversible proteasome inhibitor in the peptide boronic acid class, which is useful in the treatment of multiple myeloma. The chemical structure of bortezomib is provided below.

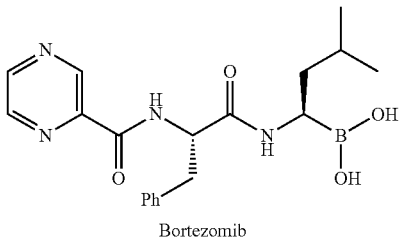 [SMILES: CC(C)C[C@H](NC(=O)[C@H](Cc1ccccc1)NC(=O)c1cnccn1)B(O)O]

Bortezomib

Bortezomib is also challenging to work with from a pharmaceutical perspective. Perhaps the biggest challenge is that in the syntheses described in U.S. Pat. No. 5,780,454 and U.S. Patent Application No. 2005/0240047, the diastereomeric purity of the bortezomib obtained is almost completely dependent upon the diastereomeric purity of the immediate precursor to bortezomib in the synthetic process. The immediate precursor is the pinanediol boronic ester derivative of bortezomib, which is a non-crystalline glassy foam that is difficult and inefficient to purify by chromatography.

Improved methods for preparing and purifying Compound 1 and bortezomib are required. Also required are high purity and storage stable forms of Compound 1.

SUMMARY OF THE INVENTION

The present invention provides a boronic ester of Formula I

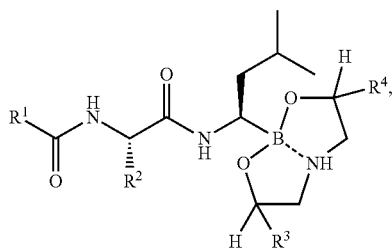

I wherein R$^1$ is 2-(6-phenyl)pyridinyl, R$^2$ is (1R)-1-hydroxyethyl, and R$^3$ and R$^4$ are H; R$^1$ is 2-(6-phenyl)pyridinyl, R$^2$ is (1R)-1-hydroxyethyl, and R$^3$ and R$^4$ are methyl; or R$^1$ is 2-pyrazinyl, $R^2$ is benzyl, and $R^3$ and $R^4$ are H. In certain embodiments, $R^1$ is 2-(6-phenyl)pyridinyl, $R^2$ is (1R)-1-hydroxyethyl, and $R^3$ and $R^4$ are H. In certain embodiments, $R^1$ is 2-(6-phenyl)pyridinyl, $R^2$ is (1R)-1-hydroxyethyl, and $R^3$ and $R^4$ are methyl. In certain embodiments, $R^1$ is 2-pyrazinyl, $R^2$ is benzyl, and $R^3$ and $R^4$ are H.

The present invention further provides a process for preparing a pharmaceutical composition, comprising the step of combining a boronic ester of the present invention with a pharmaceutically acceptable carrier, diluent, or excipient.

The present invention further provides Compound 1 having a chemical purity of at least 99.5% and a chiral purity of at least 99.5% de

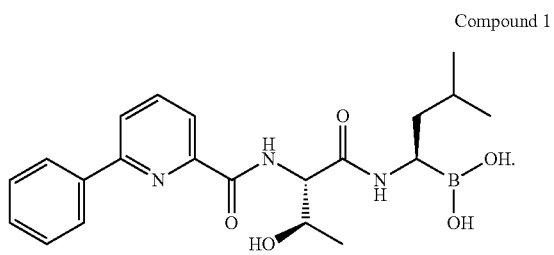 [SMILES: CC(C)C[C@H](NC(=O)[C@@H](NC(=O)c1cccc(-c2ccccc2)n1)[C@@H](C)O)B(O)O]

Compound 1

The present invention also provides a pharmaceutical composition comprising the Compound 1 of the present invention and a pharmaceutically acceptable carrier, diluent, or excipient.

The present invention further provides a process for preparing a pharmaceutical composition of a boronic acid of Formula IA

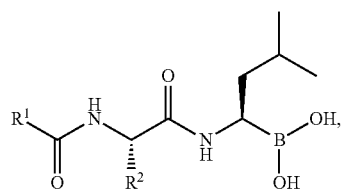

IA wherein $R^1$ is 2-(6-phenyl)pyridinyl and $R^2$ is (1R)-1-hydroxyethyl, or $R^1$ is 2-pyrazinyl and $R^2$ is benzyl;

comprising the steps of:
(a) converting a boronic ester of Formula I,

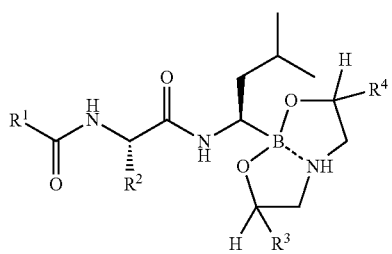

I wherein
$R^1$ is 2-(6-phenyl)pyridinyl, $R^2$ is (1R)-1-hydroxyethyl, and $R^3$ and $R^4$ are H;

$R^1$ is 2-(6-phenyl)pyridinyl, $R^2$ is (1R)-1-hydroxyethyl, and $R^3$ and $R^4$ are methyl; or $R^1$ is 2-pyrazinyl, $R^2$ is benzyl, and $R^3$ and $R^4$ are H;

into a boronic acid of Formula IA; and (b) combining the boronic acid of Formula IA with a pharmaceutically acceptable carrier, diluent, or excipient.

In certain embodiments, $R^1$ is 2-(6-phenyl)pyridinyl, $R^2$ is (1R)-1-hydroxyethyl, and $R^3$ and $R^4$ are H. In certain embodiments, $R^1$ is 2-(6-phenyl)pyridinyl, $R^2$ is (1R)-1-hydroxyethyl, and $R^3$ and $R^4$ are methyl. In certain embodiments, $R^1$ is 2-pyrazinyl, $R^2$ is benzyl, and $R^3$ and $R^4$ are H.

The present invention further provides a process for purifying a boronic acid of Formula IA

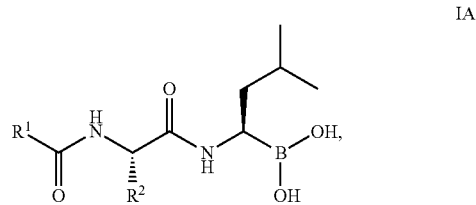

IA wherein
$R^1$ is 2-(6-phenyl)pyridinyl and $R^2$ is (1R)-1-hydroxyethyl, or $R^1$ is 2-pyrazinyl and $R^2$ is benzyl;

comprising the steps of:
(a) converting the boronic acid of Formula IA into a boronic ester of Formula VII

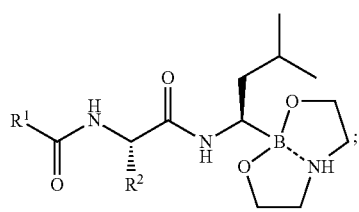

VII (b) crystallizing the boronic ester of Formula VII from solution;
(c) isolating the crystallized boronic ester of Formula VII from the solution; and
(d) converting the isolated boronic ester of Formula VII into a boronic acid of Formula IA.

In certain embodiments, $R^1$ is 2-(6-phenyl)pyridinyl and $R^2$ is (1R)-1-hydroxyethyl. In certain embodiments, $R^1$ is 2-pyrazinyl and $R^2$ is benzyl.

The present invention further provides a process for preparing a boronic acid of Formula IA

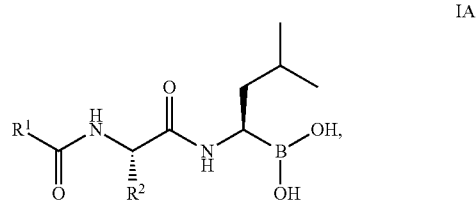

IA wherein
R¹ is 2-(6-phenyl)pyridinyl and R² is (1R)-1-hydroxyethyl, or R¹ is 2-pyrazinyl and
R² is benzyl;
comprising the steps of
(a) crystallizing a boronic ester of Formula I from a solution of a boronic ester of Formula V

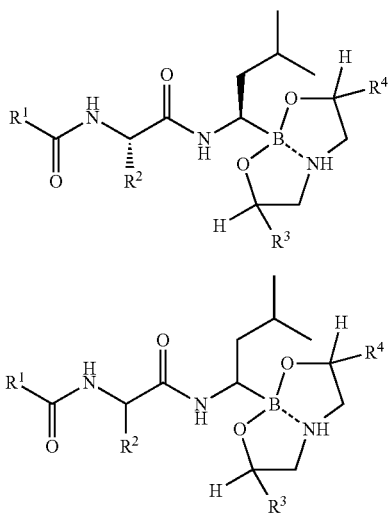

wherein
R¹ is 2-(6-phenyl)pyridinyl, R² is (1R)-1-hydroxyethyl, and R³ and R⁴ are H;
R¹ is 2-(6-phenyl)pyridinyl, R² is (1R)-1-hydroxyethyl, and R³ and R⁴ are methyl; or
R¹ is 2-pyrazinyl, R² is benzyl, and R³ and R⁴ are H; and
(b) converting the boronic ester of Formula I into the boronic acid of Formula IA.

In certain embodiments, R¹ is 2-(6-phenyl)pyridinyl, R² is (1R)-1-hydroxyethyl, and R³ and R⁴ are H. In certain embodiments, R¹ is 2-(6-phenyl)pyridinyl, R² is (1R)-1-hydroxyethyl, and R³ and R⁴ are methyl. In certain embodiments, R¹ is 2-pyrazinyl, R² is benzyl, and R³ and R⁴ are H.

DETAILED DESCRIPTION OF ILLUSTRATIVE EMBODIMENTS

Definitions

Figure 1:
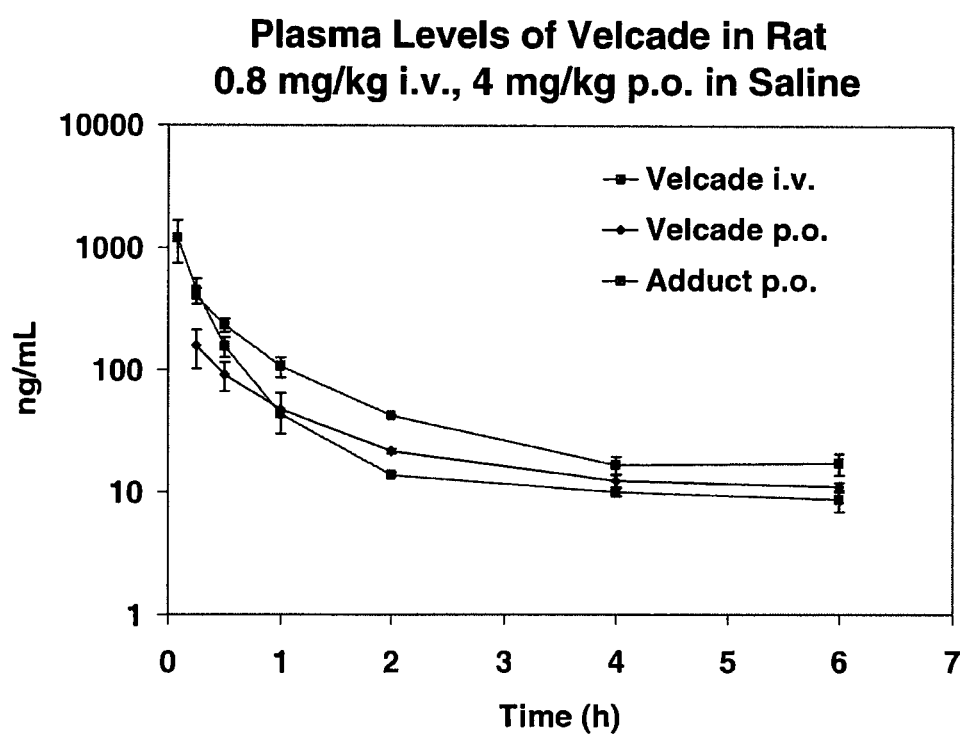
FIG. 1 depicts plasma levels of Velcade® in rat at 0.8 mg/kg i.v., 4 mg/kg p.o. in saline.

"Isolating" refers to separating a component (e.g., a compound) from a mixture.
"Chiral purity" refers to the proportion of one enantiomer or diastereomer in a mixture of enantiomers or diastereomers, and is expressed as enantiomeric excess (% ee) or diastereomeric excess (% de), which are defined as ((|enantiomer of interest–other enantiomer|/(enantiomer of interest+ other enantiomer))*100%, or ((diastereomer of interest)– (other diastereomers)/(total diastereomers))*100%.
"Purifying" refers to increasing the purity of a compound.
"Chemical Purity" refers to the percentage by weight of one component in a mixture (i.e., ([quantity of component of interest]/[total quantity of all components])*100%).
"Solution" refers to a solvent containing a substance(s) that is at least partially dissolved; and which may contain undissolved (e.g., solid) substance(s)
"Alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms, preferably 1-4 carbon atoms, and can be substituted or unsubstituted.
"Alkenyl" or "alkenyl group" refers to a monoradical of a branched or unbranched hydrocarbon chain containing at least one double bond. Examples include, but are not limited to, ethenyl, 3-buten-1-yl, 2-ethenylbutyl, and 3-hexen-1-yl. Alkenyl groups typically contain 2-10 carbon atoms, such as 2-6 carbon atoms, preferably 2-4 carbon atoms, and can be substituted or unsubstituted.
"Alkynyl" or "alkynyl group" refers to a monoradical of a branched or unbranched hydrocarbon chain containing at least one triple bond. Examples include, but are not limited to, ethynyl, 3-butyn-1-yl, propynyl, 2-butyn-1-yl, and 3-pentyn-1-yl. Alkynyl groups typically contain 2-10 carbon atoms, such as 2-6 carbon atoms, preferably 2-4 carbon atoms, and can be substituted or unsubstituted.
"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$CI=CH_2$, —$C≡C$— $CF_3$, —$CHFCH_2CH_3$ and —$CHFCH_2CF_3$.
"Halogen" includes fluorine, chlorine, bromine and iodine atoms.
"Pseudohalogen" refers to —OCN, —SCN, —$CF_3$, and —CN.
"Cycloalkyl" or "cycloalkyl group" refers to a monoradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo [2.2.1]heptane, bicyclo[2.2.1]heptene, bicyclo[3.1.1]heptane, bicyclo[3.2.1]octane, bicyclo[2.2.2]octane, bicyclo [3.2.2]nonane, bicyclo[3.3.1]nonane, and bicyclo[3.3.2] decane. Preferably, the cycloalkyl group contains from 3 to 10 ring atoms. More preferably, the cycloalkyl group contains from 3 to 7 ring atoms, such as 3 ring atoms, 5 ring atoms, 6 ring atoms, or 7 ring atoms.
"Cycloalkylalkyl" or "cycloalkylalkyl group" refers to an alkyl group in which a hydrogen atom is replaced by a cycloalkyl group, wherein alkyl group and cycloalkyl group are as previously defined (i.e., cycloalkylalkyl-). Cycloalkylalkyl groups can be substituted or unsubstituted. Examples include, but are not limited to, cyclohexylmethyl ($C_6H_{11}CH_2$—).

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Preferably, the aryl group contains 6 (i.e., phenyl) or 9 to 15 ring atoms. More preferably, the aryl group contains 6 (i.e., phenyl), 9 or 10 ring atoms. More preferably, the aryl group contains 6 (i.e., phenyl), or 9-11 ring atoms.

"Arylalkyl" or "arylalkyl group" refers to an alkyl group in which a hydrogen atom is replaced by an aryl group, wherein alkyl group and aryl group are as previously defined (i.e., arylalkyl-). Arylalkyl groups can be substituted or unsubstituted. Examples include, but are not limited to, benzyl ($C_6H_5CH_2$—).

"Heterocycloalkyl" or "heterocycloalkyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane, 2,6-diaza-bicyclo[3.2.2]nonane, [1,4]oxaphosphinane 4-oxide, [1,4]azaphosphinane 4-oxide, [1,2]oxaphospholane 2-oxide, phosphinane 1-oxide, [1,3]azaphospholidine 3-oxide, and [1,3]oxaphospholane 3-oxide. Preferably, the heterocycloalkyl group contains, in addition to carbon atom(s), at least one nitrogen, oxygen, or sulfur. More preferably, the heterocycloalkyl group contains, in addition to carbon atom(s), at least one nitrogen or oxygen. More preferably, the heterocycloalkyl group contains, in addition to carbon atom(s), at least one nitrogen. Preferably, the heterocycloalkyl group contains from 3 to 10 ring atoms. More preferably, the heterocycloalkyl group contains from 3 to 7 ring atoms. More preferably, the heterocycloalkyl group contains from 5 to 7 ring atoms, such as 5 ring atoms, 6 ring atoms, or 7 ring atoms. Unless otherwise indicated, the foregoing heterocycloalkyl groups can be C- attached or N-attached where such is possible and results in the creation of a stable structure. For example, piperidinyl can be piperidin-1-yl (N-attached) or piperidin-4-yl (C-attached).

"Heterocycloalkylalkyl" or "heterocycloalkylalkyl group" refers to an alkyl group in which a hydrogen atom is replaced by a heterocycloalkyl group, wherein alkyl group and heterocycloalkyl group are as previously defined (i.e., heterocycloalkylalkyl-). Heteroycloalkylalkyl groups can be substituted or unsubstituted. Examples include, but are not limited to, pyrrolidinylmethyl ($C_4H_8CH_2$—).

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0*2,7*]dodeca-2(7),3,5-trienyl, 12-oxa-10-aza-tricyclo[6.3.1.0*2,7*]dodeca-2(7),3,5-trienyl, 12-aza-tricyclo[7.2.1.0*2,7*]dodeca-2(7),3,5-trienyl, 10-aza-tricyclo[6.3.2.0*2,7*]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Preferably, the heteroaryl group contains 5, 6, or 8-15 ring atoms. More preferably, the heteroaryl group contains 5 to 10 ring atoms, such as 5, 6, 9, or 10 ring atoms.

"Heteroarylalkyl" or "heteroarylalkyl group" refers to an alkyl group in which a hydrogen atom is replaced by a heteroaryl group, wherein alkyl group and heteroaryl group are as previously defined (i.e., heteroarylalkyl-). Heteroarylalkyl groups can be substituted or unsubstituted. Examples include, but are not limited to, the pyridinylmethyl isomers

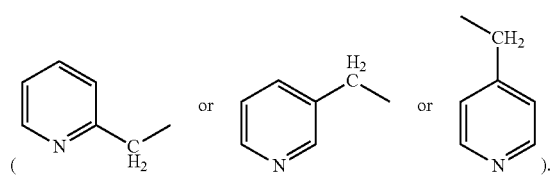

"Chemically stable" or "stable" refers to a compound that is sufficiently robust to be isolated to a useful degree of purity from a reaction mixture. The present invention is directed only to stable compounds.

"Substituted" refers to a derivative of a compound or chemical group in which a hydrogen atom is replaced by another atom or group. An example of substituted benzene is bromobenzene. An example of a substituted bromobenzene is 2-bromophenol. When lists of alternative substituents include members which, owing to valency requirements, chemical stability, or other reasons, cannot be used to substitute a particular group, the list is intended to be read in context to include those members of the list that are suitable for substituting the particular group. When a compound or chemical group herein is "substituted" it may have up to the full valance of substitution, provided the resulting compound or chemical group is a stable compound or stable chemical group; for example, a methyl group may be substituted by 1, 2, or 3 substituents, an ethyl group may be substituted by 1, 2, 3, 4, or 5 substituents, a phenyl group may be substituted by 1, 2, 3, 4, or 5 substituents, and the like. Atoms and groups with which a compound or chemical group may be substituted include, but are not limited to, halogen, nitro, hydroxy, alkoxy, aryloxy, carbonyl, hydroxycarbonyl, alkoxycarbonyl, aminocarbonyl, alkylaminocarbonyl, amino, alkylamino, alkyl, alkoxyalkyl, aminoalkyl, haloalkyl, alkenyl, alkynyl, aryl, arylalkyl, heteroaryl, heteroarylalkyl, cycloalkyl, cycloalkylalkyl, heterocycloalkyl, heterocycloalkylalkyl, pseudohalogen, alkylthio, sulfonyl, alkylsulfonyl, alkylaminosulfonyl, alkylcarbonyloxy, aminocarbonyloxy, alkylaminocarbonyloxy, alkylcarbonylamino, alkoxycarbonylamino, alkylsulfonylamino, aminocarbonylamino, and alkylaminocarbonylamino Further examples of atoms and groups with which a compound or chemical group may be substituted include, but are not limited to, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, 6-21 membered heteroarylalkyl optionally substituted by 1-27 $R^{49}$, halogen, —CN, —C(=O)R$^{100}$, —C(=O)OR$^{100}$, —C(=O)NR$^{102}$R$^{103}$, —C(=O)C(=O)R$^{100}$, —C(=NR$^{105}$)R$^{100}$, —C(=NR$^{105}$)NR$^{102}$R$^{103}$, —C(=NOH)NR$^{102}$R$^{103}$, —C(=NOR$^{106}$)R$^{100}$, —C(=NNR$^{102}$R$^{103}$)R$^{100}$, —C(=NNR$^{104}$C(=O)R$^{101}$)R$^{100}$, —C(=NNR$^{104}$C(=O)OR$^{101}$)R$^{100}$, —C(=S)NR$^{102}$R$^{103}$, —NC, —NO$_2$, —NR$^{102}$R$^{103}$, —NR$^{104}$NR$^{102}$R$^{103}$, —N=NR$^{104}$, =NR$^{100}$, =NOR$^{100}$, —NR$^{104}$OR$^{106}$, —NR$^{104}$C(=O)R$^{100}$, —NR$^{104}$C(=O)C(=O)R$^{100}$, —NR$^{104}$C(=O)OR$^{101}$, —NR$^{104}$C(=O)C(=O)OR$^{101}$, —NR$^{104}$C(=O)NR$^{102}$R$^{103}$, —NR$^{104}$C(=O)NR$^{104}$C(=O)R$^{100}$, —NR$^{104}$C(=O)NR$^{104}$C(=O)OR$^{100}$, —NR$^{104}$C(=NR$^{105}$)NR$^{102}$R$^{103}$, —NR$^{104}$C(=O)C(=O)R$^{100}$, —NR$^{104}$C(=S)R$^{100}$, —NR$^{104}$C(=S)OR$^{100}$, —NR$^{104}$C(=S)NR$^{102}$R$^{103}$, —NR$^{104}$S(=O)$_2$R$^{101}$, —NR$^{104}$S(=O)$_2$NR$^{102}$R$^{103}$, —NR$^{104}$P(=O)R$^{108}$R$^{108}$, —NR$^{104}$P(O)(NR$^{102}$R$^{103}$)(NR$^{102}$R$^{103}$), —NR$^{104}$P(=O)(OR$^{100}$(OR$^{100}$), —NR$^{104}$P(=O)(SR$^{100}$)(SR$^{100}$), —OR$^{100}$, =O, —OCN, —OC(=O)R$^{100}$, —OC(=O)NR$^{102}$R$^{103}$, —OC(=O)OR$^{100}$, —OC(=NR$^{105}$)NR$^{102}$R$^{103}$, —OS(=O)R$^{100}$, —OS(=O)$_2$R$^{100}$, —OS(=O)$_2$OR$^{100}$, —OS(=O)$_2$NR$^{102}$R$^{103}$, —OP(=O)R$^{108}$R$^{108}$, —OP(=O)(NR$^{102}$R$^{103}$)(NR$^{102}$R$^{103}$), —OP(=O)(OR$^{100}$)(OR$^{100}$), —OP(=O)(SR$^{100}$)(SR$^{100}$), —SCN, =S, —S(=O)$_n$R$^{100}$, —S(=O)$_2$OR$^{100}$, —SO$_3$R$^{107}$, —S(=O)$_2$NR$^{102}$R$^{103}$, —S(=O)NR$^{102}$R$^{103}$, —SP(=O)R$^{108}$R$^{108}$, —SP(=O)(NR$^{102}$R$^{103}$)(NR$^{102}$R$^{103}$), —SP(=O)(OR$^{100}$)(OR$^{100}$), —SP(=O)(SR$^{100}$)(SR$^{100}$), —P(=O)R$^{108}$R$^{108}$, —P(=O)(NR$^{102}$R$^{103}$)(NR$^{102}$R$^{103}$), —P(=O)(OR$^{100}$)(OR$^{100}$), or —P(=O)(SR$^{100}$(SR$^{100}$); wherein $R^{49}$ at each occurrence is independently chosen from $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, 6-21 membered heteroarylalkyl optionally substituted by 1-27 $R^{179}$, halogen, —CN, —C(=O)R$^{170}$, —C(=O)OR$^{170}$, —C(=O)NR$^{172}$R$^{173}$, —C(=O)C(=O)R$^{170}$, —C(=NR$^{175}$)R$^{170}$, —C(=NR$^{175}$)NR$^{172}$R$^{173}$, —C(=NOH)NR$^{172}$R$^{173}$, —C(=NOR$^{176}$)R$^{170}$, —C(=NNR$^{172}$R$^{173}$)R$^{170}$, —C(=NNR$^{174}$C(=O)R$^{171}$)R$^{170}$, —C(=NNR$^{174}$C(=O)OR$^{171}$)R$^{170}$, —C(=S)NR$^{172}$R$^{173}$, —NC, —NO$_2$, —NR$^{172}$R$^{173}$, —NR$^{174}$NR$^{172}$R$^{173}$, —N=NR$^{174}$, =NR$^{170}$, =NOR$^{170}$, —NR$^{174}$OR$^{176}$, —NR$^{174}$C(=O)R$^{170}$, —NR$^{174}$C(=O)C(=O)R$^{170}$, —NR$^{174}$C(=O)OR$^{171}$, —NR$^{174}$C(=O)C(=O)OR$^{171}$, —NR$^{174}$C(=O)NR$^{172}$R$^{173}$, —NR$^{174}$C(=O)NR$^{174}$C(=O)R$^{170}$, —NR$^{174}$C(=O)NR$^{174}$C(=O)OR$^{170}$, —NR$^{174}$C(=NR$^{175}$)NR$^{172}$R$^{173}$, —NR$^{174}$C(=O)C(=O)NR$^{172}$R$^{173}$, —NR$^{174}$C(=S)R$^{170}$, —NR$^{174}$C(=S)OR$^{170}$, —NR$^{174}$C(=S)NR$^{172}$R$^{173}$, —NR$^{174}$S(=O)$_2$R$^{171}$, —NR$^{174}$S(=O)$_2$NR$^{172}$R$^{173}$, —NR$^{174}$P(=O)R$^{178}$R$^{178}$, —NR$^{174}$P(=O)(NR$^{172}$R$^{173}$)(NR$^{172}$R$^{173}$), —NR$^{174}$P(=O)(OR$^{170}$)(OR$^{170}$), —NR$^{174}$P(=O)(SR$^{170}$)(SR$^{170}$), —OR$^{170}$, =O, —OCN, —OC(=O)R$^{170}$, —OC(=O)NR$^{172}$R$^{173}$, —OC(=O)OR$^{170}$, —OC(=NR$^{175}$)NR$^{172}$R$^{173}$, —OS(=O)R$^{170}$, —OS(=O)$_2$R$^{170}$, —OS(=O)$_2$OR$^{170}$, —OS(=O)$_2$NR$^{172}$R$^{173}$, —OP(=O)R$^{178}$R$^{178}$, —OP(=O)(NR$^{172}$R$^{173}$)(NR$^{172}$R$^{173}$), —OP(=O)(OR$^{170}$)(OR$^{170}$), —OP(=O)(SR$^{170}$)(SR$^{170}$), —SCN, =S, —S(=O)$_n$R$^{170}$, —S(=O)$_2$OR$^{170}$, —SO$_3$R$^{177}$, —S(=O)$_2$NR$^{172}$R$^{173}$, —S(=O)NR$^{172}$R$^{173}$, —SP(=O)R$^{178}$R$^{178}$, —SP(=O)(NR$^{172}$R$^{173}$)(NR$^{172}$R$^{173}$), —SP(=O)(OR$^{170}$)(OR$^{170}$), —SP(=O)(SR$^{170}$)(SR$^{170}$), —P(=O)R$^{178}$R$^{178}$, —P(=O)(NR$^{172}$R$^{173}$)(NR$^{172}$R$^{173}$), —P(=O)(OR$^{170}$)(OR$^{170}$), and —P(=O)(SR$^{170}$)(SR$^{170}$);

$R^{100}$, $R^{101}$, $R^{104}$, $R^{105}$, $R^{106}$, $R^{107}$, $R^{170}$, $R^{171}$, $R^{174}$, $R^{175}$, $R^{176}$ and $R^{177}$ at each occurrence is independently chosen from H, $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{7-16}$arylalkyl optionally substituted by 1-19 $R^{189}$, $C_{3-11}$cycloalkyl optionally substituted by 1-21 $R^{189}$, $C_{4-17}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^{108}$ and $R^{178}$ at each occurrence is independently chosen from $C_{1-6}$alkyl optionally substituted by 1-13 $R^{189}$, $C_{2-6}$alkenyl optionally substituted by 1-11 $R^{189}$, $C_{2-6}$alkynyl optionally substituted by 1-9 $R^{189}$, $C_{6-11}$aryl optionally substituted by 1-11 $R^{189}$, $C_{2-16}$arylalkyl optionally substituted by 1-19 $R^{189}$, $C_{3-11}$cycloalkyl optionally substituted by 1-21 $R^{189}$, $C_{4-12}$cycloalkylalkyl optionally substituted by 1-32 $R^{189}$, 3-15 membered heterocycloalkyl optionally substituted by 1-28 $R^{189}$, 4-21 membered heterocycloalkylalkyl optionally substituted by 1-40 $R^{189}$, 5-15 membered heteroaryl optionally substituted by 1-15 $R^{189}$, and 6-21 membered heteroarylalkyl optionally substituted by 1-27 $R^{189}$;

$R^{102}$, $R^{103}$, $R^{172}$ and $R^{173}$ at each occurrence is independently chosen from H, $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{2-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, and 6-21 membered heteroarylalkyl optionally substituted by 1-27 $R^{199}$;

or any $R^{102}$ and $R^{103}$, or $R^{172}$ and $R^{173}$ may form, together with the nitrogen atom to which they are attached, a 3-15 membered heterocycloalkyl optionally substituted by 1-28 $R^{209}$ or a 5-15 membered heteroaryl optionally substituted by 1-15 $R^{209}$;

$R^{179}$, $R^{189}$, $R^{199}$ and $R^{209}$ at each occurrence is independently chosen from $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{2-16}$arylalkyl optionally substituted by 1-19 $R^{219}$, $C_{3-11}$cycloalkyl optionally substituted by 1-21 $R^{219}$, $C_{4-12}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, 6-21 membered heteroarylalkyl optionally substituted by 1-27 $R^{219}$, halogen, —CN, —C(=O)$R^{210}$, —C(=O)O$R^{210}$, —C(=O)N$R^{212}R^{213}$, —C(=O)C(=O)$R^{210}$, —C(=N$R^{215}$)$R^{210}$, —C(=N$R^{215}$)N$R^{212}R^{213}$, —C(=NOH)N$R^{212}R^{213}$, —C(=NO$R^{216}$)$R^{210}$, —C(=NN$R^{212}R^{213}$)$R^{210}$, —C(=NN$R^{214}$C(=O)$R^{211}$)$R^{210}$, —C(=NN$R^{214}$C(=O)O$R^{211}$)$R^{210}$, —C(=S)N$R^{212}R^{213}$, —NC, —NO$_2$, —N$R^{212}R^{213}$, —N$R^{214}$N$R^{212}R^{213}$, —N=N$R^{214}$, =N$R^{210}$, =NO$R^{210}$, —N$R^{214}$O$R^{216}$, —N$R^{214}$C(=O)$R^{210}$, —N$R^{214}$C(=O)C(=O)$R^{210}$, —N$R^{214}$C(=O)O$R^{211}$, —N$R^{214}$C(=O)C(=O)O$R^{211}$, —N$R^{214}$C(=O)N$R^{212}R^{213}$, —N$R^{214}$C(=O)N$R^{214}$C(=O)$R^{210}$, —N$R^{214}$C(=O)N$R^{214}$C(=O)O$R^{210}$, —N$R^{214}$C(=N$R^{215}$)N$R^{212}R^{213}$, —N$R^{214}$C(=O)C(=O)N$R^{212}R^{213}$, —N$R^{214}$C(=S)$R^{210}$, —N$R^{214}$C(=S)O$R^{210}$, —N$R^{214}$C(=S)N$R^{212}R^{213}$, —N$R^{214}$S(=O)$_2R^{211}$, —N$R^{214}$S(=O)$_2$N$R^{212}R^{213}$, —N$R^{214}$P(=O)$R^{218}R^{218}$, —N$R^{214}$P(=O)(N$R^{212}R^{213}$)(N$R^{212}R^{213}$), —N$R^{214}$P(=O)(O$R^{210}$)(O$R^{210}$), —N$R^{214}$P(=O)(S$R^{210}$)(S$R^{210}$), —O$R^{210}$, =O, —OCN, —OC(=O)$R^{210}$, —OC(=O)N$R^{212}R^{213}$, —OC(=O)O$R^{210}$, —OC(=N$R^{215}$)N$R^{212}R^{213}$, —OS(=O)$R^{210}$, —OS(=O)$_2R^{210}$, —OS(=O)$_2$O$R^{210}$, —OS(=O)$_2$N$R^{212}$N$R^{213}$, —OP(=O)$R^{218}R^{218}$, —OP(=O)N$R^{213}R^{213}$)(N$R^{212}R^{213}$), —OP(=O)(O$R^{210}$)(O$R^{210}$), —OP(=O)(S$R^{210}$)(S$R^{210}$), —SCN, =S, —S(=O)$_nR^{210}$, —S(=O)$_2$O$R^{210}$, —SO$_3R^{217}$, —S(=O)$_2$N$R^{212}R^{213}$, —S(=O)N$R^{212}R^{213}$, —SP(=O)$R^{218}R^{218}$, —SP(=O)(N$R^{212}R^{213}$)(N$R^{212}R^{213}$), —SP(=O)(O$R^{210}$)(O$R^{210}$), —SP(=O)(S$R^{210}$)(S$R^{210}$), —P(=O)$R^{218}R^{218}$, —P(=O)(N$R^{212}R^{213}$)(N$R^{212}R^{213}$), —P(=O)(O$R^{210}$)(O$R^{210}$), and —P(=O)(S$R^{210}$)(S$R^{210}$);

$R^{210}$, $R^{211}$, $R^{214}$, $R^{215}$, $R^{216}$ and $R^{217}$ at each occurrence is independently chosen from H, $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{2-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{218}$ at each occurrence is independently chosen from $C_{1-6}$alkyl optionally substituted by 1-13 $R^{229}$, $C_{2-6}$alkenyl optionally substituted by 1-11 $R^{229}$, $C_{2-6}$alkynyl optionally substituted by 1-9 $R^{229}$, $C_{6-11}$aryl optionally substituted by 1-11 $R^{229}$, $C_{7-16}$arylalkyl optionally substituted by 1-19 $R^{229}$, $C_{3-11}$cycloalkyl optionally substituted by 1-21 $R^{229}$, $C_{4-17}$cycloalkylalkyl optionally substituted by 1-32 $R^{229}$, 3-15 membered heterocycloalkyl optionally substituted by 1-28 $R^{229}$, 4-21 membered heterocycloalkylalkyl optionally substituted by 1-40 $R^{229}$, 5-15 membered heteroaryl optionally substituted by 1-15 $R^{229}$, and 6-21 membered heteroarylalkyl optionally substituted by 1-27 $R^{229}$;

$R^{212}$ and $R^{213}$ at each occurrence is independently chosen from H, $C_{1-6}$alkyl optionally substituted by 1-13 $R^{239}$, $C_{2-6}$alkenyl optionally substituted by 1-11 $R^{239}$, $C_{2-6}$alkynyl optionally substituted by 1-9 $R^{239}$, $C_{4-17}$aryl optionally substituted by 1-11 $R^{239}$, $C_{7-16}$arylalkyl optionally substituted by 1-19 $R^{239}$, $C_{3-11}$cycloalkyl optionally substituted by 1-21 $R^{239}$, $C_{4-17}$cycloalkylalkyl optionally substituted by 1-32 $R^{239}$, 3-15 membered heterocycloalkyl optionally substituted by 1-28 $R^{239}$, 4-21 membered heterocycloalkylalkyl optionally substituted by 1-40 $R^{239}$, 5-15 membered heteroaryl optionally substituted by 1-15 $R^{239}$, and 6-21 membered heteroarylalkyl optionally substituted by 1-27 $R^{239}$;

or any $R^{212}$ and $R^{213}$ may form, together with the nitrogen atom to which they are attached, a 3-15 membered heterocycloalkyl optionally substituted by 1-28 $R^{249}$ or a 5-15 membered heteroaryl optionally substituted by 1-15 $R^{249}$;

$R^{219}$, $R^{229}$, $R^{239}$ and $R^{249}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{250}$, —C(=O)O$R^{250}$, —C(=O)N$R^{250}R^{250}$, —C(=O)C(=O)$R^{250}$, —C(=N$R^{250}$)$R^{250}$, —C(=N$R^{250}$)N$R^{250}R^{250}$, —C(=NOH)N$R^{250}R^{250}$, —C(=NOR$^{250}$)R$^{250}$, —C(=NNR$^{250}$R$^{250}$)R$^{250}$, —C(=NNR$^{250}$C(=O)R$^{250}$)R$^{250}$, —C(=NNR$^{250}$C(=O)OR$^{250}$)R$^{250}$, —C(=S)NR$^{250}$R$^{250}$, —NC, —NO$_2$, —NR$^{250}$R$^{250}$, —NR$^{250}$NR$^{250}$R$^{250}$, —N=NR$^{250}$, =NR$^{250}$, =NOR$^{250}$, —NR$^{250}$OR$^{250}$, —NR$^{250}$C(=O)R$^{250}$, —NR$^{250}$C(=O)C(=O)R$^{250}$, —NR$^{250}$C(=O)OR$^{250}$, —NR$^{250}$C(=O)C(=O)OR$^{250}$, —NR$^{250}$C(=O)NR$^{250}$R$^{250}$, —NR$^{250}$C(=O)NR$^{250}$C(=O)R$^{250}$, —NR$^{250}$C(=O)NR$^{250}$C(=O)OR$^{250}$, —NR$^{250}$C(=NR$^{250}$)NR$^{250}$R$^{250}$, —NR$^{250}$C(=O)C(=O)NR$^{250}$R$^{250}$, —NR$^{250}$C(=S)R$^{250}$, —NR$^{250}$C(=S)OR$^{250}$, —NR$^{250}$C(=S)NR$^{250}$R$^{250}$, —NR$^{250}$S(=O)$_2$R$^{250}$, —NR$^{250}$S(=O)$_2$NR$^{250}$R$^{250}$, —NR$^{250}$P(=O)R$^{251}$R$^{251}$, —NR$^{250}$P(=O)(NR$^{250}$R$^{250}$)(NR$^{250}$R$^{250}$), —NR$^{250}$P(=O)(OR$^{250}$)(OR$^{250}$), —NR$^{250}$P(=O)(SR$^{250}$)(SR$^{250}$), —OR$^{250}$, =O, —OCN, —OC(=O)R$^{250}$, —OC(=O)NR$^{250}$R$^{250}$, —OC(=O)OR$^{250}$, —OC(=NR$^{250}$)NR$^{250}$R$^{250}$, —OS(=O)R$^{250}$, —OS(=O)$_2$R$^{250}$, —OS(=O)$_2$OR$^{250}$, —OS(=O)$_2$NR$^{250}$R$^{250}$, —OP(=O)R$^{251}$R$^{251}$, —OP(=O)(NR$^{250}$R$^{250}$)(NR$^{250}$R$^{250}$), —OP(=O)(OR$^{250}$)(OR$^{250}$), —OP(=O)(SR$^{250}$)(SR$^{250}$), —SCN, =S, —S(=O)$_n$R$^{250}$, —S(=O)$_2$OR$^{250}$, —SO$_3$R$^{250}$, —S(=O)$_2$NR$^{250}$R$^{250}$, —S(=O)NR$^{250}$R$^{250}$, —SP(=O)R$^{251}$R$^{251}$, —SP(=O)(NR$^{250}$R$^{250}$)(NR$^{250}$R$^{250}$), —SP(=O)(OR$^{250}$)(OR$^{250}$), —SP(=O)(SR$^{250}$)(SR$^{250}$), —P(=O)R$^{251}$R$^{251}$, —P(=O)(NR$^{250}$R$^{250}$)(NR$^{250}$R$^{250}$), —P(=O)(OR$^{250}$)(OR$^{250}$), and —P(=O)(SR$^{250}$)(SR$^{250}$);

R$^{250}$ at each occurrence is independently chosen from H, C$_{1-6}$alkyl and C$_{1-6}$-haloalkyl;

R$^{251}$ at each occurrence is independently chosen from C$_{1-6}$alkyl and C$_{1-6}$-haloalkyl; and n at each occurrence is independently chosen from 0, 1, and 2. Further examples of atoms and groups with which a compound or chemical group may be substituted include, but are not limited to, C$_{1-6}$alkyl optionally substituted by 1-5 R$^{49}$, C$_{2-6}$alkenyl optionally substituted by 1-5 R$^{49}$, C$_{2-6}$alkynyl optionally substituted by 1-5 R$^{49}$, C$_{6-11}$aryl optionally substituted by 1-5 R$^{49}$, C$_{7-16}$arylalkyl optionally substituted by 1-5 R$^{49}$, C$_{3-11}$cycloalkyl optionally substituted by 1-5 R$^{49}$, C$_{4-17}$cycloalkylalkyl optionally substituted by 1-5 R$^{49}$, 3-15 membered heterocycloalkyl optionally substituted by 1-5 R$^{49}$, 4-21 membered heterocycloalkylalkyl optionally substituted by 1-5 R$^{49}$, 5-15 membered heteroaryl optionally substituted by 1-5 R$^{49}$, 6-21 membered heteroarylalkyl optionally substituted by 1-5 R$^{49}$, halogen, —CN, —C(=O)R$^{100}$, —C(=O)OR$^{100}$, —C(=O)NR$^{102}$R$^{103}$, —NC, —NO$_2$, —NR$^{1-2}$R$^{103}$, —NR$^{104}$OR$^{106}$, —NR$^{104}$C(=O)R$^{100}$, —NR$^{104}$C(=O)OR$^{101}$, —NR$^{104}$C(=O)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OC(=O)R$^{100}$, —OC(=O)NR$^{102}$R$^{103}$, —S(=O)$_n$R$^{100}$, or —S(=O)$_2$NR$^{102}$R$^{103}$; wherein R$^{49}$ at each occurrence is independently chosen from C$_{1-6}$alkyl, C$_{1-6}$haloalkyl, C$_{2-6}$alkenyl, C$_{2-6}$alkynyl, C$_{6-11}$aryl, C$_{7-16}$arylalkyl, C$_{3-11}$cycloalkyl, C$_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)R$^{170}$, —C(=O)OR$^{170}$, —C(=O)NR$^{172}$R$^{173}$, —NC, —NO$_2$, —NR$^{172}$R$^{173}$, —NR$^{174}$C(=O)R$^{170}$, —NR$^{174}$C(=O)OR$^{171}$, —NR$^{174}$C(=O)NR$^{172}$R$^{173}$, —NR$^{174}$S(=O)$_2$R$^{171}$, —NR$^{174}$S(=O)$_2$NR$^{172}$R$^{173}$, —OR$^{170}$, =O, —OC(=O)R$^{170}$, —OC(=O)NR$^{172}$R$^{173}$, —SCN, =S, —S(=O)$_n$R$^{170}$, and —S(=O)$_2$NR$^{172}$R$^{173}$;

R$^{100}$, R$^{101}$, R$^{102}$, R$^{103}$, R$^{104}$, R$^{106}$, R$^{170}$, R$^{171}$, R$^{172}$, R$^{173}$, and R$^{174}$ at each occurrence is independently chosen from H, C$_{1-6}$alkyl, and C$_{1-6}$haloalkyl; or any R$^{102}$ and R$^{103}$, or R$^{172}$ and R$^{173}$ may form, together with the nitrogen atom to which they are attached, a 3-15 membered heterocycloalkyl or a 5-15 membered heteroaryl; and n at each occurrence is independently chosen from 0, 1, and 2. Further examples of atoms and groups with which a compound or chemical group may be substituted include, but are not limited to, C$_{1-6}$alkyl optionally substituted by 1-5 R$^{49}$, C$_{6-11}$aryl optionally substituted by 1-5 R$^{49}$, C$_{3-11}$cycloalkyl optionally substituted by 1-5 R$^{49}$, 3-15 membered heterocycloalkyl optionally substituted by 1-5 R$^{49}$, 5-15 membered heteroaryl optionally substituted by 1-5 R$^{49}$, halogen, —CN, —C(=O)R$^{100}$, —C(=O)OR$^{100}$, —C(=O)NR$^{102}$R$^{103}$, —NO$_2$, —NR$^{102}$R$^{103}$, —NR$^{104}$C(=O)R$^{100}$, —NR$^{104}$C(=O)OR$^{101}$C(=O)NR$^{104}$C(=O)NR$^{102}$R$^{103}$, —NR$^{104}$S(=O)$_2$R$^{101}$, —NR$^{104}$S(=O)$_2$NR$^{102}$R$^{103}$, —OR$^{100}$, =O, —OC(=O)R$^{100}$, —OC(=O)NR$^{102}$R$^{103}$, —S(=O)$_n$R$^{100}$, or —S(=O)$_2$NR$^{102}$R$^{103}$; wherein R$^{49}$ at each occurrence is independently chosen from C$_{1-6}$alkyl, C$_{1-6}$haloalkyl, C$_{6-11}$aryl, C$_{7-16}$arylalkyl, C$_{3-11}$cycloalkyl, 3-15 membered heterocycloalkyl, 5-15 membered heteroaryl, halogen, —CN, —C(=O)R$^{170}$, —C(=O)OR$^{170}$, —C(=O)NR$^{172}$R$^{173}$, —NO$_2$, —NR$^{172}$R$^{173}$, —NR$^{174}$C(=O)R$^{170}$, —NR$^{174}$C(=O)OR$^{171}$, —NR$^{174}$C(=O)NR$^{172}$R$^{173}$, —NR$^{174}$S(=O)$_2$R$^{171}$, —NR$^{174}$S(=O)$_2$NR$^{172}$R$^{173}$, —OR$^{170}$, =O, —OC(=O)R$^{170}$, —OC(=O)NR$^{172}$R$^{173}$, —S(=O)$_n$R$^{170}$, and —S(=O)$_2$NR$^{172}$R$^{173}$;

R$^{100}$, R$^{101}$, R$^{102}$, R$^{103}$, R$^{104}$, R$^{170}$, R$^{171}$, R$^{172}$, R$^{173}$, and R$^{174}$ at each occurrence is independently chosen from H, C$_{1-6}$alkyl, and C$_{1-6}$haloalkyl;

or any R$^{102}$ and R$^{103}$, or R$^{172}$ and R$^{173}$ may form, together with the nitrogen atom to which they are attached, a 3-6 membered heterocycloalkyl or a 5-10 membered heteroaryl; and n at each occurrence is independently chosen from 0, 1, and 2. Further examples of atoms and groups with which a compound or chemical group may be substituted include, but are not limited to, C$_{1-6}$alkyl optionally substituted by 1-5 R$^{49}$, halogen, —CN, —C(=O)R$^{100}$, —C(=O)OR$^{100}$, —C(=O)NR$^{102}$R$^{103}$, —NO$_2$, —NR$^{102}$R$^{103}$, —OR$^{100}$, =O, —OC(=O)R$^{100}$, —OC(=O)NR$^{102}$R$^{103}$, —S(=O)$_n$R$^{100}$, or —S(=O)$_2$NR$^{102}$R$^{103}$; wherein R$^{49}$ at each occurrence is independently chosen from C$_{6-11}$aryl, 5-15 membered heteroaryl, halogen, —CN, —C(=O)R$^{170}$, —C(=O)OR$^{170}$, —C(=O)NR$^{172}$R$^{173}$, —NO$_2$, —NR$^{172}$R$^{173}$, —OR$^{170}$, =O, —OC(=O)R$^{170}$, —OC(=O)NR$^{172}$R$^{173}$, —S(=O)$_n$R$^{170}$, and —S(=O)$_2$NR$^{172}$R$^{173}$;

R$^{100}$, R$^{102}$, R$^{103}$, R$^{170}$, R$^{172}$, and R$^{173}$ at each occurrence is independently chosen from H, C$_{1-6}$alkyl, and C$_{1-6}$haloalkyl;

or any $R^{102}$ and $R^{103}$, or $R^{172}$ and $R^{173}$ may form, together with the nitrogen atom to which they are attached, a 3-6 membered heterocycloalkyl or a 5-10 membered heteroaryl; and n at each occurrence is independently chosen from 0, 1, and 2. Further examples of atoms and groups with which a compound or chemical group may be substituted include, but are not limited to, $C_{1-6}$alkyl, $C_{1-6}$haloalkyl, $C_{7-15}$arylalkyl, halogen, and hydroxy.

Process for Preparation

The present invention provides a process for preparing a boronic ester of Formula I

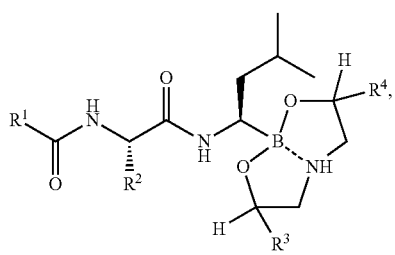

I wherein $R^1$ is 2-(6-phenyl)pyridinyl and $R^2$ is (1R)-1-hydroxyethyl, or $R^1$ is 2-pyrazinyl and $R^2$ is benzyl; and $R^3$ and $R^4$ are H, or $R^3$ and $R^4$ are methyl;

comprising the steps of:

(a) preparing an amide of Formula IV

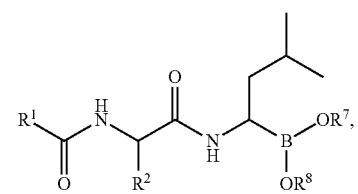

IV wherein $R^2$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^2$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula V

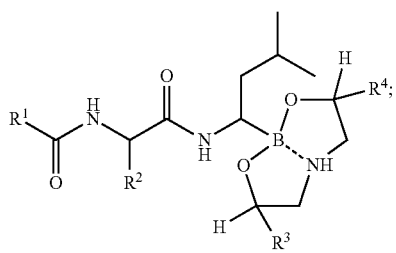

V and (c) crystallizing the boronic ester of Formula I from a solution of the boronic ester of Formula V.

In one embodiment of the present invention, $R^1$ is 2-(6-phenyl)pyridinyl and $R^2$ is (1R)-1-hydroxyethyl. In another embodiment, $R^1$ is 2-pyrazinyl and $R^2$ is benzyl.

In one embodiment, $R^3$ and $R^4$ are H. In another embodiment, $R^3$ and $R^4$ are methyl.

In one embodiment, $R^1$ is 2-(6-phenyl)pyridinyl, $R^2$ is (1R)-1-hydroxyethyl, and $R^3$ and $R^4$ are H; $R^1$ is 2-(6-phenyl) pyridinyl, $R^2$ is (1R)-1-hydroxyethyl, and $R^3$ and $R^4$ are methyl; or $R^1$ is 2-pyrazinyl, $R^2$ is benzyl, and $R^3$ and $R^4$ are H. In one embodiment, $R^1$ is 2-(6-phenyl)pyridinyl, $R^2$ is (1R)-1-hydroxyethyl, and $R^3$ and $R^4$ are H. In another embodiment, $R^1$ is 2-(6-phenyl)pyridinyl, $R^2$ is (1R)-1-hydroxyethyl, and $R^3$ and $R^4$ are methyl. In another embodiment, $R^1$ is 2-pyrazinyl, $R^2$ is benzyl, and $R^3$ and $R^4$ are H.

The manner of preparing the amide of Formula IV in step (a) is not critical. Preferably, the amide of Formula IV is prepared by coupling a compound of Formula II

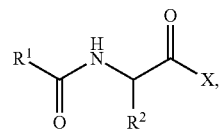

II with an amine of Formula III

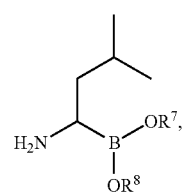

III to form an amide of Formula IV, wherein

X is OH or a leaving group. Thus, in a preferred embodiment the present invention provides a process for preparing a boronic ester of Formula I

I

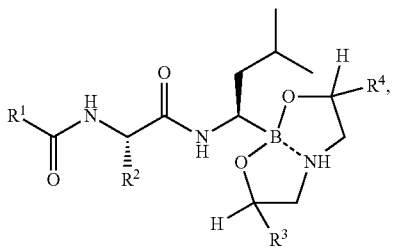

wherein
R¹ is 2-(6-phenyl)pyridinyl and R² is (1R)-1-hydroxyethyl, or R¹ is 2-pyrazinyl and
R² is benzyl; and
R³ and R⁴ are H, or R³ and R⁴ are methyl;
comprising the steps of:
(a) coupling a compound of Formula II

II

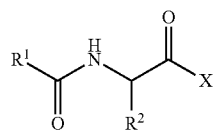

with an amine of Formula III

III

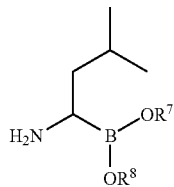

to form an amide of Formula IV

IV

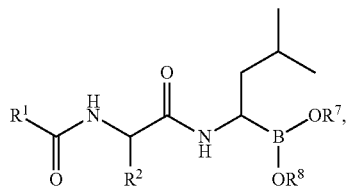

wherein
X is OH or a leaving group; and
R⁷ and R⁸ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or R⁷ and R⁸, together with the boron and oxygen atoms to which they are attached, form an optionally substituted 5-10 membered carbon-containing ring having 0-2 additional heteroatoms chosen from nitrogen, oxygen and sulfur;
(b) if the amide of Formula IV is not a boronic ester of Formula V, converting the amide of Formula IV into a boronic ester of Formula V

V

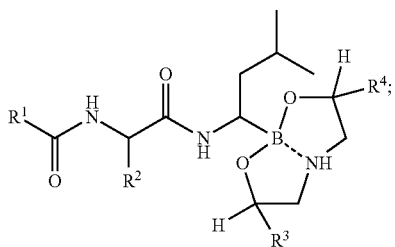

and
(c) crystallizing the boronic ester of Formula I from a solution of the boronic ester of Formula V.

The coupling reaction in step (a) can be performed using any suitable conditions, such as standard peptide coupling conditions well known to those of ordinary skill in the art. The leaving group X is any group capable of nucleophilic displacement by the amino group of the amine of Formula III. In some embodiments, the moiety —C(O)—X in the compound of Formula II is an acid chloride or an activated ester, such as an O—(N-hydroxysuccinimide)ester. Preferably, the moiety —C(O)—X in the compound of Formula II is an activated ester, such as an O—(N-hydroxysuccinimide)ester. Preferably, the acid chloride or activated ester is generated in situ, such as by contacting an acid of formula R¹C(=O)OH with a chloride donor such as thionyl chloride or oxalyl chloride, or by contacting an acid of formula R¹C(=O)OH, with a peptide coupling reagent. Preferably, an activated ester is generated in situ by contacting a compound of Formula II, wherein X is OH, with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., benzotriazol-1-yloxytris(dimethylamino)phosphonium hexafluorophosphate (BOP reagent); and uronium reagents, e.g., O-(1H-benzotriazol-1-yl)-N,N,N',N'-tetramethyluronium tetrafluoroborate (TBTU) or 2-(7-aza-1H-benzotriazole-1-yl)-1,1,3,3-tetramethyluronium hexafluorophosphate (HATU). In some embodiments, the coupling reaction is carried out in the presence of a coupling agent and a base, such as an amine base, for example, diisopropylethylamine, diethyl amine, NMM (N-methylmorpholine), DIPEA (N,N-diisopropylethylamine, Hunig's base), or a mixture thereof The coupling reaction is typically carried out in an organic solvent such as, for example, DMF (N,N-dimethylformamide), DMA (N,N-dimethylacetamide), toluene, dichloromethane, dichloroethane, or a mixture thereof.

The compound of Formula II contains a stereogenic center at the carbon to which R² is attached. Therefore, two isomers of the compound of Formula II are possible (IIa and IIb):

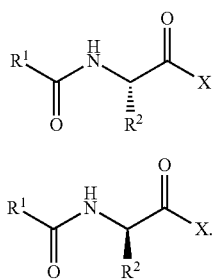

The isomer of Formula IIa contains the desired stereochemistry present in the boronic ester of Formula I. Therefore, the compound of Formula II must contain at least some of the isomer of Formula IIa. An advantage of the present invention is that the boronic ester of Formula I is obtained with very high chiral purity even if the compound of Formula II contains a significant quantity of the isomer of Formula IIb. Although the chiral purity of the compound of Formula II is not critical, it is preferred that the chiral purity of the compound of Formula II is at least 0% ee (i.e., racemic; ratio of IIa to IIb is ≥50/50). More preferably, the chiral purity of the compound of Formula II is at least 50% ee (i.e., ratio of IIa to IIb is ≥75/25). More preferably, the chiral purity of the compound of Formula II is at least 70% ee (i.e., ratio of IIa to IIb is 85/15). More preferably, the chiral purity of the compound of Formula II is at least 80% ee (i.e., ratio of IIa to IIb is ≥90/10). More preferably, the chiral purity of the compound of Formula II is at least 90% ee (i.e., ratio of IIa to IIb is ≥95/5). More preferably, the chiral purity of the compound of Formula II is at least 94% ee (i.e., ratio of IIa to IIb is ≥97/3). More preferably, the chiral purity of the compound of Formula II is at least 98% ee (i.e., ratio of IIa to IIb is ≥99/1). More preferably, the chiral purity of the compound of Formula II is at least 99% ee (i.e., ratio of IIa to IIb is ≥99.5/0.5).

The compound of Formula II may be prepared using any suitable conditions, such as standard peptide coupling conditions well known to those of ordinary skill in the art, such as Schotten-Baumann conditions. For example, the compound of Formula II may be prepared by coupling a compound of formula $R^1C(=O)X'$, wherein X' is OH or a leaving group, with a compound of Formula IIc

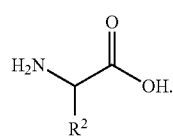

The leaving group X' is any group capable of nucleophilic displacement by the amino group of the compound of Formula IIc. In some embodiments, the moiety —C(O)—X' is an acid chloride or an activated ester, such as an O—(N-hydroxysuccinimide) ester. Preferably, the acid chloride or activated ester is generated in situ, such as by contacting an acid of formula $R^1C(=O)OH$ with a chloride donor such as thionyl chloride or oxalyl chloride, or by contacting an acid of formula $R^1C(=O)OH$, with a peptide coupling reagent. Examples of suitable peptide coupling reagents include, without limitation, carbodiimide reagents, e.g., dicyclohexylcarbodiimide (DCC) or 1-(3-dimethylaminopropyl)-3-ethylcarbodiimide (EDC); phosphonium reagents, e.g., benzotriazol-1-yloxytris(dimethylamino)phosphonium hexafluorophosphate (BOP reagent); and uronium reagents, e.g., O-(1H-benzotriazol-1-yl)-N,N,N',N'-tetramethyluronium tetrafluoroborate (TBTU) or 2-(7-aza-1H-benzotriazole-1-yl)-1,1,3,3-tetramethyluronium hexafluorophosphate (HATU). In some embodiments, the coupling reaction is carried out in the presence of a coupling agent and a base, such as an aqueous base, for example an aqueous carbonate solution such as aqueous potassium carbonate solution, or an amine base, for example, diisopropylethylamine, diethyl amine, NMM (N-methylmorpholine), DIPEA (N,N-diisopropylethylamine, Hunig's base), or a mixture thereof The coupling reaction is typically carried out in an organic solvent such as, for example, DMF (N,N-dimethylformamide), DMA (N,N-dimethylacetamide), toluene, dichloromethane, dichloroethane, or a mixture thereof.

The identities of $R^7$ and $R^8$ in the amine of Formula III are not critical. All that is required in the choice of $R^7$ and $R^8$ is that the

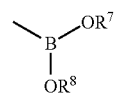

moiety of the amide of Formula IV be convertible into the

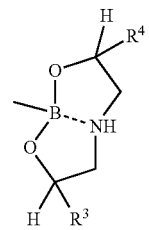

moiety of the boronic ester of Formula V during step (b). Therefore, essentially any combination of $R^7$ and $R^8$ can be used. Preferably, $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur. Preferably, $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, $R^7$ and $R^8$ are independently chosen from optionally substituted C$_{1-6}$alkyl, optionally substituted C$_{6-10}$aryl, optionally substituted C$_{7-16}$arylalkyl, optionally substituted C$_{3-11}$cycloalkyl, optionally substituted 3-15 membered heterocycloalkyl, optionally substituted 5-15 membered heteroaryl, and optionally substituted 6-21 membered heteroarylalkyl, or R$^7$ and R$^8$ together with the boron and oxygen atoms to which they are attached form an optionally substituted 5-10 membered carbon-containing ring having 0-2 additional heteroatoms chosen from nitrogen, oxygen and sulfur. Preferably, R$^7$ and R$^8$ are independently chosen from optionally substituted C$_{1-6}$alkyl, optionally substituted C$_{6-10}$aryl, optionally substituted C$_{7-16}$arylalkyl, optionally substituted C$_{3-11}$cycloalkyl, optionally substituted 3-15 membered heterocycloalkyl, optionally substituted 5-15 membered heteroaryl, and optionally substituted 6-21 membered heteroarylalkyl, or R$^7$ and R$^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, R$^7$ and R$^8$, together with the boron and oxygen atoms to which they are attached, form an optionally substituted 5-10 membered carbon-containing ring having 0-2 additional heteroatoms chosen from nitrogen, oxygen and sulfur. Preferably, R$^7$ and R$^8$, together with the boron and oxygen atoms to which they are attached, form a cyclic boronic ester having, in addition to the boron and oxygen atoms and without counting the hydrogen atoms, from 2 to 20 additional atoms chosen from carbon, nitrogen, oxygen and sulfur. In embodiments in which R$^7$ and R$^8$, together with the boron and oxygen atoms to which they are attached, form a cyclic boronic ester, it is preferred that 2-5 of the additional atoms are ring atoms. Preferably, no more than 2 of the additional ring atoms are N, O, or S atoms. Preferably, R$^7$ and R$^8$, together with the boron and oxygen atoms to which they are attached, form an optionally substituted 5-8 membered carbon-containing ring having 0-2 additional heteroatoms chosen from nitrogen, oxygen, and sulfur. Preferably, R$^7$ and R$^8$, together with the boron and oxygen atoms to which they are attached, form an optionally substituted 5-8 membered carbon-containing ring having 0-1 additional nitrogen atoms. Preferably, R$^7$ and R$^8$, together with the boron and oxygen atoms to which they are attached, form an optionally substituted 5-8 membered carbon-containing ring having 0-1 additional nitrogen atoms, wherein the ring atoms other than the boron atom are derived from a chiral diol such as 2,3-butanediol, preferably (2R,3R)-(−)-2,3-butanediol or (2S,3S)-(+)-2,3-butanediol; pinanediol, preferably (1R,2R,3R,5S)-(−)-pinanediol or (1S,2S,3S,5R)-(+)-pinanediol; 1,2-cyclopentanediol, preferably (1S,2S)-(+)-trans-1,2-cyclopentanediol or (1R,2R)-(−)-trans-1,2-cyclopentanediol; 2,5-hexanediol, preferably (2S,5S)-2,5-hexanediol or (2R,5R)-2,5-hexanediol; 1,2-dicyclohexyl-1,2-ethanediol, preferably (1R,2R)-1,2-dicyclohexyl-1,2-ethanediol or (1S,2S)-1,2-dicyclohexyl-1,2-ethanediol; hydrobenzoin, preferably (S,S)-(−)-hydrobenzoin or (R,R)-(+)-hydrobenzoin; 2,4-pentanediol, preferably (R,R)-(−)-2,4-pentanediol or (S,S,)-(+)-2,4-pentanediol; erythronic y-lactone, preferably D-erythronic y-lactone; or a carbohydrate, such as a 1,2,5,6-symmetrically protected mannitol. Preferably, R$^7$ and R$^8$, together with the boron and oxygen atoms to which they are attached, form an optionally substituted 5 membered carbon-containing ring, wherein the ring atoms other than the boron atom are derived from (1S,2S,3S,5R)-(+)-pinanediol (i.e., a compound of Formula III that is (1R)-1-[(3aS,4S,6S,7aR)-hexahydro-3a,5,5-trimethyl-4,6-methano-1,3,2-benzodioxaborol-2-yl]-3-methylbutylamine).

The amine of Formula III may be prepared by any suitable method. In certain embodiments, the amine of Formula III may be prepared from a corresponding protected amine of Formula IIIa

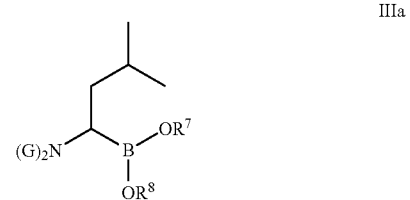

IIIa wherein G is an amine protecting group. In such embodiments, the protected amine of Formula IIIa is deprotected to form the amine of Formula III. The deprotection may be accomplished by any suitable method, such as by reacting the amine of Formula IIIa with an acid such as hydrochloric acid to form the corresponding acid salt of the amine of Formula IIIa. The acid salt is then converted to the amine of Formula III by neutralization with a base. Preferably, the latter neutralization step is performed in situ during coupling step (a) in the process of the present invention. Suitable amine protecting groups are well known to those of ordinary skill in the art (see, for example, Gross and Mienhoffer, eds., *The Peptides*, Vol. 3, Academic Press, New York, 1981, pp. 3-88; Green and Wuts, *Protective Groups in Organic Synthesis*, 3$^{rd}$ edition, John Wiley and Sons, Inc., New York, 1999). Silyl protecting groups are particularly suited for generating the amine of Formula III in situ. Preferably, G is a silyl protecting group of formula (R)$_3$Si—, wherein each R is independently chosen from alkyl, arylalkyl, and aryl, where the aryl and/or the aryl portion of the arylalkyl is optionally substituted. Preferably, each G is a trimethylsilyl protecting group ((CH$_3$)$_3$Si—). The amines of Formula III or Formula IIIa may be prepared by any suitable method, including the methods disclosed in U.S. Pat. No. 7,576,206 and U.S. Patent Application Publication No. 2005/0240047. A preferred amine of Formula III for use in the present invention is (1R)-1-[(3aS,4S,6S,7aR)-hexahydro-3a,5,5-trimethyl-4,6-methano-1,3,2-benzodioxaborol-2-yl]-3-methylbutylamine. A preferred amine of Formula IIIa for use in the present invention is N,N-bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine. Preferably, (1R)-1-[(3aS,4S,6S,7aR)-hexahydro-3a,5,5-trimethyl-4,6-methano-1,3,2-benzodioxaborol-2-yl]-3-methylbutylamine is formed in situ in coupling step (a) of the present invention from N,N-bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine.

The amine of Formula III contains a stereogenic center at the carbon to which the boron atom is attached. Therefore, two isomers of the amine of Formula III are possible (IIIb and IIIc):

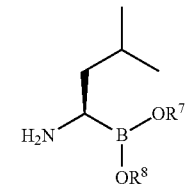

IIIb

23
-continued

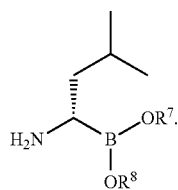

The isomer of Formula IIIb contains the desired stereochemistry present in the boronic ester of Formula I. Therefore, the amine of Formula III must contain at least some of the isomer of Formula IIIb. An advantage of the present invention is that the boronic ester of Formula I is obtained with very high chiral purity even if the amine of Formula III contains a significant quantity of the isomer of Formula IIIc. Although the chiral purity of the amine of Formula III is not critical, it is preferred that the chiral purity of the amine of Formula III is at least 0% ee (i.e., ratio of IIIb to IIIc is ≥50/50 (racemic)). More preferably, the chiral purity of the amine of Formula III is at least 50% ee (i.e., ratio of IIIb to IIIc is ≥75/25). More preferably, the chiral purity of the amine of Formula III is at least 70% ee (i.e., ratio of IIIb to IIIc is ≥85/15). More preferably, the chiral purity of the amine of Formula III is at least 80% ee (i.e., ratio of IIIb to IIIc is ≥90/10). More preferably, the chiral purity of the amine of Formula III is at least 90% ee (i.e., ratio of IIIb to IIIc is ≥95/5). More preferably, the chiral purity of the amine of Formula III is at least 94% ee (i.e., ratio of IIIb to IIIc is ≥97/3). More preferably, the chiral purity of the amine of Formula III is at least 98% ee (i.e., ratio of IIIb to IIIc is ≥99/1). More preferably, the chiral purity of the amine of Formula III is at least 99% ee (i.e., ratio of IIIb to IIIc is ≥99.5/0.5).

In embodiments in which $R^7$ and $R^8$, together with the boron and oxygen atoms to which they are attached, form an 8 membered ring in which the ring atoms other than boron are derived from diethanolamine or diisopropanolamine, then the amide of Formula IV is the same as the boronic ester of Formula V and it is not necessary to perform step (b) in the process of the present invention. In such embodiments, the present invention provides a process for preparing a boronic ester of Formula I

I

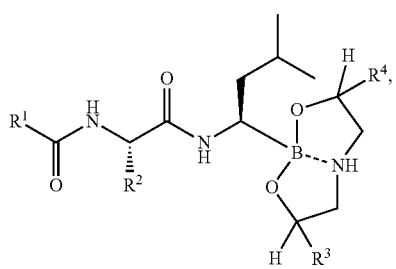

24 wherein
$R^1$ is 2-(6-phenyl)pyridinyl and $R^2$ is (1R)-1-hydroxyethyl, or $R^1$ is 2-pyrazinyl and
$R^2$ is benzyl; and
$R^3$ and $R^4$ are H, or $R^3$ and $R^4$ are methyl;
comprising the steps of:
(a) preparing a boronic ester of Formula V

V

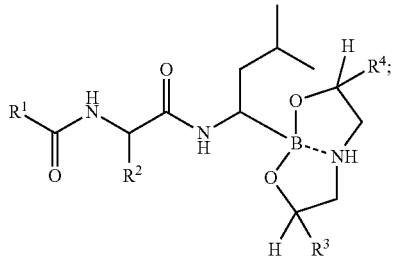

and
(b) crystallizing the boronic ester of Formula I from a solution of the boronic ester of Formula V.

In embodiments in which $R^2$ and $R^8$, together with the boron and oxygen atoms to which they are attached, do not form an 8 membered ring in which the ring atoms other than boron are derived from diethanolamine or diisopropanolamine, the amide of Formula IV is different from the boronic ester of Formula V, and it is therefore necessary to convert the amide of Formula IV into the boronic ester of Formula V in step (b) of the process of the present invention. The amide of Formula IV can be converted into the boronic ester of Formula V in step (b) using esterification conditions well known to those of ordinary skill in the art. In certain embodiments, the amide of Formula IV is directly reacted with diethanolamine ($R^3$, $R^4$, =H) or diisopropanolamine ($R^3$, $R^4$=methyl). Optionally, this direct reaction is conducted in the presence of an acid catalyst. Suitable acid catalysts include, but are not limited to, inorganic acids such as hydrochloric, hydrobromic, sulfuric, sulfamic, phosphoric, nitric and the like, and organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. A preferred acid is methanesulfonic acid. Preferably, the direct reaction is performed with diethanolamine.

The amide of Formula IV also may be indirectly converted to the boronic ester of Formula V by first converting the amide of Formula IV to the corresponding free boronic acid (i.e., $R^7$, $R^8$=H) and then converting the free boronic acid to the boronic ester of Formula V. Preferably, the free boronic acid is prepared in situ and reacted with diethanolamine ($R^3$, $R^4$=H) or diisopropanolamine ($R^3$, $R^4$=methyl) to provide the boronic ester of Formula V. Preferably, the free boronic acid is prepared by transesterification of a boronic ester of Formula IV ($R^7$, $R^8$≠H) with a $C_1$-$C_6$alkylboronic acid, such as 2-methylpropylboronic acid. Preferably, this transesterification reaction is conducted in the presence of an acid catalyst. Suitable acid catalysts include, but are not limited to the mineral acids and organic acids mentioned above. Mineral acids are preferred. A preferred mineral acid is hydrochloric acid. In certain embodiments, the transesterification reaction is conducted using biphasic conditions such that the free boronic acid of Formula IV and the $C_1$-$C_6$alkylboronic acid ester reaction products are phase separated. Suitable solvents for the biphasic reaction include methanol/heptane, with the free boronic acid being present in the methanol layer, and the $C_1$-$C_6$alkylboronic acid ester present in the heptane layer. The free boronic acid of Formula IV ($R^7$, $R^8$=H) is then separated, neutralized, transferred to a suitable solvent (e.g., ethyl acetate or another solvent for step (c)), and reacted with diethanolamine or diisopropanolamine to provide the boronic ester of Formula V.

In step (c), the boronic ester of Formula I is crystallized from a solution of the boronic ester of Formula V. Any suitable solvent can be used for the crystallization. Suitable solvents include, but are not limited to, ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, water, and mixtures thereof. Ethanol, ethyl acetate, n-propanol, isopropanol, and methyl tert-butyl ether are preferred. Particularly preferred are ethanol, n-propanol, and isopropanol. Also useful are mixtures of an organic solvent and water, with ethanol/water being preferred. When water is used, it is preferably used as an antisolvent to help precipitate the boronic ester of Formula I, rather than as a co-solvent in the initial solubilization. Suitable crystallization methods are well known to those of ordinary skill in the art. Suitable crystallization methods include, but are not limited to, concentrating (e.g., by heating to remove solvent), cooling, precipitating with an antisolvent, seeding, and/or slurrying the solution. Cooling is preferred. The crystalline boronic ester of Formula I can be isolated by any suitable method, such as filtration, decantation, or centrifugation. Filtration is preferred.

In preferred embodiments, the crystallization solution used in step (c) is the reaction mixture resulting from step (b), and the boronic ester of Formula I simply crystallizes from the step (b) reaction mixture. This is unexpected and highly advantageous because most amides of Formula IV (particularly those in which $R^1$ is 2-(6-phenyl)pyridinyl and $R^2$ is (1R)-1-hydroxyethyl) are not crystalline as their free boronic acids (e.g., Compound 1). Therefore, purification of these compounds can typically only be accomplished using some form of chromatography, which is time consuming, expensive, and limited in terms of the ultimate purity obtainable. Even more unexpectedly and advantageously, the boronic ester of Formula I having the desired stereochemistry at all positions is the isomer that preferentially crystallizes from the mixture of diastereomers of Formula V. This is an important aspect of the present invention because chemical and chiral purification is accomplished by simple crystallization, and the obtained crystalline boronic ester of Formula I is readily converted to the free boronic acid of Formula IA (i.e., Compound 1 ($R^1$=2-(6-phenyl)pyridinyl, $R^2$=(1R)-1-hydroxyethyl) or bortezomib ($R^1$ is 2-pyrazinyl and $R^2$ is benzyl)) without diminishing chemical or diastereomeric purity.

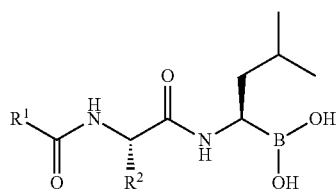

IA

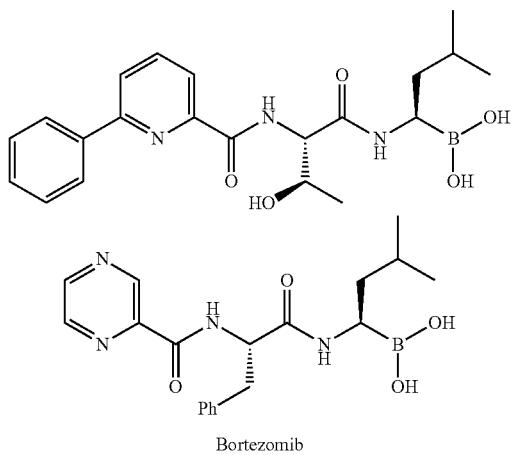

Compound 1

Bortezomib

In preferred embodiments, the boronic ester of Formula I is converted to the corresponding boronic acid of Formula IA. Thus, in one aspect the present invention provides a process for preparing a boronic acid of Formula IA

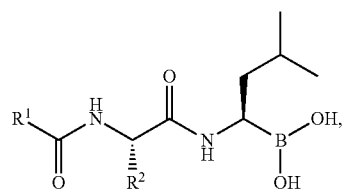

IA wherein
$R^1$ is 2-(6-phenyl)pyridinyl and $R^2$ is (1R)-1-hydroxyethyl, or $R^1$ is 2-pyrazinyl and
$R^2$ is benzyl;
comprising the steps of:
(a) preparing an amide of Formula IV

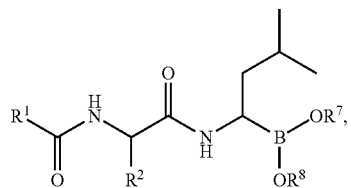

IV wherein
$R^2$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
or $R^2$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula V

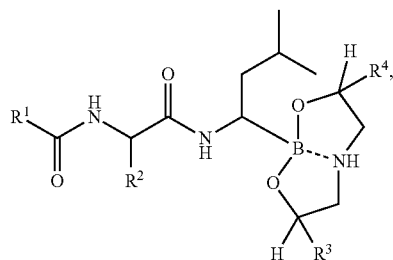

V wherein $R^3$ and $R^4$ are H; or $R^3$ and $R^4$ are methyl;

(c) crystallizing the boronic ester of Formula I from a solution of the boronic ester of Formula V

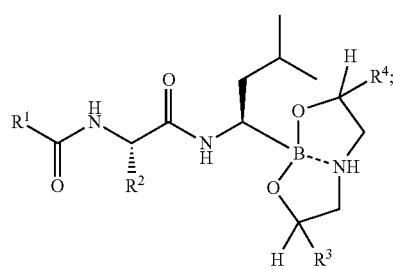

I and (d) converting the boronic ester of Formula I into the boronic acid of Formula IA.

In this aspect, of the invention, when $R^7$ and $R^8$, together with the boron and oxygen atoms to which they are attached, form an 8 membered ring in which the ring atoms other than boron are derived from diethanolamine or diisopropanolamine, then the amide of Formula IV is the same as the boronic ester of Formula V and the invention provides a process for preparing a boronic acid of Formula IA

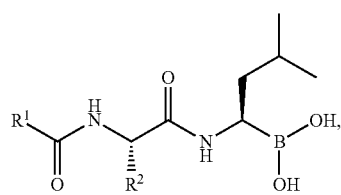

IA wherein $R^1$ is 2-(6-phenyl)pyridinyl and $R^2$ is (1R)-1-hydroxyethyl, or $R^1$ is 2-pyrazinyl and $R^2$ is benzyl;

comprising the steps of:

(a) preparing a boronic ester of Formula V

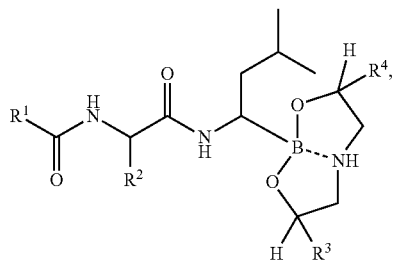

V wherein $R^3$ and $R^4$ are H; or $R^3$ and $R^4$ are methyl;

(b) crystallizing the boronic ester of Formula I from a solution of the boronic ester of Formula V

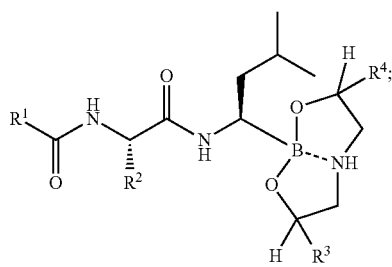

I (c) converting the boronic ester of Formula I into the boronic acid of Formula IA.

And in a preferred embodiment, the invention provides a process for preparing a boronic acid of Formula IA

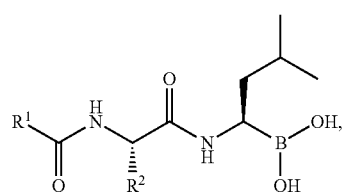

IA wherein

R¹ is 2-(6-phenyl)pyridinyl and R² is (1R)-1-hydroxyethyl, or R¹ is 2-pyrazinyl and R² is benzyl;

comprising the steps of:

(a) coupling a compound of Formula II

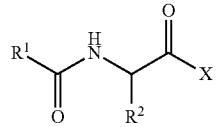

with an amine of Formula III

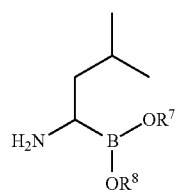

to form an amide of Formula IV

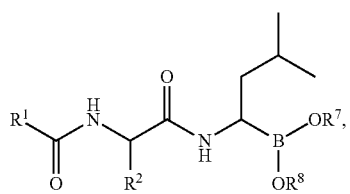

wherein

X is OH or a leaving group; and

R⁷ and R⁸ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or R⁷ and R⁸, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula V

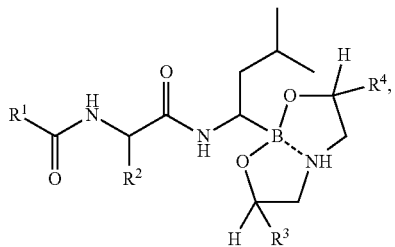

wherein R³ and R⁴ are H; or R³ and R⁴ are methyl;

(c) crystallizing the boronic ester of Formula I from a solution of the boronic ester of Formula V

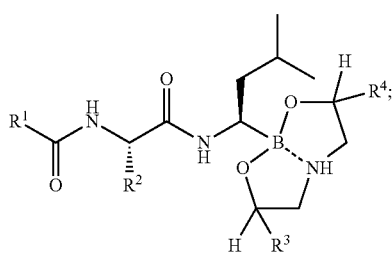

and (d) converting the boronic ester of Formula I into the boronic acid of Formula IA.

The most important step in the process is crystallization step (c), because the crystallization step provides extremely pure material rapidly and conveniently. Thus, in another aspect, the present invention provides a process for preparing a boronic acid of Formula IA

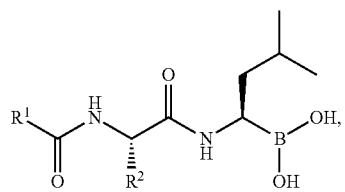

wherein

R¹ is 2-(6-phenyl)pyridinyl and R² is (1R)-1-hydroxyethyl, or R¹ is 2-pyrazinyl and R² is benzyl;

comprising the steps of (a) crystallizing a boronic ester of Formula I from a solution of a boronic ester of Formula V

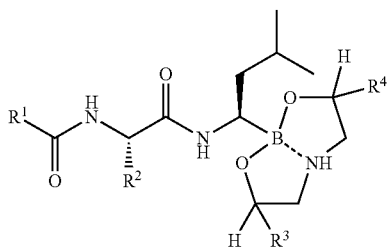

I

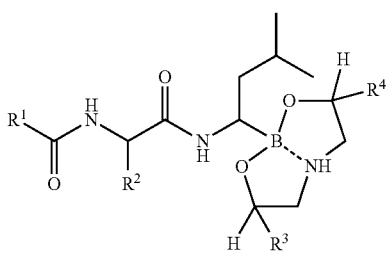

V wherein $R^3$ and $R^4$ are H; or $R^3$ and $R^4$ are methyl; and
(b) converting the boronic ester of Formula I into the boronic acid of Formula IA.

In one embodiment, $R^1$ is 2-(6-phenyl)pyridinyl, $R^2$ is (1R)-1-hydroxyethyl, and $R^3$ and $R^4$ are H. In another embodiment, $R^1$ is 2-(6-phenyl)pyridinyl, $R^2$ is (1R)-1-hydroxyethyl, and $R^3$ and $R^4$ are methyl. In another embodiment, $R^1$ is 2-pyrazinyl, $R^2$ is benzyl, and $R^3$ and $R^4$ are H.

The boronic ester of Formula I can be converted to the boronic acid of Formula IA using any suitable method. For example, the boronic ester of Formula I can be simply be exposed to water, preferably in the presence of an acid catalyst, to prepare the free boronic acid of Formula IA. Optionally, the hydrolysis may be carried out in the presence of an organic solvent, for example, ethyl acetate, methanol, or methyl t-butyl ether. Acid catalysts include mineral acids, for example, hydrochloric acid, hydrobromic acid, phosphoric acid, nitric acid, and the like. Preferably, the acid is aqueous hydrochloric acid. Therefore, the present invention provides a simple process to obtain Compound 1 and bortezomib in high chemical and chiral purity even if the chiral purity of the amine of Formula III is low. This represents a significant improvement over the prior art synthetic methods, which produce Compound 1 and bortezomib having substantially the same chiral purity as that of the chiral pinanediol derivative starting material. Furthermore, the method of the present invention is advantageous because it proceeds in high overall yield (about 50%) from commercially available reagents and the intermediates produced are crystalline, easy to handle, and are obtained in high chemical purity and chiral purity by crystallization alone, without the need to perform any other purification method.

The chemical and chiral purity of the boronic ester of Formula I obtained in the crystallization step is often sufficiently high, such that the free boronic acid of Formula IA (i.e., Compound 1 or bortezomib) obtained in the conversion step may be directly used in pharmaceutical preparations without further purification. Preferably, the boronic ester of Formula I obtained in the crystallization step has a chemical purity of at least 90%. More preferably, the boronic ester of Formula I obtained in the crystallization step has a chemical purity of at least 95%. More preferably, the boronic ester of Formula I obtained in the crystallization step has a chemical purity of at least 97%. More preferably, the boronic ester of Formula I obtained in the crystallization step has a chemical purity of at least 98%. More preferably, the boronic ester of Formula I obtained in the crystallization step has a chemical purity of at least 98.5%. More preferably, the boronic ester of Formula I obtained in the crystallization step has a chemical purity of at least 99%. More preferably, the boronic ester of Formula I obtained in the crystallization step has a chemical purity of at least 99.2%. More preferably, the boronic ester of Formula I obtained in the crystallization step has a chemical purity of at least 99.3%. More preferably, the boronic ester of Formula I obtained in the crystallization step has a chemical purity of at least 99.5%. Preferably, the boronic ester of Formula I obtained in the crystallization step has a chiral purity of at least 90% de. Preferably, the boronic ester of Formula I obtained in the crystallization step has a chiral purity of at least 92% de. More preferably, the boronic ester of Formula I obtained in the crystallization step has a chiral purity of at least 95% de. More preferably, the boronic ester of Formula I obtained in the crystallization step has a chiral purity of at least 97% de. More preferably, the boronic ester of Formula I obtained in the crystallization step has a chiral purity of at least 98% de. More preferably, the boronic ester of Formula I obtained in the crystallization step has a chiral purity of at least 98.5% de. More preferably, the boronic ester of Formula I obtained in the crystallization step has a chiral purity of at least 99% de. More preferably, the boronic ester of Formula I obtained in the crystallization step has a chiral purity of at least 99.3% de. More preferably, the boronic ester of Formula I obtained in the crystallization step has a chiral purity of at least 99.5% de. More preferably, the boronic ester of Formula I obtained in the crystallization step has a chiral purity of at least 99.7% de. More preferably, the boronic ester of Formula I obtained in the crystallization step has a chiral purity of at least 99.8% de.

Optionally, the boronic ester of Formula I obtained in the crystallization step may be recrystallized to increase its chemical and/or chiral purity. Recrystallization techniques and conditions are known in the art and suitable conditions can be identified without undue experimentation. Suitable recrystallization solvents include, but are not limited to, ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, water, and mixtures thereof. Ethanol, ethyl acetate, n-propanol, isopropanol, and methyl tert-butyl ether are preferred. Particularly preferred are ethanol, n-propanol, and isopropanol. Also useful are mixtures of an organic solvent and water, with ethanol/water being preferred. When water is used, it is preferably used as an antisolvent to help precipitate the boronic ester of Formula I, rather than as a co-solvent in the initial solubilization. An exemplary recrystallization comprises suspension of the boronic ester of Formula I in aqueous $C_1$-$C_6$ alcohol, for example ethanol. The suspension can be heated, e.g., to a temperature at or near the boiling point, preferably about 75° C., for a time sufficient to dissolve impurities. The suspension is then cooled, e.g., to about 10° C. or lower, preferably about 2° C. to about 6° C., to induce crystallization of the boronic ester of Formula I. Water may be added to induce further precipitation. The crystalline boronic ester of Formula I can be isolated by any suitable method, such as filtration, decantation, or centrifugation. Filtration is preferred.

After recrystallization, the boronic ester of Formula I may be converted to the boronic acid of Formula IA (i.e., Compound 1 or bortezomib) as previously described. Preferably, the recrystallized boronic ester of Formula I has a chemical purity of at least 95%. More preferably, the recrystallized boronic ester of Formula I has a chemical purity of at least 97%. More preferably, the recrystallized boronic ester of Formula I has a chemical purity of at least 98%. More preferably, the recrystallized boronic ester of Formula I has a chemical purity of at least 98.5%. More preferably, the recrystallized boronic ester of Formula I has a chemical purity of at least 99%. More preferably, the recrystallized boronic ester of Formula I has a chemical purity of at least 99.3%. More preferably, the recrystallized boronic ester of Formula I has a chemical purity of at least 99.5%. More preferably, the recrystallized boronic ester of Formula I has a chemical purity of at least 99.7%. More preferably, the recrystallized boronic ester of Formula I has a chemical purity of at least 99.8%. More preferably, the recrystallized boronic ester of Formula I has a chemical purity of at least 99.9%. Preferably, the recrystallized boronic ester of Formula I has a chiral purity of at least 95% de. More preferably, the recrystallized boronic ester of Formula I has a chiral purity of at least 97% de. More preferably, the recrystallized boronic ester of Formula I has a chiral purity of at least 98% de. More preferably, the recrystallized boronic ester of Formula I has a chiral purity of at least 98.5% de. More preferably, the recrystallized boronic ester of Formula I has a chiral purity of at least 99% de. More preferably, the recrystallized boronic ester of Formula I has a chiral purity of at least 99.3% de. More preferably, the recrystallized boronic ester of Formula I has a chiral purity of at least 99.5% de. More preferably, the recrystallized boronic ester of Formula I has a chiral purity of at least 99.7% de. More preferably, the recrystallized boronic ester of Formula I has a chiral purity of at least 99.8% de. More preferably, the recrystallized boronic ester of Formula I has a chiral purity of at least 99.9% de.

Processes for Purification

Process 1

In view of the remarkable improvement in purification and handling afforded by the preparation process of the present invention, the invention further provides a process for purifying a compound of Formula VI

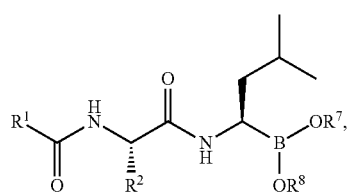

VI wherein $R^1$ is 2-(6-phenyl)pyridinyl and $R^2$ is (1R)-1-hydroxyethyl, or $R^1$ is 2-pyrazinyl and $R^2$ is benzyl, and $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur;

comprising the steps of:

(a) if the compound of Formula VI is not a boronic ester of Formula VII, converting the compound of Formula VI into the boronic ester of Formula VII

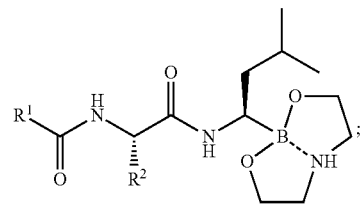

VII (b) crystallizing the boronic ester of Formula VII from solution;

(c) isolating the crystallized boronic ester of Formula VII from the solution; and (d) if the isolated boronic ester of Formula VII is not the compound of Formula VI, converting the isolated boronic ester of Formula VII back into the compound of Formula VI.

$R^1$ and $R^2$ are as previously defined for the preparation process of the present invention. In one embodiment of the purification process, $R^1$ is 2-(6-phenyl)pyridinyl and $R^2$ is (1R)-1-hydroxyethyl. In another embodiment, $R^1$ is 2-pyrazinyl and $R^2$ is benzyl.

$R^7$ and $R^8$ are as previously defined for the preparation process of the present invention, except that H is also a possibility. As before, the identities of $R^7$ and $R^8$ are not critical in the purification process of the present invention. All that is required in the choice of $R^7$ and $R^8$ is that the

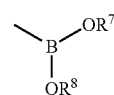

moiety of the compound of Formula VI be convertible into the

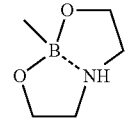

moiety of the boronic ester of Formula VII during step (a) of the purification process. Therefore, essentially any combination of $R^7$ and $R^8$ can be used. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted 3-15 membered heterocycloalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted 3-15 membered heterocycloalkyl, optionally substituted 5-15 membered heteroaryl, and optionally substituted 6-21 membered heteroarylalkyl, or $R^7$ and $R^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, $R^7$ and $R^8$ are H, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur. Preferably, $R^7$ and $R^8$ are H, or $R^7$ and $R^8$, together with the boron and oxygen atoms to which they are attached, form a cyclic boronic ester having, in addition to the boron and oxygen atoms and without counting the hydrogen atoms, from 2 to 20 additional atoms chosen from carbon, nitrogen, oxygen and sulfur. In embodiments in which $R^7$ and $R^8$, together with the boron and oxygen atoms to which they are attached, form a cyclic boronic ester, it is preferred that 2-5 of the additional atoms are ring atoms. Preferably, no more than 2 of the additional ring atoms are N, O, or S atoms. Preferably, $R^7$ and $R^8$ are H, or $R^7$ and $R^8$, together with the boron and oxygen atoms to which they are attached, form an optionally substituted 5-8 membered carbon-containing ring having 0-2 additional heteroatoms chosen from nitrogen, oxygen, and sulfur. Preferably, $R^7$ and $R^8$ are H, or $R^7$ and $R^8$, together with the boron and oxygen atoms to which they are attached, form an optionally substituted 5-8 membered carbon-containing ring having 0-1 additional nitrogen atoms. Preferably, $R^7$ and $R^8$ are H, or $R^7$ and $R^8$, together with the boron and oxygen atoms to which they are attached, form an optionally substituted 5-8 membered carbon-containing ring having 0-1 additional nitrogen atoms, wherein the ring atoms other than the boron atom are derived from a chiral diol such as 2,3-butanediol, preferably (2R,3R)-(−)-2,3-butanediol or (2S,3S)-(+)-2,3-butanediol; pinanediol, preferably (1R,2R,3R,5S)-(−)-pinanediol or (1S,2S,3S,5R)-(+)-pinanediol; 1,2-cyclopentanediol, preferably (1S,2S)-(+)-trans-1,2-cyclopentanediol or (1R,2R)-(−)-trans-1,2-cyclopentanediol; 2,5-hexanediol, preferably (2S,5S)-2,5-hexanediol or (2R,5R)-2,5-hexanediol; 1,2-dicyclohexyl-1,2-ethanediol, preferably (1R,2R)-1,2-dicyclohexyl-1,2-ethanediol or (1S,2S)-1,2-dicyclohexyl-1,2-ethanediol; hydrobenzoin, preferably (S,S)-(−)-hydrobenzoin or (R,R)-(+)-hydrobenzoin; 2,4-pentanediol, preferably (R,R)-(−)-2,4-pentanediol or (S,S,)-(+)-2,4-pentanediol; erythronic γ-lactone, preferably D-erythronic γ-lactone; or a carbohydrate, such as a 1,2,5,6-symmetrically protected mannitol. Preferably, $R^7$ and $R^8$ are H, or $R^7$ and $R^8$, together with the boron and oxygen atoms to which they are attached, form an optionally substituted 5 membered carbon-containing ring, wherein the ring atoms other than the boron atom are derived from (1S,2S,3S,5R)-(+)-pinanediol. In preferred embodiments, $R^7$ and $R^8$ are H. In such embodiments, the invention provides a process for purifying Compound 1 or bortezomib.

If necessary, step (a) of the purification process can be performed as described above for step (b) of the preparation process. In embodiments in which $R^7$ and $R^8$, together with the boron and oxygen atoms to which they are attached, form an 8 membered ring in which the ring atoms other than boron are derived from diethanolamine, then the compound of Formula VI is the same as the boronic ester of Formula VII and it is not necessary to perform step (a) in the purification process of the present invention. In all other embodiments, the compound of Formula VI is different from the boronic ester of Formula VII, and it is therefore necessary to convert the compound of Formula VI into the boronic ester of Formula VII in step (a) of the purification process. The compound of Formula VI can be converted into the boronic ester of Formula VII in step (a) using esterification conditions well known to those of ordinary skill in the art. In certain embodiments, the compound of Formula VI is directly reacted with diethanolamine Optionally, this direct reaction is conducted in the presence of an acid catalyst. Suitable acid catalysts include, but are not limited to, inorganic acids such as hydrochloric, hydrobromic, sulfuric, sulfamic, phosphoric, nitric and the like, and organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. A preferred acid is methanesulfonic acid.

The compound of Formula VI also may be indirectly converted to the boronic ester of Formula VII by first converting the compound of Formula VI (when $R^7$ and $R^8$ are not already H) to the corresponding free boronic acid (i.e., Formula IA) and then converting the boronic acid of Formula IA to the boronic ester of Formula VII. Preferably, the boronic acid of Formula IA is prepared in situ and reacted with diethanolamine to provide the boronic ester of Formula VII. Preferably, the boronic acid of Formula IA is prepared by transesterification of a boronic ester of Formula VI ($R^7$, $R^8 \neq H$) with a $C_1$-$C_6$alkylboronic acid, such as 2-methylpropylboronic acid. Preferably, this transesterification reaction is conducted in the presence of an acid catalyst. Suitable acid catalysts include, but are not limited to, the mineral acids and organic acids mentioned above. Mineral acids are preferred. A preferred mineral acid is hydrochloric acid. In certain embodiments, the transesterification reaction is conducted using biphasic conditions such that the boronic acid of Formula IA and the $C_1$-$C_6$alkylboronic acid ester reaction products are phase separated. Suitable solvents for the biphasic reaction include methanol/heptane, with the boronic acid of Formula IA being present in the methanol layer, and the $C_1$-$C_6$alkylboronic acid ester present in the heptane layer. The boronic acid of Formula IA is then separated and reacted with diethanolamine to provide the boronic ester of Formula VII.

In step (b) of the purification process, the boronic ester of Formula VII is crystallized from solution. Any suitable solvent can be used for the crystallization. Suitable solvents include, but are not limited to, ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, water, and mixtures thereof. Ethanol, ethyl acetate, n-propanol, isopropanol, and methyl tert-butyl ether are preferred. Particularly preferred are ethanol, n-propanol, and isopropanol. Also useful are mixtures of an organic solvent and water, with ethanol/water being preferred. When water is used, it is preferably used as an antisolvent to help precipitate the boronic ester of Formula I, rather than as a co-solvent in the initial solubilization. Suitable crystallization methods are well known to those of ordinary skill in the art. Suitable crystallization methods include, but are not limited to, concentrating (e.g., by heating to remove solvent), cooling, precipitating with an antisolvent, seeding, and/or slurrying the solution. Cooling is preferred.

Crystallization step (b) is extremely important to the purification process because it permits substantial upgrades in chemical and chiral purity by simple crystallization alone, without the need to perform more problematic purification methods such as chromatography. It is made possible because the boronic ester of Formula VII is stable and crystalline, and unexpectedly crystallizes from solution in distinct preference to its corresponding diastereomers. These desirable stability, handling, and purification attributes are particularly surprising because esters of Formula VI are often difficult to form, difficult to purify, unstable, and/or non-crystalline. These surprising properties of the boronic ester of Formula VII, which permit its ready handling, long-term storage, and high purity, are especially advantageous because the boronic ester of Formula VII is readily converted to Compound 1 or bortezomib having the same high chemical and chiral purity.

In step (c) of the purification process, the crystalline boronic ester of Formula VII can be isolated by any suitable method, such as filtration, decantation, or centrifugation. Filtration is preferred.

In step (d) of the purification process, the isolated boronic ester of Formula VII is converted back into the compound of Formula VI, if necessary. In embodiments in which $R^7$ and $R^8$, together with the boron and oxygen atoms to which they are attached, form an 8 membered ring in which the ring atoms other than boron are derived from diethanolamine, then the boronic ester of Formula VII is the same as the compound of Formula VI, and it is not necessary to perform step (d) in the purification process of the present invention. In all other embodiments, the boronic ester of Formula VII is different from the compound of Formula VI, and it is therefore necessary to convert the boronic ester of Formula VII back into the compound of Formula VI in step (d) of the purification process. When $R^7$ and $R^8 \neq H$, the boronic ester of Formula VII can be converted into a compound of Formula VI using the direct or indirect transesterification reactions described above for step (a). When $R^7$ and $R^8$ are H, the boronic ester of Formula VII can be converted to the boronic acid of Formula IA as previously described. For example, the boronic ester of Formula VII can be simply be exposed to water, preferably in the presence of an acid catalyst, to prepare the boronic acid of Formula IA. Generally, the hydrolysis is carried out in an organic solvent, for example, ethyl acetate, methanol, or methyl t-butyl ether in the presence of an acid catalyst. Typically, the acid is a mineral acid, for example, hydrochloric acid, hydrobromic acid, phosphoric acid, nitric acid, and the like. Preferably, the acid is aqueous hydrochloric acid.

The chemical and chiral purity of the compound of Formula VI obtained from the purification process is often sufficiently high, such that the compound of Formula VI can be directly used in pharmaceutical preparations. Preferably, the compound of Formula VI has a chemical purity of at least 90%. More preferably, the compound of Formula VI has a chemical purity of at least 95%. More preferably, the compound of Formula VI has a chemical purity of at least 97%. More preferably, the compound of Formula VI has a chemical purity of at least 98%. More preferably, the compound of Formula VI has a chemical purity of at least 98.5%. More preferably, the compound of Formula VI has a chemical purity of at least 99%. More preferably, the compound of Formula VI has a chemical purity of at least 99.5%. Preferably, the compound of Formula VI has a chiral purity of at least 90% de. Preferably, the compound of Formula VI has a chiral purity of at least 92% de. More preferably, the compound of Formula VI has a chiral purity of at least 95% de. More preferably, the compound of Formula VI has a chiral purity of at least 97% de. More preferably, the compound of Formula VI has a chiral purity of at least 98% de. More preferably, the compound of Formula VI has a chiral purity of at least 98.5% de. More preferably, the compound of Formula VI has a chiral purity of at least 99% de. More preferably, the compound of Formula VI has a chiral purity of at least 99.2% de. More preferably, the compound of Formula VI has a chiral purity of at least 99.3% de. More preferably, the compound of Formula VI has a chiral purity of at least 99.5% de. More preferably, the compound of Formula VI has a chiral purity of at least 99.7% de. More preferably, the compound of Formula VI has a chiral purity of at least 99.8% de.

Optionally, the isolated boronic ester of Formula VII may be recrystallized prior to converting it back into the compound of Formula VI to increase its chemical and/or chiral purity. Recrystallization techniques and conditions are known in the art and suitable conditions can be identified without undue experimentation. Suitable recrystallization solvents include, but are not limited to, organic solvents such as ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, and mixtures thereof Also suitable are mixtures of water with organic solvents, such as the organic solvents previously mentioned, with ethanol/water being a preferred example. When water is used, it is preferably used as an antisolvent to help precipitate the boronic ester of Formula I, rather than as a co-solvent in the initial solubilization. Ethanol, ethyl acetate, n-propanol, isopropanol, and methyl tert-butyl ether are preferred recrystallization solvents. Particularly preferred are ethanol, n-propanol, and isopropanol. The crystalline boronic ester of Formula VII can be isolated by any suitable method, such as filtration, decantation, or centrifugation. Filtration is preferred.

Preferably, the recrystallized boronic ester of Formula VII has a chemical purity of at least 95%. More preferably, the recrystallized boronic ester of Formula VII has a chemical purity of at least 97%. More preferably, the recrystallized boronic ester of Formula VII has a chemical purity of at least 98%. More preferably, the recrystallized boronic ester of Formula VII has a chemical purity of at least 98.5%. More preferably, the recrystallized boronic ester of Formula VII has a chemical purity of at least 99%. More preferably, the recrystallized boronic ester of Formula VII has a chemical purity of at least 99.5%. More preferably, the recrystallized boronic ester of Formula VII has a chemical purity of at least 99.8%. More preferably, the recrystallized boronic ester of Formula VII has a chemical purity of at least 99.9%. Preferably, the recrystallized boronic ester of Formula VII has a chiral purity of at least 95% de. More preferably, the recrystallized boronic ester of Formula VII has a chiral purity of at least 97% de. More preferably, the recrystallized boronic ester of Formula VII has a chiral purity of at least 98% de. More preferably, the recrystallized boronic ester of Formula VII has a chiral purity of at least 98.5% de. More preferably, the recrystallized boronic ester of Formula VII has a chiral purity of at least 99% de. More preferably, the recrystallized boronic ester of Formula VII has a chiral purity of at least 99.5% de. More preferably, the recrystallized boronic ester of Formula VII has a chiral purity of at least 99.8% de. More preferably, the recrystallized boronic ester of Formula VII has a chiral purity of at least 99.9% de.

After recrystallization, the boronic ester of Formula VII may, if necessary, be converted in step (d) to the compound of Formula VI having the same high chemical and chiral purity as the recrystallized boronic ester of Formula VII using the techniques described above.

Process 2

The invention further provides a process for purifying a compound of Formula VIII

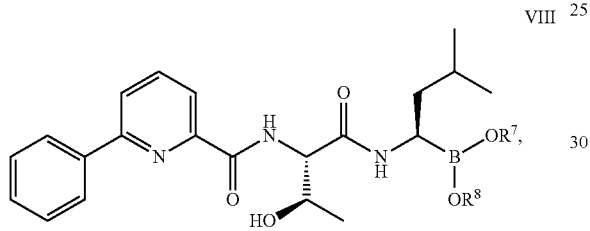

VIII wherein $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur;

comprising the steps of:

(a) if the compound of Formula VIII is not a boronic ester of Formula IX, converting the compound of Formula VIII into the boronic ester of Formula IX

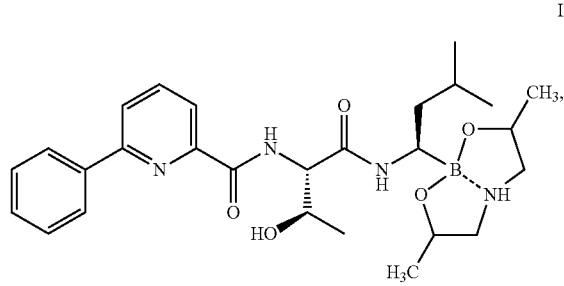

IX (b) crystallizing the boronic ester of Formula IX from solution;
(c) isolating the crystallized boronic ester of Formula IX from the solution; and
(d) if the isolated boronic ester of Formula IX is not the compound of Formula VIII, converting the isolated boronic ester of Formula IX back into the compound of Formula VIII.

The process for purifying a compound of Formula VIII is very similar to the process for purifying a compound of Formula VI described above. For example, $R^7$ and $R^8$ are as previously defined for the process for purifying a compound of Formula VI, except that the choice of $R^7$ and $R^8$ is limited only by the ability to convert the

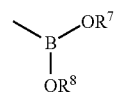

moiety of the compound of Formula VIII into the

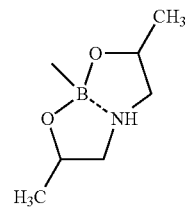

moiety of the boronic ester of Formula IX during step (a) of the purification process. Therefore, essentially any combination of $R^7$ and $R^8$ can be used. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted 3-15 membered heterocycloalkyl, optionally substituted 5-15 membered heteroaryl, and optionally substituted 6-21 membered heteroarylalkyl, or $R^7$ and $R^8$ together with the boron and oxygen atoms to which they are attached form an optionally substituted 5-10 membered carbon-containing ring having 0-2 additional heteroatoms chosen from nitrogen, oxygen and sulfur. Preferably, $R^7$ and $R^8$ are independently chosen from H, optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted 3-15 membered heterocycloalkyl, optionally substituted 5-15 membered heteroaryl, and optionally substituted 6-21 membered heteroarylalkyl, or $R^7$ and $R^8$ together with the boron and oxygen atoms to which they are attached form a cyclic boronic ester having, in addition to the boron and oxygen atoms and without counting the hydrogen atoms, from 2 to 20 additional atoms chosen from carbon, nitrogen, oxygen and sulfur. Preferably, $R^7$ and $R^8$ are H, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur. Preferably, $R^7$ and $R^8$ are H, or $R^7$ and $R^8$, together with the boron and oxygen atoms to which they are attached, form a cyclic boronic ester having, in addition to the boron and oxygen atoms and without counting the hydrogen atoms, from 2 to 20 additional atoms chosen from carbon, nitrogen, oxygen and sulfur. In embodiments in which $R^7$ and $R^8$, together with the boron and oxygen atoms to which they are attached, form a cyclic boronic ester, it is preferred that 2-5 of the additional atoms are ring atoms. Preferably, no more than 2 of the additional ring atoms are N, O, or S atoms. Preferably, $R^7$ and $R^8$ are H, or $R^7$ and $R^8$, together with the boron and oxygen atoms to which they are attached, form an optionally substituted 5-8 membered carbon-containing ring having 0-2 additional heteroatoms chosen from nitrogen, oxygen, and sulfur. Preferably, $R^7$ and $R^8$ are H, or $R^7$ and $R^8$, together with the boron and oxygen atoms to which they are attached, form an optionally substituted 5-8 membered carbon-containing ring having 0-1 additional nitrogen atoms. Preferably, $R^7$ and $R^8$ are H, or $R^7$ and $R^8$, together with the boron and oxygen atoms to which they are attached, form an optionally substituted 5-8 membered carbon-containing ring having 0-1 additional nitrogen atoms, wherein the ring atoms other than the boron atom are derived from a chiral diol such as 2,3-butanediol, preferably (2R,3R)-(−)-2,3-butanediol or (2S,3S)-(+)-2,3-butanediol; pinanediol, preferably (1R,2R,3R,5S)-(−)-pinanediol or (1S,2S,3S,5R)-(+)-pinanediol; 1,2-cyclopentanediol, preferably (1S,2S)-(+)-trans-1,2-cyclopentanediol or (1R,2R)-(−)-trans-1,2-cyclopentanediol; 2,5-hexanediol, preferably (2S,5S)-2,5-hexanediol or (2R,5R)-2,5-hexanediol; 1,2-dicyclohexyl-1,2-ethanediol, preferably (1R,2R)-1,2-dicyclohexyl-1,2-ethanediol or (1S,2S)-1,2-dicyclohexyl-1,2-ethanediol; hydrobenzoin, preferably (S,S)-(−)-hydrobenzoin or (R,R)-(+)-hydrobenzoin; 2,4-pentanediol, preferably (R,R)-(−)-2,4-pentanediol or (S,S,)-(+)-2,4-pentanediol; erythronic γ-lactone, preferably D-erythronic γ-lactone; or a carbohydrate, such as a 1,2,5,6-symmetrically protected mannitol. Preferably, $R^7$ and $R^8$ are H, or $R^7$ and $R^8$, together with the boron and oxygen atoms to which they are attached, form an optionally substituted 5 membered carbon-containing ring, wherein the ring atoms other than the boron atom are derived from (1S,2S,3S,5R)-(+)-pinanediol. In preferred embodiments, $R^7$ and $R^8$ are H. In such embodiments, the invention provides a process for purifying Compound 1.

If necessary, step (a) of the Formula VIII purification process can be performed as described above for step (a) of the Formula VI purification process. In embodiments in which $R^7$ and $R^8$, together with the boron and oxygen atoms to which they are attached, form an 8 membered ring in which the ring atoms other than boron are derived from diisopropanolamine, then the compound of Formula VIII is the same as the boronic ester of Formula IX and it is not necessary to perform step (a) in the purification process of the present invention. In all other embodiments, the compound of Formula VIII is different from the boronic ester of Formula IX, and it is therefore necessary to convert the compound of Formula VIII into the boronic ester of Formula IX in step (a) of the purification process. The compound of Formula VIII can be converted into the boronic ester of Formula IX in step (a) using esterification conditions well known to those of ordinary skill in the art. In certain embodiments, the compound of Formula VIII is directly reacted with diisopropanolamine Optionally, this direct reaction is conducted in the presence of an acid catalyst. Suitable acid catalysts include, but are not limited to, inorganic acids such as hydrochloric, hydrobromic, sulfuric, sulfamic, phosphoric, nitric and the like, and organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. A preferred acid is methanesulfonic acid.

The compound of Formula VIII also may be indirectly converted to the boronic ester of Formula IX by first converting the compound of Formula VIII (when $R^7$ and $R^8$ are not already H) to the corresponding free boronic acid (i.e., Compound 1) and then converting the Compound 1 to the boronic ester of Formula IX. Preferably, the Compound 1 is prepared in situ and reacted with diisopropanolamine to provide the boronic ester of Formula IX. Preferably, the Compound 1 is prepared by transesterification of a boronic ester of Formula VIII ($R^7$, $R^8 \neq$H) with a $C_1$-$C_6$alkylboronic acid, such as 2-methylpropylboronic acid. Preferably, this transesterification reaction is conducted in the presence of an acid catalyst. Suitable acid catalysts include, but are not limited to the mineral acids and organic acids mentioned above. Mineral acids are preferred. A preferred mineral acid is hydrochloric acid. In certain embodiments, the transesterification reaction is conducted using biphasic conditions such that the Compound 1 and the $C_1$-$C_6$alkylboronic acid ester reaction products are phase separated. Suitable solvents for the biphasic reaction include methanol/heptane, with the Compound 1 being present in the methanol layer, and the $C_1$-$C_6$alkylboronic acid ester present in the heptane layer. The Compound 1 is then separated and reacted with diisopropanolamine to provide the boronic ester of Formula IX.

In step (b) of the purification process, the boronic ester of Formula IX is crystallized from solution. Any suitable solvent can be used for the crystallization. Suitable solvents include, but are not limited to, ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, water, and mixtures thereof. Ethanol, ethyl acetate, n-propanol, isopropanol, and methyl tert-butyl ether are preferred. Particularly preferred are ethanol, n-propanol, and isopropanol. Also useful are mixtures of an organic solvent and water, with ethanol/water being a preferred example. When water is used, it is preferably used as an antisolvent to help precipitate the boronic ester of Formula I, rather than as a co-solvent in the initial solubilization. Suitable crystallization methods are well known to those of ordinary skill in the art. Suitable crystallization methods include, but are not limited to, concentrating (e.g., by heating to remove solvent), cooling, precipitating with an antisolvent, seeding, and/or slurrying the solution. Cooling is preferred.

Crystallization step (b) is extremely important to the purification process because it permits substantial upgrades in chemical and chiral purity by simple crystallization alone, without the need to perform more problematic purification methods such as chromatography. It is made possible because the boronic ester of Formula IX is stable and crystalline, and unexpectedly crystallizes from solution in distinct preference to its corresponding diastereomers. These desirable stability, handling, and purification attributes are particularly surprising because esters of Formula VIII are often difficult to form, difficult to purify, unstable, and/or non-crystalline. These surprising properties of the boronic ester of Formula IX, which permit its ready handling, long term storage, and high purity, are especially advantageous because the boronic ester of Formula IX is readily converted to Compound 1 having the same high chemical and chiral purity.

In step (c) of the purification process, the crystalline boronic ester of Formula IX can be isolated by any suitable method, such as filtration, decantation, or centrifugation. Filtration is preferred.

In step (d) of the purification process, the isolated boronic ester of Formula IX is converted back into the compound of Formula VIII, if necessary. In embodiments in which $R^7$ and $R^8$, together with the boron and oxygen atoms to which they are attached, form an 8 membered ring in which the ring atoms other than boron are derived from diisopropanolamine, then the boronic ester of Formula IX is the same as the compound of Formula VIII, and it is not necessary to perform step (d) in the purification process of the present invention. In all other embodiments, the boronic ester of Formula IX is different from the compound of Formula VIII, and it is therefore necessary to convert the boronic ester of Formula IX back into the compound of Formula VIII in step (d) of the purification process. When $R^7$ and $R^8 \neq H$, the boronic ester of Formula IX can be converted into a compound of Formula VIII using the direct or indirect transesterification reactions described above for step (a). When $R^7$ and $R^8$ are H, the boronic ester of Formula IX can be converted to the boronic acid of Formula VIII (i.e., Compound 1) as previously described. For example, the boronic ester of Formula IX can be simply exposed to water, optionally in the presence of an acid catalyst, to prepare Compound 1. Optionally, the hydrolysis may be carried out in an organic solvent, optionally in the presence of an acid catalyst. Suitable organic solvents include, but are not limited to, ethyl acetate, methanol, and methyl t-butyl ether. Suitable acids include, but are not limited to, mineral acids, such as hydrochloric acid, hydrobromic acid, phosphoric acid, nitric acid, and the like. A preferred acid is aqueous hydrochloric acid. Preferably, the hydrolysis is carried out in an organic solvent in the presence of an acid catalyst. Preferably, the acid catalyst is aqueous hydrochloric acid.

The chemical and chiral purity of the compound of Formula VIII obtained from the purification process is often sufficiently high, such that the compound of Formula VIII can be directly used in pharmaceutical preparations. Preferably, the compound of Formula VIII has a chemical purity of at least 90%. More preferably, the compound of Formula VIII has a chemical purity of at least 95%. More preferably, the compound of Formula VIII has a chemical purity of at least 97%. More preferably, the compound of Formula VIII has a chemical purity of at least 98%. More preferably, the compound of Formula VIII has a chemical purity of at least 98.5%. More preferably, the compound of Formula VIII has a chemical purity of at least 99%. More preferably, the compound of Formula VIII has a chemical purity of at least 99.5%. Preferably, the compound of Formula VIII has a chiral purity of at least 90% de. Preferably, the compound of Formula VIII has a chiral purity of at least 92% de. More preferably, the compound of Formula VIII has a chiral purity of at least 95% de. More preferably, the compound of Formula VIII has a chiral purity of at least 97% de. More preferably, the compound of Formula VIII has a chiral purity of at least 98% de. More preferably, the compound of Formula VIII has a chiral purity of at least 98.5% de. More preferably, the compound of Formula VIII has a chiral purity of at least 99% de. More preferably, the compound of Formula VIII has a chiral purity of at least 99.2% de. More preferably, the compound of Formula VIII has a chiral purity of at least 99.3% de. More preferably, the compound of Formula VIII has a chiral purity of at least 99.5% de. More preferably, the compound of Formula VIII has a chiral purity of at least 99.7% de. More preferably, the compound of Formula VIII has a chiral purity of at least 99.8% de.

Optionally, the isolated boronic ester of Formula IX may be recrystallized prior to converting it back into the compound of Formula VIII to increase its chemical and/or chiral purity. Recrystallization techniques and conditions are known in the art and suitable conditions can be identified without undue experimentation. Suitable recrystallization solvents include, but are not limited to, organic solvents such as ethyl acetate, methyl tert-butyl ether, n-propanol, isopropanol, ethanol, isopropyl acetate, n-propyl acetate, acetonitrile, n-butyl acetate, isobutyl methyl ketone, acetone, 2-butanone, and mixtures thereof Also suitable are mixtures of water and organic solvents, such as the organic solvents previously mentioned, with ethanol/water being a preferred example. When water is used, it is preferably used as an antisolvent to help precipitate the boronic ester of Formula I, rather than as a co-solvent in the initial solubilization. Ethanol, ethyl acetate, n-propanol, isopropanol, and methyl tert-butyl ether are preferred recrystallization solvents. Particularly preferred are ethanol, n-propanol, and isopropanol. The crystalline boronic ester of Formula IX can be isolated by any suitable method, such as filtration, decantation, or centrifugation. Filtration is preferred.

Preferably, the recrystallized boronic ester of Formula IX has a chemical purity of at least 95%. More preferably, the recrystallized boronic ester of Formula IX has a chemical purity of at least 97%. More preferably, the recrystallized boronic ester of Formula IX has a chemical purity of at least 98%. More preferably, the recrystallized boronic ester of Formula IX has a chemical purity of at least 98.5%. More preferably, the recrystallized boronic ester of Formula IX has a chemical purity of at least 99%. More preferably, the recrystallized boronic ester of Formula IX has a chemical purity of at least 99.5%. More preferably, the recrystallized boronic ester of Formula IX has a chemical purity of at least 99.8%. More preferably, the recrystallized boronic ester of Formula IX has a chemical purity of at least 99.9%. Preferably, the recrystallized boronic ester of Formula IX has a chiral purity of at least 95% de. More preferably, the recrystallized boronic ester of Formula IX has a chiral purity of at least 97% de. More preferably, the recrystallized boronic ester of Formula IX has a chiral purity of at least 98% de. More preferably, the recrystallized boronic ester of Formula IX has a chiral purity of at least 98.5% de. More preferably, the recrystallized boronic ester of Formula IX has a chiral purity of at least 99% de. More preferably, the recrystallized boronic ester of Formula IX has a chiral purity of at least 99.2% de. More preferably, the recrystallized boronic ester of Formula IX has a chiral purity of at least 99.3% de. More preferably, the recrystallized boronic ester of Formula IX has a chiral purity of at least 99.5% de. More preferably, the recrystallized boronic ester of Formula IX has a chiral purity of at least 99.7% de. More preferably, the recrystallized boronic ester of Formula IX has a chiral purity of at least 99.8% de. More preferably, the recrystallized boronic ester of Formula IX has a chiral purity of at least 99.9% de.

After recrystallization, the boronic ester of Formula IX may, if necessary, be converted in step (d) to the compound of Formula VIII having the same high chemical and chiral purity as the recrystallized boronic ester of Formula IX using the techniques described above.

Compounds

The present invention further provides boronic esters of Formulas IX, X, and XI (XI) having the same high chemical and chiral purity. Therefore, the chemical and chiral purity of Compound 1 or bortezomib can be significantly upgraded using these compounds, and Compound 1 and bortezomib can be stored and even formulated as these esters.

In prior art syntheses, the chiral purities of Compound 1 and bortezomib were limited by the chiral purities of their respective starting materials, SM-2 or SM-3 (i.e., N-[(1S, 2R)-1 [[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (SM-2) or N-[(1S)-1[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]-2-benzyl]2-pyrazine carboxamide (SM-3)).

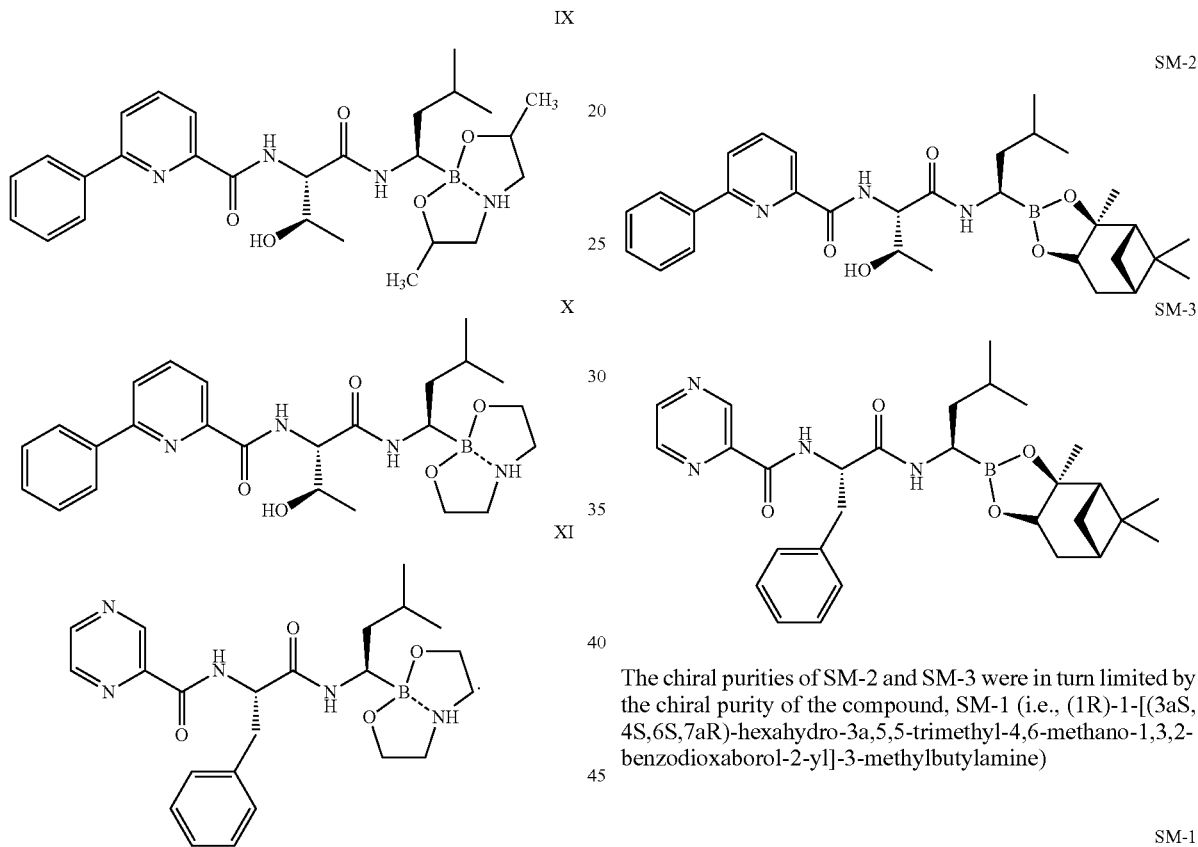

The chiral purities of SM-2 and SM-3 were in turn limited by the chiral purity of the compound, SM-1 (i.e., (1R)-1-[(3aS, 4S,6S,7aR)-hexahydro-3a,5,5-trimethyl-4,6-methano-1,3,2-benzodioxaborol-2-yl]-3-methylbutylamine)

The boronic esters of Formulas IX, X, and XI are critical components of the preparation and purification processes described above. The compounds of Formulas IX, X and XI are diisopropanolamine (IX) or diethanolamine (X and XI) boronic ester derivatives of Compound 1 (IX and X) or bortezomib (XI), and are used in the processes of the present invention to generate Compound 1 or bortezomib in high chemical and chiral purity. As discussed above, the boronic esters of Formulas IX, X, and XI are stable and crystalline, and unexpectedly crystallize from solution in distinct preference to their corresponding diastereomers. These desirable stability, handling, and purification attributes are particularly surprising because other esters of Formulas IV, VI and VIII are often difficult to form, difficult to purify, unstable, and/or non-crystalline. These surprising properties of the boronic esters of Formulas IX, X, and XI are especially advantageous because the boronic esters of Formulas IX, X and XI are readily converted to Compound 1 (IX and X) or bortezomib Therefore, if SM-1 had a low chiral purity, SM-2 or SM-3 would be impure and so would the obtained Compound 1 or bortezomib. The reason for this is that it is exceedingly difficult to increase the purity of Compound 1 or bortezomib by conventional methods, at least partly due to the fact that the compounds tend to degrade during attempted purification. This is especially true of Compound 1. The boronic esters of Formulas IX, X, and XI solve the problem of the prior art. The chiral purities of the compounds of the present invention are not limited by the chiral purity of SM-1, the inventive compounds can be recrystallized to increase chemical and chiral purity beyond 99.5%, and they are readily converted to Compound 1 (IX and X) or bortezomib (XI) without loss of purity.

For example, SM-2 having a chiral purity of only 97.5% de can be transesterified with diisopropanolamine, and the product of Formula IX simply crystallized from the reaction mixture at a chiral purity of greater than 99.8% de (see Example 8). The stable, crystalline compound of Formula IX of high chiral purity can then be converted to Compound 1 having the same high chiral purity. This represents a significant advance over the prior art.

As another example, SM-2 having a chiral purity of only 74% de can be transesterified with diethanolamine, and the product of Formula X simply isolated by crystallization and then recrystallized at a chemical purity of at least 99.8% and a chiral purity of at least 99.8% de (see Example 2). The stable, crystalline boronic ester of Formula X of high chemical and chiral purity can then be converted to Compound 1 having the same high chemical and chiral purity (see Examples 3 and 4). This represents a significant advance over the prior art.

As another example, SM-3 having a chiral purity of only 74% de can be transesterified with diethanolamine, and the product of Formula XI simply isolated by crystallization and then recrystallized at a chiral purity of 88% de and a chemical purity of at least 99.9% (see Example 6). The stable, crystalline boronic ester of Formula XI of high chemical and chiral purity can then be converted to bortezomib having the same high chemical and chiral purity (see Example 7). This represents a significant advance over the prior art.

A further advantage of the boronic esters of Formulas IX, X, and XI is that they are storage stable. Compound 1 is exceedingly troublesome to work with because it is very unstable, and can readily degrade during handling and storage, even when stored under refrigerated conditions. For example, total impurities can increase more than 10-fold (from 0.6% to 7.3%) within six months even when Compound 1 is stored under refrigerated conditions (Example 9A). For that reason, the standard storage temperature for Compound 1 is −20° C. Moreover, the instability of Compound 1 limits the purity level attainable when Compound 1 is synthesized according to the prior art methods, since Compound 1 also degrades during attempted chromatographic purification. The boronic esters of Formulas IX and X solve these problems. For example, the boronic ester of Formula X remains 99.8% pure even after storage for 6 months under extreme conditions of 40° C. and 75% relative humidity (see Example 9), and can be used to prepare Compound 1 having the same high chemical and chiral purities (see Examples 3 and 4). The ability to obtain and conveniently store Compound 1 (e.g., at room temperature or above) in high purity as its boronic esters IX and X constitutes a significant improvement over the prior art.

Thus, in another embodiment, the present invention provides Compound 1 having high chemical purity and high chiral purity. In one embodiment, the Compound 1 has a chemical purity of at least 98.5%. Preferably, the Compound 1 has a chemical purity of at least 98.6%. More preferably, the Compound 1 has a chemical purity of at least 98.7%. More preferably, the Compound 1 has a chemical purity of at least 98.8%. More preferably, the Compound 1 has a chemical purity of at least 98.9%. More preferably, the Compound 1 has a chemical purity of at least 99.0%. More preferably, the Compound 1 has a chemical purity of at least 99.1%. More preferably, the Compound 1 has a chemical purity of at least 99.2%. More preferably, the Compound 1 has a chemical purity of at least 99.3%. More preferably, the Compound 1 has a chemical purity of at least 99.4%. More preferably, the Compound 1 has a chemical purity of at least 99.5%. More preferably, the Compound 1 has a chemical purity of at least 99.6%. More preferably, the Compound 1 has a chemical purity of at least 99.7%. More preferably, the Compound 1 has a chemical purity of at least 99.8%. More preferably, the Compound 1 has a chemical purity of at least 99.9%. Preferably, the Compound 1 has a chiral purity of at least 98.5% de. More preferably, the Compound 1 has a chiral purity of at least 98.6% de. More preferably, the Compound 1 has a chiral purity of at least 98.7% de. More preferably, the Compound 1 has a chiral purity of at least 98.8% de. More preferably, the Compound 1 has a chiral purity of at least 98.9% de. More preferably, the Compound 1 has a chiral purity of at least 99.0% de. More preferably, the Compound 1 has a chiral purity of at least 99.1% de. More preferably, the Compound 1 has a chiral purity of at least 99.2% de. More preferably, the Compound 1 has a chiral purity of at least 99.3% de. More preferably, the Compound 1 has a chiral purity of at least 99.4% de. More preferably, the Compound 1 has a chiral purity of at least 99.5% de. More preferably, the Compound 1 has a chiral purity of at least 99.6% de. More preferably, the Compound 1 has a chiral purity of at least 99.7% de. More preferably, the Compound 1 has a chiral purity of at least 99.8% de. More preferably, the Compound 1 has a chiral purity of at least 99.9% de.

A further advantage of the boronic esters of Formulas IX, X, and XI is that they may be used as prodrugs of Compound 1 (IX and X) and bortezomib (XI). Whether administered orally or by injection, the boronic esters of Formulas IX, X, and XI are readily hydrolyzed to provide Compound 1 (IX and X) or bortezomib (XI). Surprisingly, the boronic ester of Formula XI increased the oral bioavailability of bortezomib by 200% when administered orally in saline to rats (Examples 10-11). This result is surprising and unexpected in view of the very low bioavailability of bortezomib itself, and in view of the fact that the boronic ester of Formula XI readily hydrolyzes under acidic aqueous conditions as found in the stomach. The surprising increase in oral bioavailability of bortezomib made possible by the boronic ester of Formula XI provides for the first time a feasible mechanism by which to administer bortezomib orally. This represents a significant improvement over the bortezomib injection of the prior art.

Pharmaceutical Formulations

The present invention further provides a pharmaceutical composition comprising a compound of the present invention (i.e., a compound chosen from Compound 1 having high chemical and chiral purity, the boronic ester of Formula IX, the boronic ester of Formula X, and the boronic ester of Formula XI), and a pharmaceutically acceptable carrier, diluent, or excipient. Preferably, the pharmaceutical composition contains a compound of the present invention in an amount therapeutically effective for treating a disease or disorder. Preferably, the disease or disorder is multiple myeloma.

In one embodiment, the present invention provides a pharmaceutical composition comprising Compound 1 having high chemical purity and high chiral purity, and a pharmaceutically acceptable carrier, diluent, or excipient. In another embodiment, the present invention provides a pharmaceutical composition comprising a boronic ester of Formula IX, and a pharmaceutically acceptable carrier, diluent, or excipient. In another embodiment, the present invention provides a pharmaceutical composition comprising a boronic ester of Formula X, and a pharmaceutically acceptable carrier, diluent, or excipient. In another embodiment, the present invention provides a pharmaceutical composition comprising a boronic ester of Formula XI, and a pharmaceutically acceptable carrier, diluent, or excipient.

The invention further provides a process for preparing a pharmaceutical composition, comprising the step of combining a compound of the present invention with a pharmaceutically acceptable carrier, diluent, or excipient. In one embodiment, the invention provides a process for preparing a pharmaceutical composition, comprising the step of combining Compound 1 having high chemical and chiral purity with a pharmaceutically acceptable carrier, diluent, or excipient. In another embodiment, the invention provides a process for preparing a pharmaceutical composition, comprising the step of combining a boronic ester of Formula IX with a pharmaceutically acceptable carrier, diluent, or excipient. In another embodiment, the invention provides a process for preparing a pharmaceutical composition, comprising the step of combining a boronic ester of Formula X with a pharmaceutically acceptable carrier, diluent, or excipient. In another embodiment, the invention provides a process for preparing a pharmaceutical composition, comprising the step of combining a boronic ester of Formula XI with a pharmaceutically acceptable carrier, diluent, or excipient.

An advantage of the boronic esters of Formulas IX, X, and XI is that they may be used to conveniently prepare pharmaceutical compositions of Compound 1 or bortezomib, since the esters are readily hydrolyzed to form Compound 1 (IX and X) or bortezomib (XI). For example, Example 13 discloses a pharmaceutical formulation of Compound 1 prepared from the boronic ester of Formula X (see Example 13 below). In Example 13, the boronic ester of Formula X is converted to Compound 1 when it is exposed to an acidic aqueous solution containing the excipients mannitol and hydroxypropyl-β-cyclodextrin.

In one embodiment, the present invention provides a process for preparing a pharmaceutical composition of a boronic acid of Formula IA

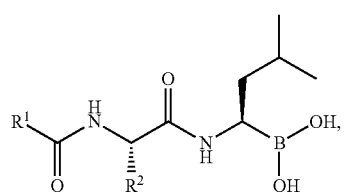

IA wherein $R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) converting a boronic ester of Formula I,

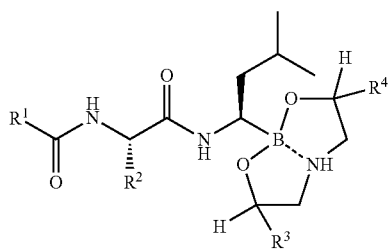

I wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; and
(b) combining the boronic acid of Formula IA with a pharmaceutically acceptable carrier, diluent, or excipient.

In one embodiment, the invention provides a process for preparing a pharmaceutical composition of Compound 1, comprising the steps of (a) converting a boronic ester of Formula IX into Compound 1, and (b) combining the Compound 1 with a pharmaceutically acceptable carrier, diluent, or excipient. In one embodiment, the invention provides a process for preparing a pharmaceutical composition of Compound 1, comprising the steps of (a) converting a boronic ester of Formula X into Compound 1, and (b) combining the Compound 1 with a pharmaceutically acceptable carrier, diluent, or excipient. In one embodiment, the invention provides a process for preparing a pharmaceutical composition of bortezomib, comprising the steps of (a) converting a boronic ester of Formula XI into bortezomib, and (b) combining the bortezomib with a pharmaceutically acceptable carrier, diluent, or excipient.

The boronic esters of Formulas IX, X, and XI can be converted into the corresponding boronic acids (i.e., Compound 1 or bortezomib) as previously described. For example, the boronic esters of Formulas IX, X and XI can be simply exposed to water, optionally in the presence of an acid catalyst, to directly convert the esters into Compound 1 or bortezomib. Optionally, the hydrolysis may be carried out in an organic solvent, optionally in the presence of an acid catalyst. Suitable organic solvents include, but are not limited to, ethyl acetate, methanol, and methyl t-butyl ether. Suitable acids include, but are not limited to, mineral acids, such as hydrochloric acid, hydrobromic acid, phosphoric acid, nitric acid, and the like. A preferred acid is aqueous hydrochloric acid. Optionally, the boronic esters of Formulas IX, X, and XI may be indirectly converted into Compound 1 or bortezomib. For example, the boronic esters of Formulas IX, X, or XI may be initially converted into a different boronic ester (e.g., a boronic ester of Formula VI as described above, wherein $R^7$ and $R^8$ are not H) and then that ester converted into Compound 1 or bortezomib.

In the same way, the combining step (b) may be performed directly or indirectly. For example, Compound 1 or bortezomib can be directly mixed with a pharmaceutically acceptable carrier, diluent, or excipient by simply adding these components together. In these direct embodiments, the boronic ester of Formula IX, X, or XI is converted to Compound 1 or bortezomib prior to mixing with the pharmaceutically acceptable carrier, diluent, or excipient. Alternatively, the components may be indirectly mixed by, for example, mixing a pharmaceutically acceptable carrier, diluent, or excipient with a precursor to Compound 1 or bortezomib, and then converting the precursor to Compound 1 or bortezomib in the presence of the pharmaceutically acceptable carrier, diluent, or excipient. In these indirect embodiments, the converting step is at least partly performed in the presence of the pharmaceutically acceptable carrier, diluent, or excipient.

In one embodiment, the invention provides a process for preparing a pharmaceutical composition of Compound 1, comprising the steps of (a) combining the boronic ester of Formula IX with a pharmaceutically acceptable carrier, diluent, or excipient, and (b) converting the boronic ester of Formula IX into Compound 1. In another embodiment, the invention provides a process for preparing a pharmaceutical composition of Compound 1, comprising the steps of (a)

combining the boronic ester of Formula X with a pharmaceutically acceptable carrier, diluent, or excipient, and (b) converting the boronic ester of Formula X into Compound 1. In another embodiment, the invention provides a process for preparing a pharmaceutical composition of bortezomib, comprising the steps of (a) combining the boronic ester of Formula XI with a pharmaceutically acceptable carrier, diluent, or excipient, and (b) converting the boronic ester of Formula XI into bortezomib.

In one embodiment, the invention provides a process for preparing a pharmaceutical composition of Compound 1, comprising the steps of (a) combining the boronic ester of Formula IX with water and a pharmaceutically acceptable carrier, diluent, or excipient, and optionally (b) drying the combination. In another embodiment, the invention provides a process for preparing a pharmaceutical composition of Compound 1, comprising the steps of (a) combining the boronic ester of Formula X with water and a pharmaceutically acceptable carrier, diluent, or excipient, and optionally (b) drying the combination. In another embodiment, the invention provides a process for preparing a pharmaceutical composition of bortezomib, comprising the steps of (a) combining the boronic ester of Formula XI with water and a pharmaceutically acceptable carrier, diluent, or excipient, and optionally (b) drying the combination. The combination obtained in these embodiments is optionally dried to remove the water used to hydrolyze the boronic ester of Formula IX, Formula X, or Formula XI. A preferred drying method is lyophilization.

In one embodiment, the invention provides a process for preparing a pharmaceutical composition, comprising the steps of (a) combining a compound of the present invention with a pharmaceutically acceptable carrier, diluent, or excipient, and optionally (b) drying the combination. In one embodiment, the invention provides a process for preparing a pharmaceutical composition, comprising the steps of (a) combining Compound 1 having high chemical and chiral purity with a pharmaceutically acceptable carrier, diluent, or excipient, and optionally (b) drying the combination. In another embodiment, the invention provides a process for preparing a pharmaceutical composition, comprising the steps of (a) combining a boronic ester of Formula IX with a pharmaceutically acceptable carrier, diluent, or excipient, and optionally (b) drying the combination. In another embodiment, the invention provides a process for preparing a pharmaceutical composition, comprising the steps of (a) combining a boronic ester of Formula X with a pharmaceutically acceptable carrier, diluent, or excipient, and optionally (b) drying the combination. In another embodiment, the invention provides a process for preparing a pharmaceutical composition, comprising the steps of (a) combining a boronic ester of Formula XI with a pharmaceutically acceptable carrier, diluent, or excipient, and optionally (b) drying the combination. A preferred drying method is lyophilization.

In one embodiment, the invention provides a process for preparing a pharmaceutical composition of Compound 1, comprising the steps of (a) mixing in any order (i) the boronic ester of Formula IX, (ii) water and (iii) a pharmaceutically acceptable carrier, diluent, or excipient; and (b) lyophilizing the mixture. In another embodiment, the invention provides a process for preparing a pharmaceutical composition of Compound 1, comprising the steps of (a) mixing in any order (i) the boronic ester of Formula X, (ii) water and (iii) a pharmaceutically acceptable carrier, diluent, or excipient; and (b) lyophilizing the mixture. In another embodiment, the invention provides a process for preparing a pharmaceutical composition of bortezomib, comprising the steps of (a) mixing in any order (i) the boronic ester of Formula XI, (ii) water and (iii) a pharmaceutically acceptable carrier, diluent, or excipient; and (b) lyophilizing the mixture.

In one embodiment, the invention provides a process for preparing a pharmaceutical composition, comprising the steps of (a) mixing in any order (i) the boronic ester of Formula IX, (ii) water and (iii) a pharmaceutically acceptable carrier, diluent, or excipient; and (b) lyophilizing the mixture. In another embodiment, the invention provides a process for preparing a pharmaceutical composition, comprising the steps of (a) mixing in any order (i) the boronic ester of Formula X, (ii) water and (iii) a pharmaceutically acceptable carrier, diluent, or excipient; and (b) lyophilizing the mixture. In another embodiment, the invention provides a process for preparing a pharmaceutical composition, comprising the steps of (a) mixing in any order (i) the boronic ester of Formula XI, (ii) water and (iii) a pharmaceutically acceptable carrier, diluent, or excipient; and (b) lyophilizing the mixture.

In one embodiment, the invention provides a process for preparing a pharmaceutical composition of Compound 1, comprising the steps of (a) combining the boronic ester of Formula IX with a pharmaceutically acceptable carrier, diluent, or excipient, (b) mixing the combination with water, and (c) lyophilizing the mixture. In another embodiment, the invention provides a process for preparing a pharmaceutical composition of Compound 1, comprising the steps of (a) combining the boronic ester of Formula X with a pharmaceutically acceptable carrier, diluent, or excipient, (b) mixing the combination with water, and (c) lyophilizing the mixture. In another embodiment, the invention provides a process for preparing a pharmaceutical composition of bortezomib, comprising the steps of (a) combining the boronic ester of Formula XI with a pharmaceutically acceptable carrier, diluent, or excipient, (b) mixing the combination with water, and (c) lyophilizing the mixture.

In one embodiment, the invention provides a process for preparing a pharmaceutical composition, comprising the steps of (a) combining the boronic ester of Formula IX with a pharmaceutically acceptable carrier, diluent, or excipient, (b) mixing the combination with water, and (c) lyophilizing the mixture. In another embodiment, the invention provides a process for preparing a pharmaceutical composition, comprising the steps of (a) combining the boronic ester of Formula X with a pharmaceutically acceptable carrier, diluent, or excipient, (b) mixing the combination with water, and (c) lyophilizing the mixture. In another embodiment, the invention provides a process for preparing a pharmaceutical composition, comprising the steps of (a) combining the boronic ester of Formula XI with a pharmaceutically acceptable carrier, diluent, or excipient, (b) mixing the combination with water, and (c) lyophilizing the mixture.

In one embodiment, the invention provides a process for preparing a pharmaceutical composition of Compound 1, comprising the steps of (a) mixing in any order (i) the boronic ester of Formula IX, (ii) water and (iii) a bulking agent; and (b) lyophilizing the mixture. In another embodiment, the invention provides a process for preparing a pharmaceutical composition of Compound 1, comprising the steps of (a) mixing in any order (i) the boronic ester of Formula X, (ii) water and (iii) a bulking agent; and (b) lyophilizing the mixture. In another embodiment, the invention provides a process for preparing a pharmaceutical composition of bortezomib, comprising the steps of (a) mixing in any order (i) the boronic ester of Formula XI, (ii) water and (iii) a bulking agent; and (b) lyophilizing the mixture.

In one embodiment, the invention provides a process for preparing a pharmaceutical composition, comprising the steps of (a) mixing in any order (i) the boronic ester of Formula IX, (ii) water and (iii) a bulking agent; and (b) lyophilizing the mixture. In another embodiment, the invention provides a process for preparing a pharmaceutical composition, comprising the steps of (a) mixing in any order (i) the boronic ester of Formula X, (ii) water and (iii) a bulking agent; and (b) lyophilizing the mixture. In another embodiment, the invention provides a process for preparing a pharmaceutical composition, comprising the steps of (a) mixing in any order (i) the boronic ester of Formula XI, (ii) water and (iii) a bulking agent; and (b) lyophilizing the mixture.

In one embodiment, the invention provides a process for preparing a pharmaceutical composition of Compound 1, comprising the steps of (a) combining the boronic ester of Formula IX with a bulking agent, (b) mixing the combination with water, and (c) lyophilizing the mixture. In another embodiment, the invention provides a process for preparing a pharmaceutical composition of Compound 1, comprising the steps of (a) combining the boronic ester of Formula X with a bulking agent, (b) mixing the combination with water, and (c) lyophilizing the mixture. In another embodiment, the invention provides a process for preparing a pharmaceutical composition of bortezomib, comprising the steps of (a) combining the boronic ester of Formula XI with a bulking agent, (b) mixing the combination with water, and (c) lyophilizing the mixture.

In one embodiment, the invention provides a process for preparing a pharmaceutical composition, comprising the steps of (a) combining the boronic ester of Formula IX with a bulking agent, (b) mixing the combination with water, and (c) lyophilizing the mixture. In another embodiment, the invention provides a process for preparing a pharmaceutical composition, comprising the steps of (a) combining the boronic ester of Formula X with a bulking agent, (b) mixing the combination with water, and (c) lyophilizing the mixture. In another embodiment, the invention provides a process for preparing a pharmaceutical composition, comprising the steps of (a) combining the boronic ester of Formula XI with a bulking agent, (b) mixing the combination with water, and (c) lyophilizing the mixture.

In one embodiment, the invention provides a process for preparing a pharmaceutical composition of Compound 1, comprising the steps of (a) mixing in any order (i) the boronic ester of Formula IX, (ii) water, (iii) a bulking agent, and (iv) a cyclodextrin; and (b) lyophilizing the mixture. In another embodiment, the invention provides a process for preparing a pharmaceutical composition of Compound 1, comprising the steps of (a) mixing in any order (i) the boronic ester of Formula X, (ii) water, (iii) a bulking agent, and (iv) a cyclodextrin; and (b) lyophilizing the mixture. In another embodiment, the invention provides a process for preparing a pharmaceutical composition of bortezomib, comprising the steps of (a) mixing in any order (i) the boronic ester of Formula XI, (ii) water, (iii) a bulking agent, and (iv) a cyclodextrin; and (b) lyophilizing the mixture.

In one embodiment, the invention provides a process for preparing a pharmaceutical composition, comprising the steps of (a) mixing in any order (i) the boronic ester of Formula IX, (ii) water, (iii) a bulking agent, and (iv) a cyclodextrin; and (b) lyophilizing the mixture. In another embodiment, the invention provides a process for preparing a pharmaceutical composition, comprising the steps of (a) mixing in any order (i) the boronic ester of Formula X, (ii) water, (iii) a bulking agent, and (iv) a cyclodextrin; and (b) lyophilizing the mixture. In another embodiment, the invention provides a process for preparing a pharmaceutical composition, comprising the steps of (a) mixing in any order (i) the boronic ester of Formula XI, (ii) water, (iii) a bulking agent, and (iv) a cyclodextrin; and (b) lyophilizing the mixture.

In the above embodiments, unless otherwise specified the pharmaceutical composition may be in the form of a syrup, an elixir, a suspension, a powder, a granule, a tablet, a capsule, a lozenge, a troche, an aqueous solution, a cream, an ointment, a lotion, a gel, an emulsion, etc. Solid form preparations include powders, tablets, pills, capsules, cachets, suppositories, and dispersible granules. Preferably, the pharmaceutical composition is a tablet or capsule. In one embodiment, the pharmaceutical composition is a tablet. In another embodiment, the pharmaceutical composition is a capsule. Preferably, the pharmaceutical composition is a lyophilized powder. Preferably, the lyophilized powder is reconstituted, for example using 0.9% NaCl, and administered by injection.

Bulking agents that have "generally regarded as safe" (GRAS) status from the United States Food and Drug Administration (FDA) are well known in the art of pharmaceutical lyophilization, tend to strengthen the structure of the resulting lyophilized cake, and may be used in the present invention. Preferred bulking agents include saccharides, preferably monosaccharides or oligosaccharides, amino acids, sugar alcohols, and mixtures thereof More preferred bulking agents include saccharides, preferably monosaccharides or oligosaccharides, sugar alcohols, and mixtures thereof More preferably, bulking agents used in the present invention include sucrose, dextrose, maltose, lactose, sorbitol, glycine, and dextran. A most preferred bulking agent is mannitol.

Preferred cyclodextrins include the naturally occurring cyclodextrins, methyl-β-cyclodextrin, dimethyl-β-cyclodextrin, trimethyl-β-cyclodextrin, 2-hydroxymethyl-β-cyclodextrin, hydroxyethyl-β-cyclodextrin, 2-hydroxypropyl-β-cyclodextrin, 3-hydroxypropyl-β-cyclodextrin, β-cyclodextrin sulfate, β-cyclodextrin sulfonate, or β-cyclodextrin sulfobutyl ether. Most of these are commercially available from such suppliers as Aldrich Chemical Company, Milwaukee Wis. and Wacker Chemicals, New Canaan, Conn. Preferred cyclodextrins include β-cyclodextrin, hydroxypropyl-β-cyclodextrin and β-cyclodextrin sulfobutyl ether. Preferably, the cyclodextrin is hydroxypropyl β cyclodextrin, hydroxypropyl γ cyclodextrin, sulfobutyl ether β-cyclodextrin, or a mixture thereof. Preferred cyclodextrins include hydroxypropyl-β-cyclodextrin and β-cyclodextrin sulfobutyl ether. In the most preferred embodiments, the cyclodextrin is hydroxypropyl-β-cyclodextrin. One particularly preferred cyclodextrin is KLEPTOSE® HPB, available from Roquette Frères, France.

The pharmaceutical composition preferably contains from 1% to 95% (w/w) of the active compound (i.e., compound of the present invention). More preferably, the pharmaceutical composition contains from 5% to 70% (w/w) of the active compound.

Preferably, the pharmaceutical composition contains at least one unit dose of the active compound. In general, the unit dose of a compound of the present invention is from about 1 ng/kg to 10 mg/kg for a typical subject. More preferably, the unit dose of a compound of the present invention is from about 0.1 mg/m$^2$ to about 10 mg/m$^2$. More preferably, the unit dose of a compound of the present invention is from about 0.5 mg/m$^2$ to about 10 mg/m$^2$. More preferably, the unit dose of a compound of the present invention is from about 0.5 mg/m$^2$ to about 7 mg/m$^2$. More preferably, the unit dose of a compound of the present invention is from about 0.5 mg/m$^2$ to about 5 mg/m$^2$. More preferably, the unit dose of a compound of the present invention is from about 0.5 mg/m$^2$ to about 3 mg/m$^2$.

Preferred Embodiments of the Process for Preparation, Processes for Purification, Compounds, and Pharmaceutical Composition of the Present Invention Preferred embodiments of the present invention include those listed below.

Embodiment 1

A process for preparing Compound 1

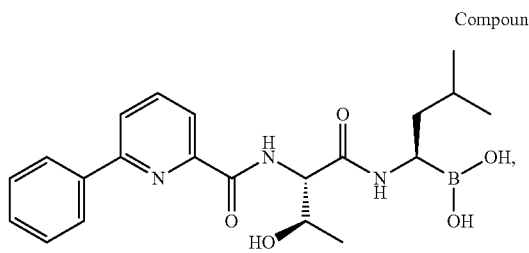

Compound 1 comprising the steps of:
(a) coupling a compound of Formula II

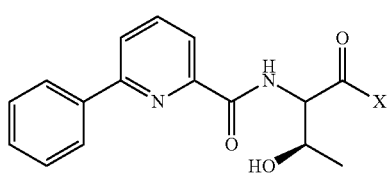

II with an amine of Formula III

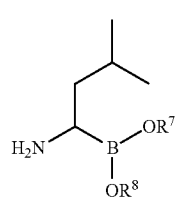

III to form an amide of Formula IV

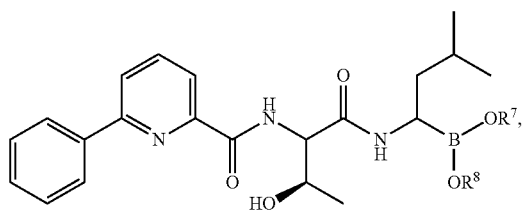

IV wherein
X is OH or a leaving group; and
$R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula VA

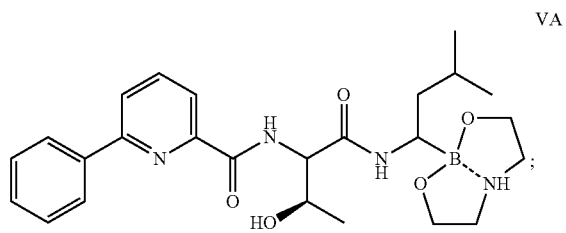

VA (c) crystallizing the boronic ester of Formula X from a solution of the boronic ester of Formula VA

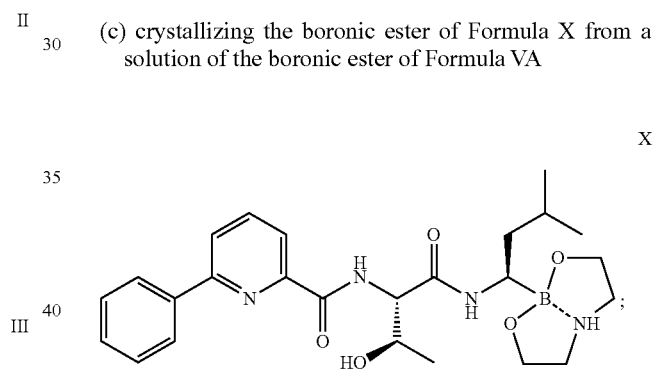

X and
(d) converting the boronic ester of Formula X into Compound 1.

Embodiment 2

A Process for Preparing Compound 1

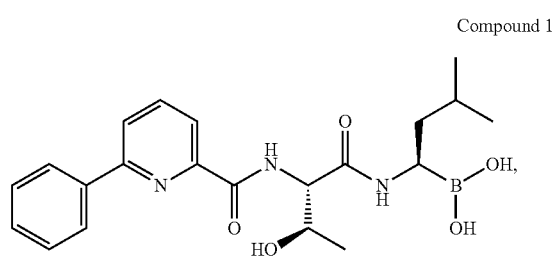 [SMILES: CC(C)C[C@H](NC(=O)[C@@H](NC(=O)c1cccc(-c2ccccc2)n1)[C@@H](C)O)B(O)O]

Compound 1 comprising the steps of:
(a) coupling a compound of Formula II

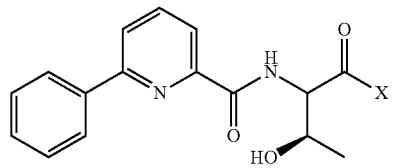

with an amine of Formula III

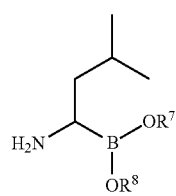

to form an amide of Formula IV

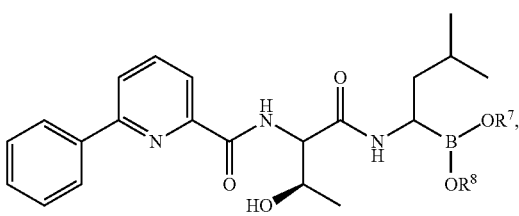

wherein

X is OH or a leaving group; and $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula VA, converting the amide of Formula IV into a boronic ester of Formula VA

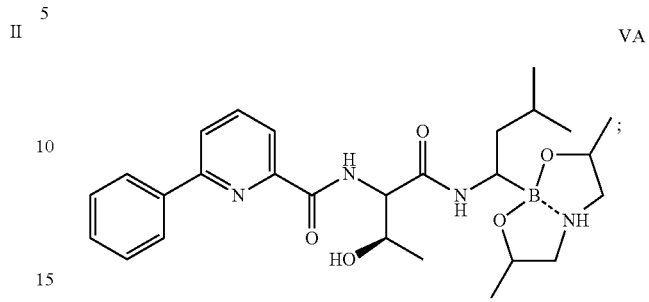

(c) crystallizing the boronic ester of Formula IX from a solution of the boronic ester of Formula VA

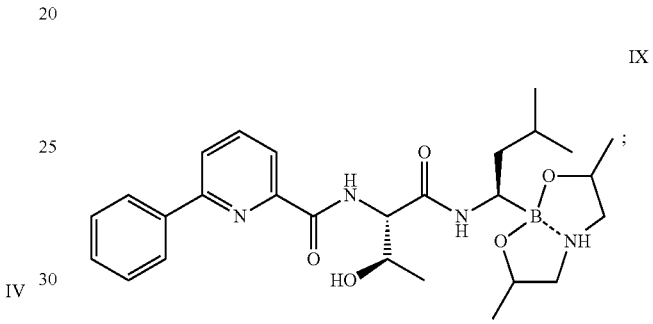

and
(d) converting the boronic ester of Formula IX into Compound 1.

Embodiment 3

A Process for Preparing Bortezomib

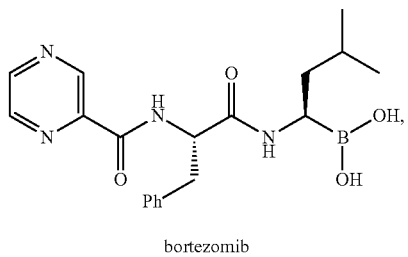 [SMILES: CC(C)C[C@H](NC(=O)[C@H](Cc1ccccc1)NC(=O)c1cnccn1)B(O)O]

bortezomib comprising the steps of:
(a) coupling a compound of Formula II

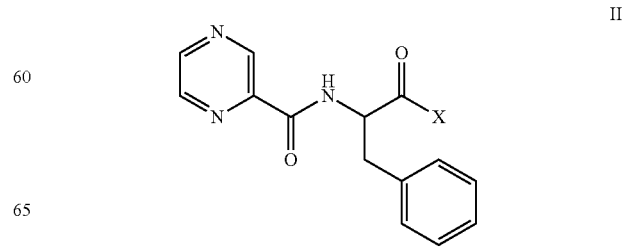

with an amine of Formula III

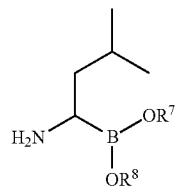

III to form an amide of Formula IV

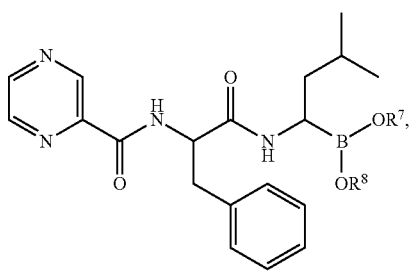

IV wherein

X is OH or a leaving group; and

R$^7$ and R$^8$ are independently chosen from optionally substituted C$_{1-6}$alkyl, optionally substituted C$_{6-10}$aryl, optionally substituted C$_{7-16}$arylalkyl, optionally substituted C$_{3-11}$cycloalkyl, optionally substituted C$_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or R$^7$ and R$^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula VB, converting the amide of Formula IV into a boronic ester of Formula VB

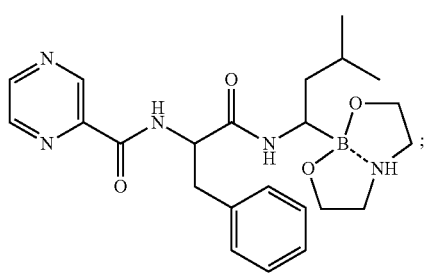

VB (c) crystallizing the boronic ester of Formula XI from a solution of the boronic ester of Formula VB

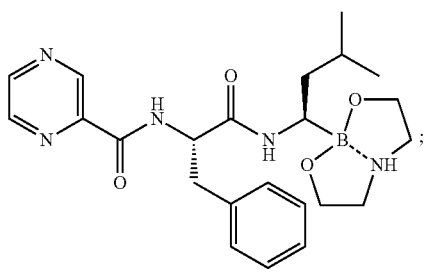

XI and (d) converting the boronic ester of Formula XI into bortezomib.

Embodiment 4

The process of Embodiment 1, further comprising the step of recrystallizing the boronic ester of Formula X after step (c) before performing step (d).

Embodiment 5

The process of Embodiment 2, further comprising the step of recrystallizing the boronic ester of Formula IX after step (c) before performing step (d).

Embodiment 6

The process of Embodiment 3, further comprising the step of recrystallizing the boronic ester of Formula XI after step (c) before performing step (d).

Embodiment 7

The process of any of Embodiments 1 to 6, wherein R$^7$ and R$^8$, together with the boron and oxygen atoms to which they are attached, form an optionally substituted 5-8 membered carbon-containing ring having 0-2 additional heteroatoms chosen from nitrogen, oxygen, and sulfur.

Embodiment 8

The process of Embodiment 7, wherein R$^7$ and R$^8$, together with the boron and oxygen atoms to which they are attached, form an optionally substituted 5-8 membered carbon-containing ring having 0-1 additional nitrogen atoms, wherein the atoms other than the ring boron atom are derived from a chiral diol.

Embodiment 9

The process of Embodiment 8, wherein the atoms other than the ring boron atom are derived from (1S,2S,3S,5R)-(+)-pinanediol, so that the amine of Formula III has the following structure

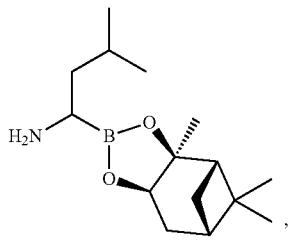 [SMILES: CC(C)CC(N)B1O[C@@H]2C[C@@H]3C[C@@H](C3(C)C)[C@]2(C)O1]

, and the amide of Formula IV has the following structure

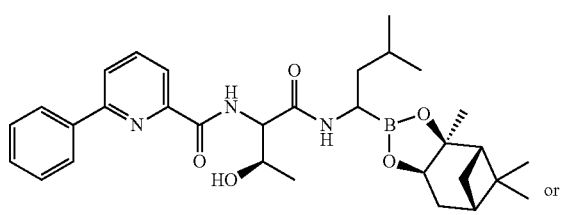

or

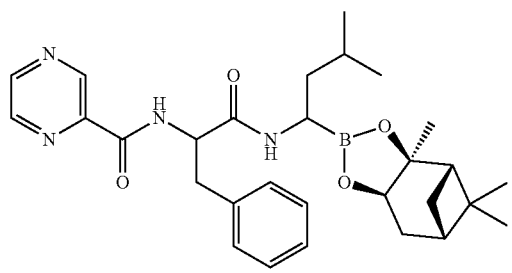

.

Embodiment 10

A Process for Preparing a Boronic Acid of Formula IA

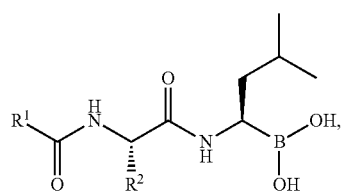

IA wherein $R^1$ is 2-(6-phenyl)pyridinyl and $R^2$ is (1R)-1-hydroxyethyl, or $R^1$ is 2-pyrazinyl and $R^2$ is benzyl;

comprising the steps of:

(a) coupling a compound of Formula II

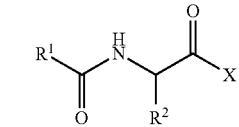

II with an amine of Formula III

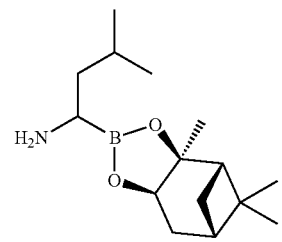

III to form an amide of Formula IV

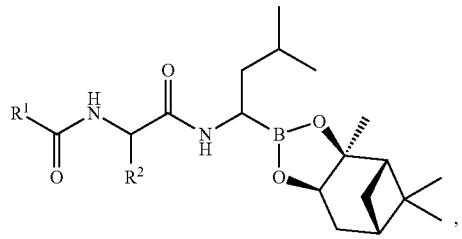

IV wherein X is OH or a leaving group;

(b) converting the amide of Formula IV into a boronic ester of Formula V

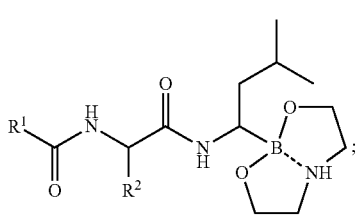

V (c) crystallizing the boronic ester of Formula I from a solution of the boronic ester of Formula V

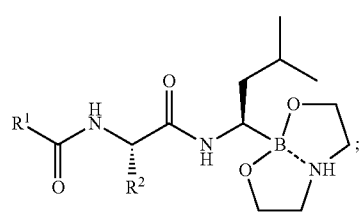
I and (d) converting the boronic ester of Formula I into the boronic acid of Formula IA.

Embodiment 11

The process of Embodiment 10, wherein $R^1$ is 2-(6-phenyl)pyridinyl and $R^2$ is (1R)-1-hydroxyethyl (i.e., the boronic acid of Formula IA is Compound 1).

Embodiment 12

The process of Embodiment 10, wherein $R^1$ is 2-pyrazinyl and $R^2$ is benzyl (i.e., the boronic acid of Formula IA is bortezomib).

Embodiment 13

A process for preparing Compound 1

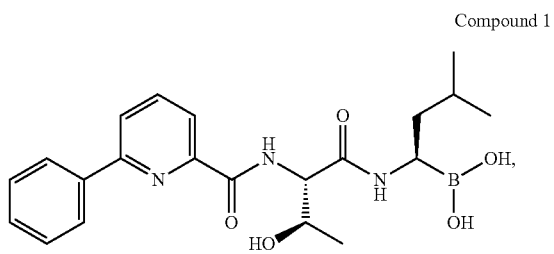 [SMILES: CC(C)C[C@H](NC(=O)[C@@H](NC(=O)c1cccc(-c2ccccc2)n1)[C@@H](C)O)B(O)O]
Compound 1 comprising the steps of:

(a) coupling a compound of Formula II

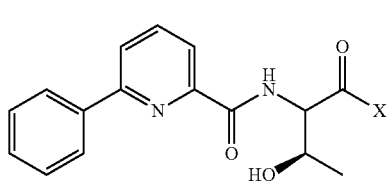
II with an amine of Formula III

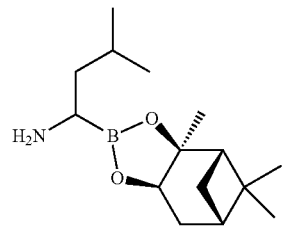
III to form an amide of Formula IV

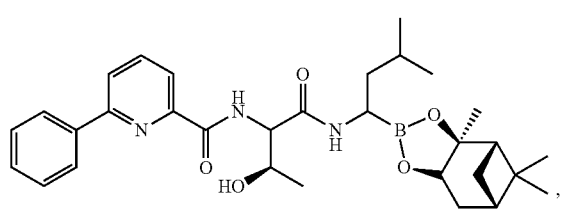
IV wherein X is OH or a leaving group;

(b) converting the amide of Formula IV into a boronic ester of Formula VA

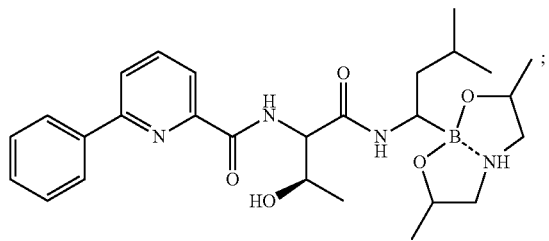
VA (c) crystallizing the boronic ester of Formula IX from a solution of the boronic ester of Formula VA

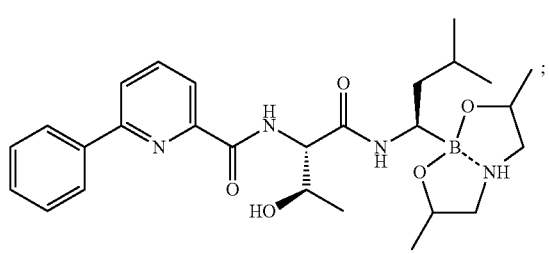
IX and
(d) converting the boronic ester of Formula IX into Compound 1.

Embodiment 14

A Process for Purifying a Boronic Acid of Formula IA

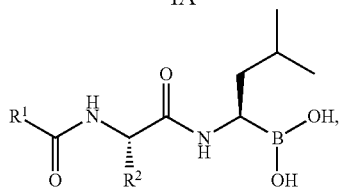

IA wherein
R¹ is 2-(6-phenyl)pyridinyl and R² is (1R)-1-hydroxyethyl, or R¹ is 2-pyrazinyl and R² is benzyl;
comprising the steps of:
(a) converting the boronic acid of Formula IA into a boronic ester of Formula VII

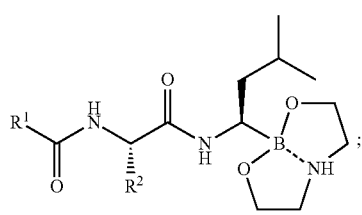

VII (b) crystallizing the boronic ester of Formula VII from solution;
(c) isolating the crystallized boronic ester of Formula VII from the solution; and
(d) converting the isolated boronic ester of Formula VII into a boronic acid of Formula IA.

Embodiment 15

The process of Embodiment 14, wherein R¹ is 2-(6-phenyl)pyridinyl and R² is (1R)-1-hydroxyethyl (i.e., the boronic acid of Formula IA is Compound 1).

Embodiment 16

The process of Embodiment 14, wherein R¹ is 2-pyrazinyl and R² is benzyl (i.e., the boronic acid of Formula IA is bortezomib).

Embodiment 17

The process of any of Embodiments 14-16, further comprising the step of recrystallizing the boronic ester of Formula VII after step (c) before performing step (d).

Embodiment 18

A Process for Purifying Compound 1

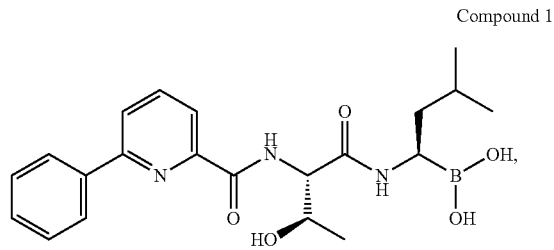 [SMILES: CC(C)C[C@H](NC(=O)[C@@H](NC(=O)c1cccc(-c2ccccc2)n1)[C@@H](C)O)B(O)O]

Compound 1 comprising the steps of:
(a) converting the Compound 1 into a boronic ester of Formula IX

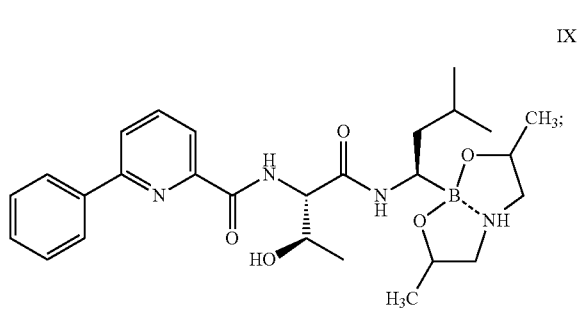

IX (b) crystallizing the boronic ester of Formula IX from solution;
(c) isolating the crystallized boronic ester of Formula IX from the solution; and
(d) converting the isolated boronic ester of Formula IX into Compound 1.

Embodiment 19

The process of Embodiment 18, further comprising the step of recrystallizing the boronic ester of Formula IX after step (c) before performing step (d).

Embodiment 20

A Process for Preparing a Pharmaceutical Composition of a Boronic Acid of Formula IA

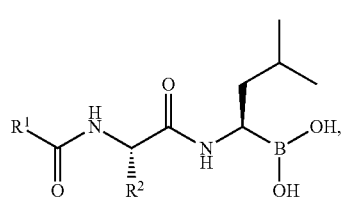

IA wherein R¹ is 2-(6-phenyl)pyridinyl and R² is (1R)-1-hydroxyethyl, or R¹ is 2-pyrazinyl and R² is benzyl;
comprising the steps of:
(a) mixing in any order:
(i) a boronic ester of Formula I

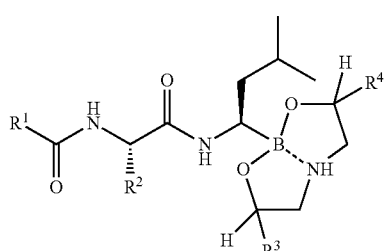

I wherein
R¹ is 2-(6-phenyl)pyridinyl, R² is (1R)-1-hydroxyethyl, and R³ and R⁴ are H;
R¹ is 2-(6-phenyl)pyridinyl, R² is (1R)-1-hydroxyethyl, and R³ and R⁴ are methyl; or
R¹ is 2-pyrazinyl, R² is benzyl, and R³ and R⁴ are H;

(ii) water, and
(iii) a bulking agent; and
(b) lyophilizing the mixture.

Embodiment 21

A Process for Preparing a Pharmaceutical Composition of a Boronic Acid of Formula IA

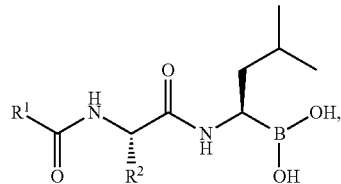

IA wherein R¹ is 2-(6-phenyl)pyridinyl and R² is (1R)-1-hydroxyethyl, or R¹ is 2-pyrazinyl and R² is benzyl;
comprising the steps of:
(a) converting a boronic ester of Formula I,

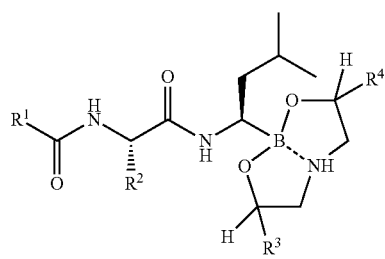

I wherein
R¹ is 2-(6-phenyl)pyridinyl, R² is (1R)-1-hydroxyethyl, and R³ and R⁴ are H;
R¹ is 2-(6-phenyl)pyridinyl, R² is (1R)-1-hydroxyethyl, and R³ and R⁴ are methyl; or
R¹ is 2-pyrazinyl, R² is benzyl, and R³ and R⁴ are H; into a boronic acid of Formula IA; and
(b) combining the boronic acid of Formula IA with a pharmaceutically acceptable carrier, diluent, or excipient.

Embodiment 22

A Process for Preparing a Pharmaceutical Composition of a Boronic Acid of Formula IA

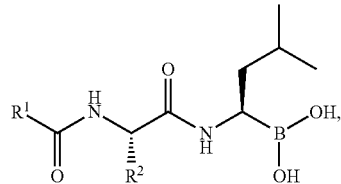

IA wherein R¹ is 2-(6-phenyl)pyridinyl and R² is (1R)-1-hydroxyethyl, or R¹ is 2-pyrazinyl and R² is benzyl;
comprising the steps of:
(a) combining a boronic ester of Formula I,

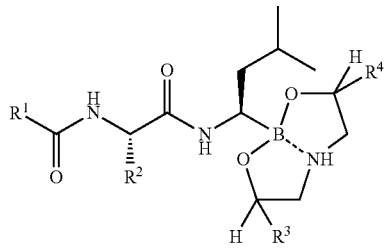

I wherein
R¹ is 2-(6-phenyl)pyridinyl, R² is (1R)-1-hydroxyethyl, and R³ and R⁴ are H;
R¹ is 2-(6-phenyl)pyridinyl, R² is (1R)-1-hydroxyethyl, and R³ and R⁴ are methyl; or
R¹ is 2-pyrazinyl, R² is benzyl, and R³ and R⁴ are H;
with a pharmaceutically acceptable carrier, diluent, or excipient; and
(b) converting the boronic ester of Formula I into the boronic acid of Formula IA.

Embodiment 23

A Process for Preparing a Pharmaceutical Composition of a Boronic Acid of Formula IA

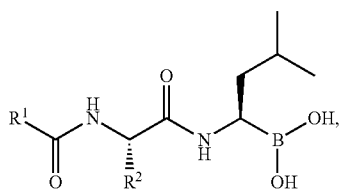

IA wherein R¹ is 2-(6-phenyl)pyridinyl and R² is (1R)-1-hydroxyethyl, or R¹ is 2-pyrazinyl and R² is benzyl;
comprising the steps of:
(a) converting a boronic ester of Formula I,

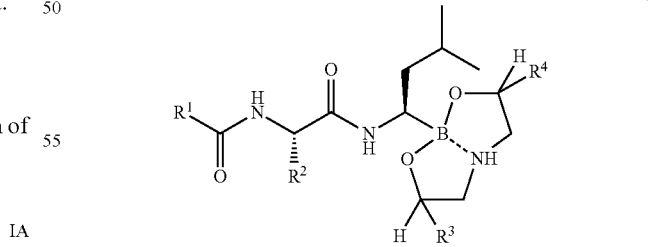

I wherein
R¹ is 2-(6-phenyl)pyridinyl, R² is (1R)-1-hydroxyethyl, and R³ and R⁴ are H;
R¹ is 2-(6-phenyl)pyridinyl, R² is (1R)-1-hydroxyethyl, and R³ and R⁴ are methyl; or
R¹ is 2-pyrazinyl, R² is benzyl, and R³ and R⁴ are H; into a boronic acid of Formula IA; and (b) combining the boronic acid of Formula IA with a bulking agent.

Embodiment 24

A Process for Preparing a Pharmaceutical Composition of a Boronic Acid of Formula IA

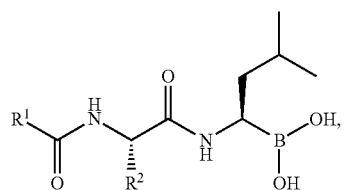

IA wherein $R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) combining a boronic ester of Formula I,

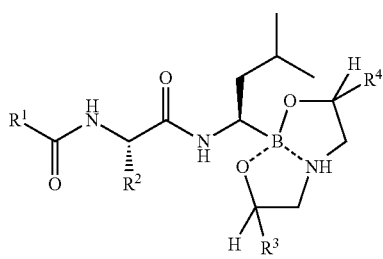

I wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; with a bulking agent; and
(b) converting the boronic ester of Formula I into the boronic acid of Formula IA.

Embodiment 25

The process of any of Embodiments 20, 23, or 24, wherein the bulking agent comprises mannitol.

Embodiment 26

The process of any of Embodiments 20 to 25, wherein $R^1$ is 2-(6-phenyl)pyridinyl and $R^2$ is (1R)-1-hydroxyethyl (i.e., the boronic acid of Formula IA is Compound 1).

Embodiment 27

The process of any of Embodiments 20 to 25, wherein $R^1$ is 2-pyrazinyl and $R^2$ is benzyl (i.e., the boronic acid of Formula IA is bortezomib).

Embodiment 28

The process of Embodiment 26, wherein $R^3$ and $R^4$ are both H.

Embodiment 29

The process of any of Embodiments 20 to 28, wherein the pharmaceutical composition comprises a cyclodextrin.

Embodiment 30

The process of Embodiment 29, wherein the pharmaceutical composition comprises hydroxypropyl-β-cyclodextrin.

Embodiment 31

A Process for Preparing a Boronic Acid of Formula IA

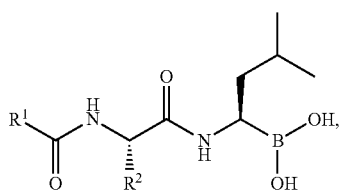

IA wherein
$R^1$ is 2-(6-phenyl)pyridinyl and $R^2$ is (1R)-1-hydroxyethyl, or $R^1$ is 2-pyrazinyl and
$R^2$ is benzyl;
comprising the step of converting a boronic ester of Formula I into the boronic acid of Formula IA

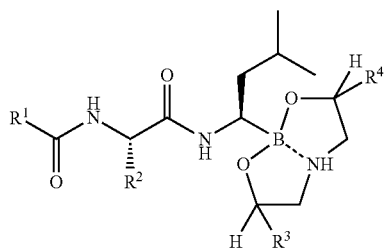

I wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H.

Embodiment 32

The process of Embodiment 31, wherein $R^1$ is 2-(6-phenyl)pyridinyl and $R^2$ is (1R)-1-hydroxyethyl (i.e., the boronic acid of Formula IA is Compound 1).

Embodiment 33

The process of Embodiment 31, wherein $R^1$ is 2-pyrazinyl and $R^2$ is benzyl (i.e., the boronic acid of Formula IA is bortezomib).

Embodiment 34

The process of Embodiment 32, wherein $R^3$ and $R^4$ are both H.

Embodiment 35

A Process for Preparing a Boronic Acid of Formula IA

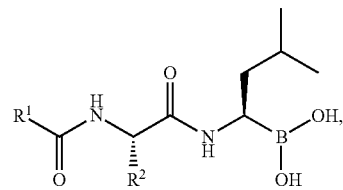

wherein

R¹ is 2-(6-phenyl)pyridinyl and R² is (1R)-1-hydroxyethyl, or R¹ is 2-pyrazinyl and R² is benzyl;

comprising the step of converting a boronic ester of Formula VII into the boronic acid of Formula IA

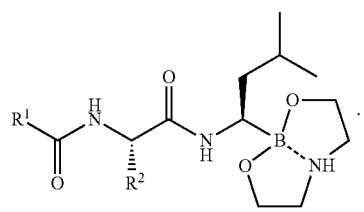

Embodiment 36

A Process for Preparing a Boronic Acid of Formula IA

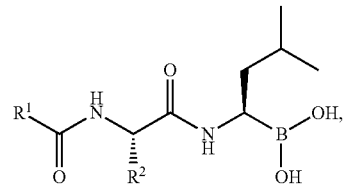

wherein

R¹ is 2-(6-phenyl)pyridinyl and R² is (1R)-1-hydroxyethyl, or R¹ is 2-pyrazinyl and R² is benzyl;

comprising the steps of (a) crystallizing a boronic ester of Formula I from a solution of a boronic ester of Formula V

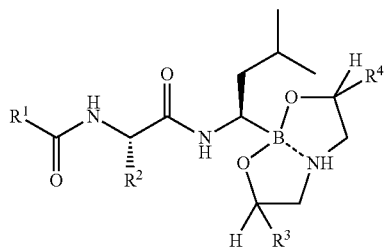

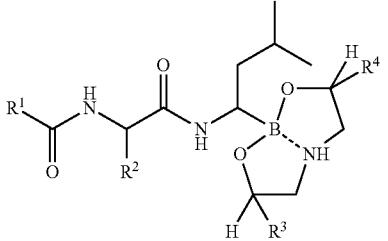

wherein

R¹ is 2-(6-phenyl)pyridinyl, R² is (1R)-1-hydroxyethyl, and R³ and R⁴ are H;

R¹ is 2-(6-phenyl)pyridinyl, R² is (1R)-1-hydroxyethyl, and R³ and R⁴ are methyl; or R¹ is 2-pyrazinyl, R² is benzyl, and R³ and R⁴ are H; and (b) converting the boronic ester of Formula I into the boronic acid of Formula IA.

Embodiment 37

The process Embodiments 35 or 36, wherein R¹ is 2-(6-phenyl)pyridinyl and R² is (1R)-1-hydroxyethyl (i.e., the boronic acid of Formula IA is Compound 1).

Embodiment 38

The process of Embodiments 35 or 36, wherein R¹ is 2-pyrazinyl and R² is benzyl (i.e., the boronic acid of Formula IA is bortezomib).

Embodiment 39

The process of Embodiment 37, wherein R³ and R⁴ are H.

Embodiment 40

A Process for Preparing Compound 1

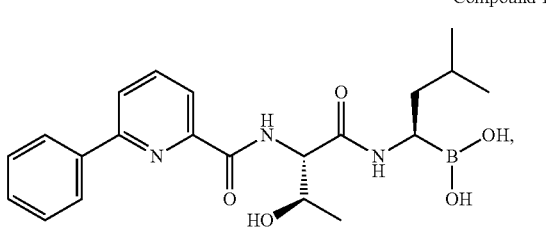

comprising the steps of:
(a) preparing an amide of Formula IV

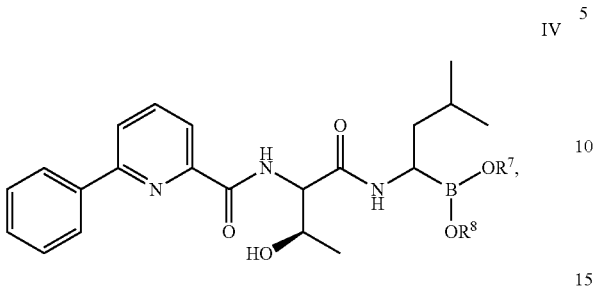

IV wherein
- $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
- or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula VA

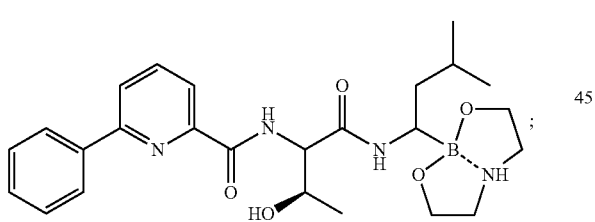

VA (c) crystallizing the boronic ester of Formula X from a solution of the boronic ester of Formula VA

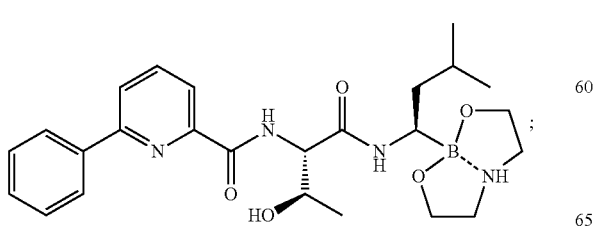

X and
(d) converting the boronic ester of Formula X into Compound 1.

Embodiment 41

A Process for Preparing Compound 1

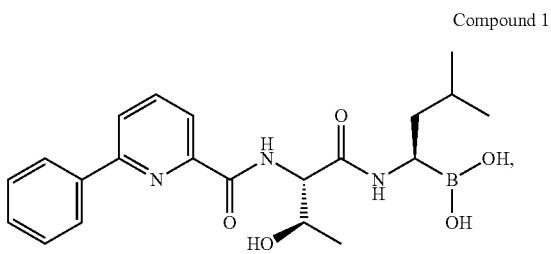 [SMILES: CC(C)C[C@H](NC(=O)[C@@H](NC(=O)c1cccc(-c2ccccc2)n1)[C@@H](C)O)B(O)O]

Compound 1 comprising the steps of:
(a) preparing an amide of Formula IV

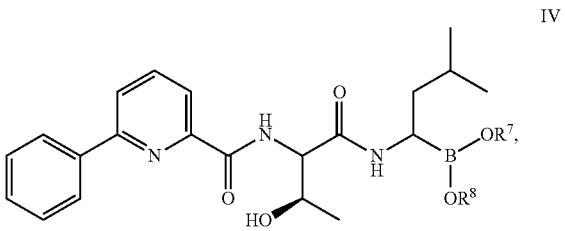

IV wherein
- $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
- or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula VA, converting the amide of Formula IV into a boronic ester of Formula VA

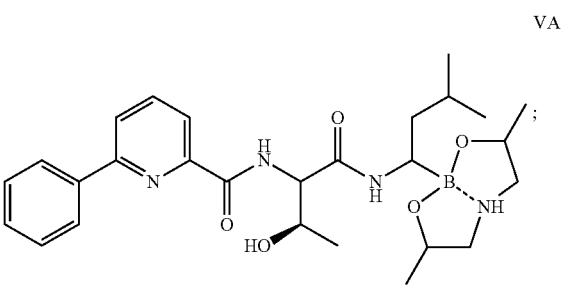

VA (c) crystallizing the boronic ester of Formula IX from a solution of the boronic ester of Formula VA

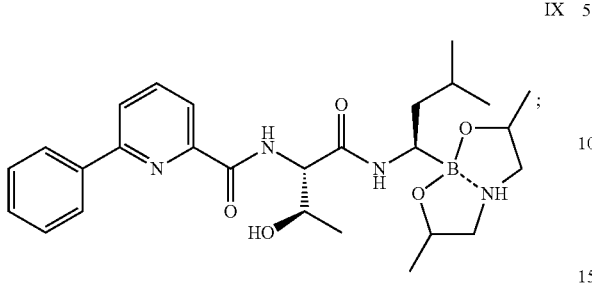

and (d) converting the boronic ester of Formula IX into Compound 1.

Embodiment 42

A Process for Preparing Bortezomib

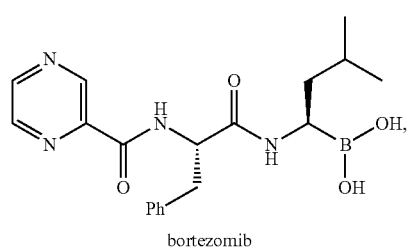 [SMILES: CC(C)C[C@H](NC(=O)[C@H](Cc1ccccc1)NC(=O)c1cnccn1)B(O)O]

bortezomib comprising the steps of:
(a) preparing an amide of Formula IV

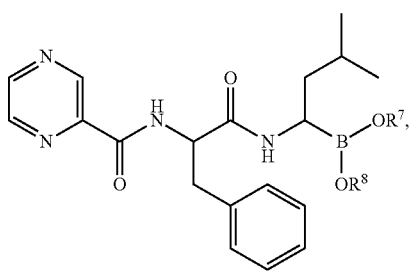

wherein
$R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula VB, converting the amide of Formula IV into a boronic ester of Formula VB

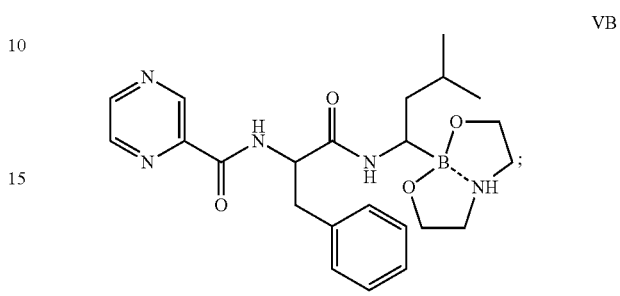

(c) crystallizing the boronic ester of Formula XI from a solution of the boronic ester of Formula VB

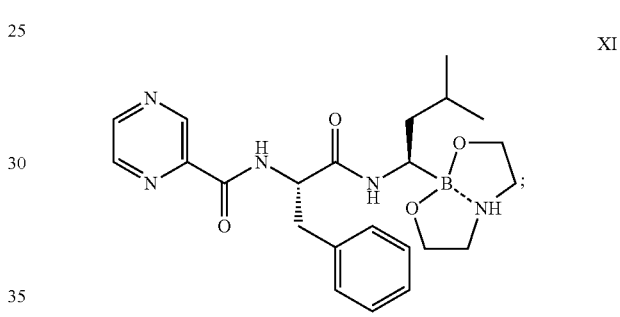

and (d) converting the boronic ester of Formula XI into bortezomib.

Embodiment 43

The process of Embodiment 40, further comprising the step of recrystallizing the boronic ester of Formula X after step (c) before performing step (d).

Embodiment 44

The process of Embodiment 41, further comprising the step of recrystallizing the boronic ester of Formula IX after step (c) before performing step (d).

Embodiment 45

The process of Embodiment 42, further comprising the step of recrystallizing the boronic ester of Formula XI after step (c) before performing step (d).

Embodiment 46

The process of any of Embodiments 40 to 45, wherein $R^7$ and $R^8$, together with the boron and oxygen atoms to which they are attached, form an optionally substituted 5-8 membered carbon-containing ring having 0-2 additional heteroatoms chosen from nitrogen, oxygen, and sulfur.

Embodiment 47

The process of Embodiment 46, wherein $R^7$ and $R^8$, together with the boron and oxygen atoms to which they are attached, form an optionally substituted 5-8 membered carbon-containing ring having 0-1 additional nitrogen atoms, wherein the atoms other than the ring boron atom are derived from a chiral diol.

Embodiment 48

The Process of Embodiment 47, Wherein the Atoms Other than the Ring Boron Atom are Derived From (1S,2S,3S,5R)-(+)-pinanediol, so that the Amide of Formula IV has the Following Structure

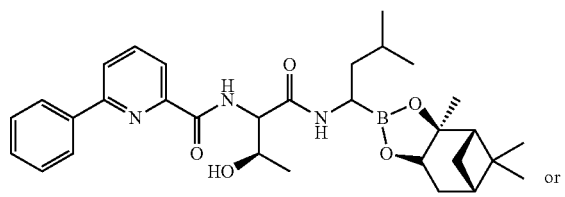

or

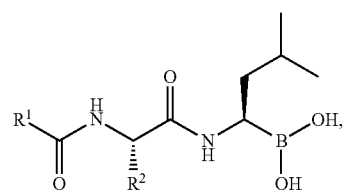

Embodiment 49

A Process for Preparing a Boronic Acid of Formula IA

IA wherein $R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) preparing an amide of Formula IV

IV

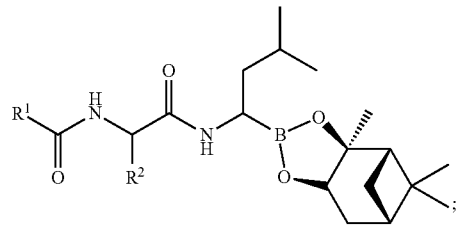

(b) converting the amide of Formula IV into a boronic ester of Formula V

V

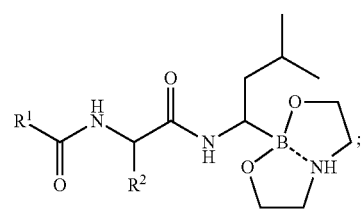

(c) crystallizing the boronic ester of Formula I from a solution of the boronic ester of Formula V

I

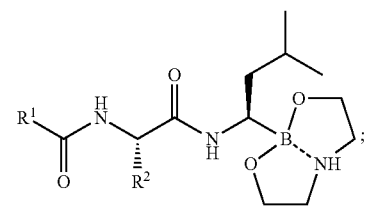

and
(d) converting the boronic ester of Formula I into the boronic acid of Formula IA.

Embodiment 50

The process of Embodiment 49, wherein $R^1$ is 2-(6-phenyl) pyridinyl and $R^2$ is (1R)-1-hydroxyethyl (i.e., the boronic acid of Formula IA is Compound 1).

Embodiment 51

The process of Embodiment 49, wherein $R^1$ is 2-pyrazinyl and $R^2$ is benzyl (i.e., the boronic acid of Formula IA is bortezomib).

Embodiment 52

A Process for Preparing Compound 1

Compound 1

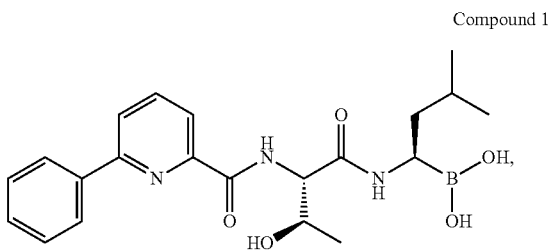 [SMILES: CC(C)C[C@H](NC(=O)[C@@H](NC(=O)c1cccc(-c2ccccc2)n1)[C@@H](C)O)B(O)O]

comprising the steps of:
(a) preparing an amide of Formula IV

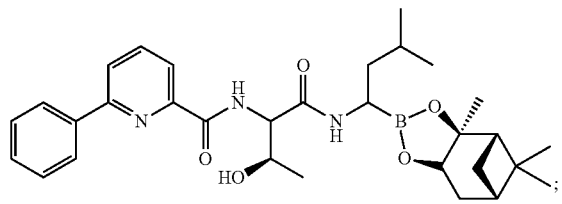

IV (b) converting the amide of Formula IV into a boronic ester of Formula VA

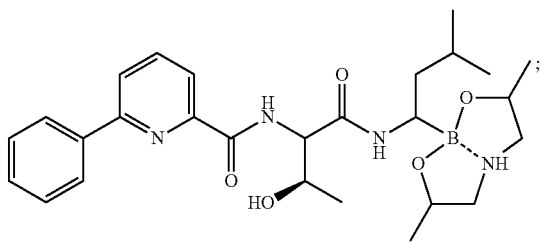

VA (c) crystallizing the boronic ester of Formula IX from a solution of the boronic ester of Formula VA

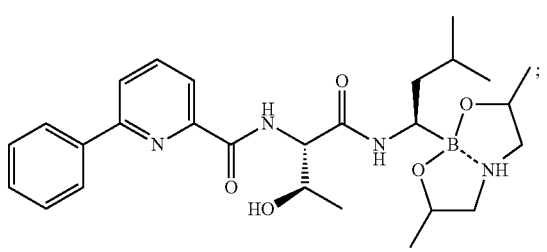

IX and
(d) converting the boronic ester of Formula IX into Compound 1.

Embodiment 53

A Process for Preparing a Boronic Ester of Formula I

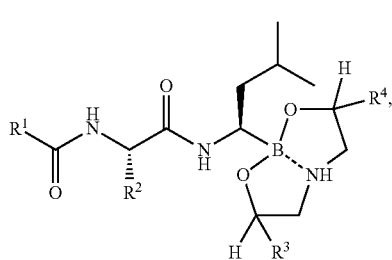

I wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; comprising the steps of:
(a) preparing an amide of Formula IV

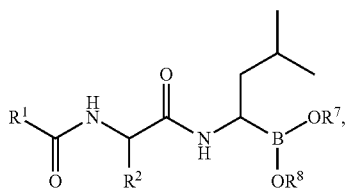

IV wherein $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula V

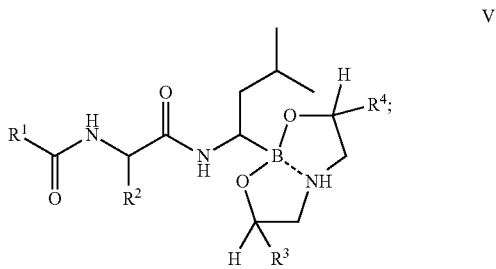

V and
(c) crystallizing the boronic ester of Formula I from a solution of the boronic ester of Formula V.

Embodiment 54

A Process for Preparing a Boronic Ester of Formula I

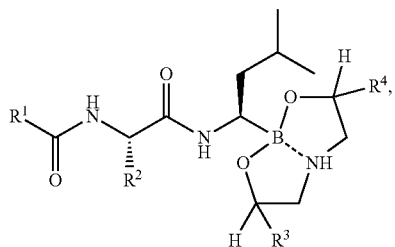

wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; comprising the steps of:
(a) coupling a compound of Formula II

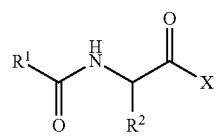

with an amine of Formula III

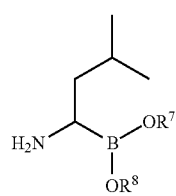

to form an amide of Formula IV

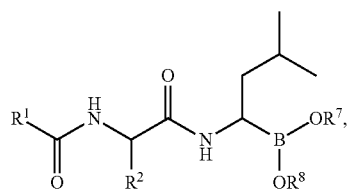

wherein
X is OH or a leaving group; and
$R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;
(b) if the amide of Formula IV is not a boronic ester of Formula V, converting the amide of Formula IV into a boronic ester of Formula V

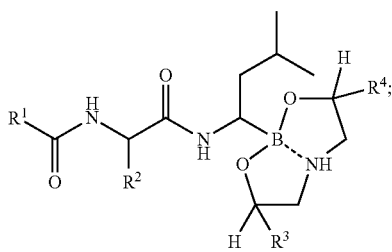

and
(c) crystallizing the boronic ester of Formula I from a solution of the boronic ester of Formula V.

Embodiment 55

A Process for Preparing a Boronic Ester of Formula I

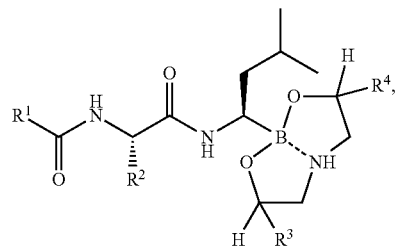

wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; comprising the steps of:
(a) preparing a boronic ester of Formula V

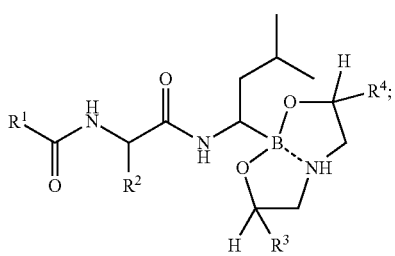

and
(b) crystallizing the boronic ester of Formula I from a solution of the boronic ester of Formula V.

Embodiment 56

A Process for Preparing a Boronic Acid of Formula IA

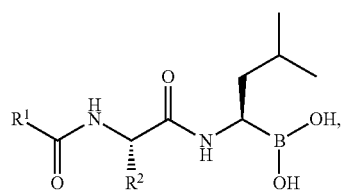

IA wherein
$R^1$ is 2-(6-phenyl)pyridinyl and $R^2$ is (1R)-1-hydroxyethyl, or $R^1$ is 2-pyrazinyl and
$R^2$ is benzyl;
comprising the steps of:
(a) preparing an amide of Formula IV

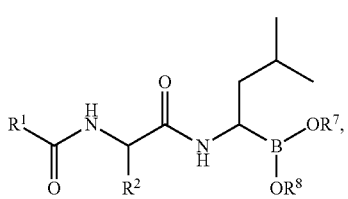

IV wherein
$R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl,
or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;
(b) if the amide of Formula IV is not a boronic ester of Formula V, converting the amide of Formula IV into a boronic ester of Formula V

V

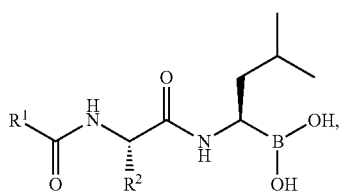

wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H;
(c) crystallizing the boronic ester of Formula I from a solution of the boronic ester of Formula V

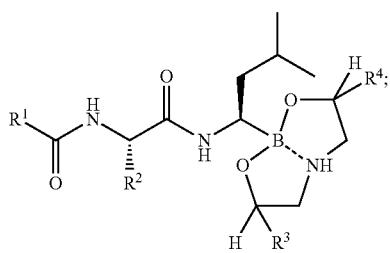

I and
(d) converting the boronic ester of Formula I into the boronic acid of Formula IA.

Embodiment 57

A Process for Preparing a Boronic Acid of Formula IA

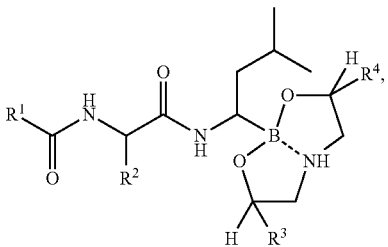

IA wherein
$R^1$ is 2-(6-phenyl)pyridinyl and $R^2$ is (1R)-1-hydroxyethyl, or $R^1$ is 2-pyrazinyl and
$R^2$ is benzyl;
comprising the steps of:
(a) preparing a boronic ester of Formula V wherein
  $R^1$ is 2-(6-phenyl)pyridinyl, $R^2$ is (1R)-1-hydroxyethyl, and $R^3$ and $R^4$ are H;
  $R^1$ is 2-(6-phenyl)pyridinyl, $R^2$ is (1R)-1-hydroxyethyl, and $R^3$ and $R^4$ are methyl; or
  $R^1$ is 2-pyrazinyl, $R^2$ is benzyl, and $R^3$ and $R^4$ are H;

(b) crystallizing the boronic ester of Formula I from a solution of the boronic ester of Formula V

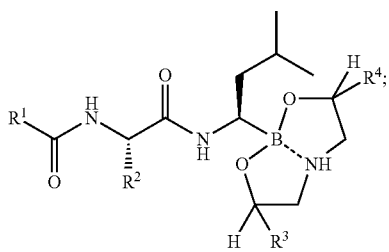

I and (c) converting the boronic ester of Formula I into the boronic acid of Formula IA.

Embodiment 58

A Process for Preparing a Boronic Acid of Formula IA

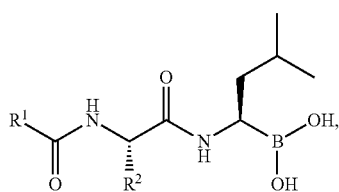

IA wherein
  $R^1$ is 2-(6-phenyl)pyridinyl and $R^2$ is (1R)-1-hydroxyethyl, or $R^1$ is 2-pyrazinyl and
  $R^2$ is benzyl;
comprising the steps of:
  (a) coupling a compound of Formula II

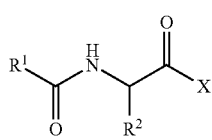

II with an amine of Formula III

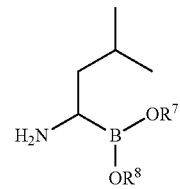

III to form an amide of Formula IV

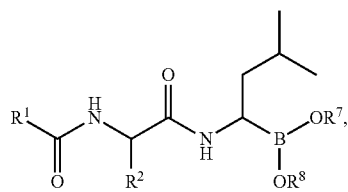

IV wherein

X is OH or a leaving group; and $R^7$ and $R^8$ are independently chosen from optionally substituted $C_{1-6}$alkyl, optionally substituted $C_{6-10}$aryl, optionally substituted $C_{7-16}$arylalkyl, optionally substituted $C_{3-11}$cycloalkyl, optionally substituted $C_{4-17}$cycloalkylalkyl, optionally substituted 3-15 membered heterocycloalkyl, optionally substituted 4-21 membered heterocycloalkylalkyl, optionally substituted 5-15 membered heteroaryl, and optionally substituted 6-21 membered heteroarylalkyl, or $R^7$ and $R^8$, together with the boron and oxygen atoms to which they are attached, form an optionally substituted 5-10 membered carbon-containing ring having 0-2 additional heteroatoms chosen from nitrogen, oxygen and sulfur;

(b) if the amide of Formula IV is not a boronic ester of Formula V, converting the amide of Formula IV into a boronic ester of Formula V

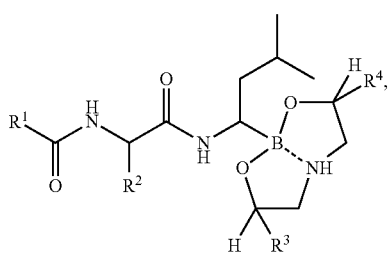

V wherein
  $R^1$ is 2-(6-phenyl)pyridinyl, $R^2$ is (1R)-1-hydroxyethyl, and $R^3$ and $R^4$ are H;
  $R^1$ is 2-(6-phenyl)pyridinyl, $R^2$ is (1R)-1-hydroxyethyl, and $R^3$ and $R^4$ are methyl; or
  $R^1$ is 2-pyrazinyl, $R^2$ is benzyl, and $R^3$ and $R^4$ are H;

(c) crystallizing the boronic ester of Formula I from a solution of the boronic ester of Formula V

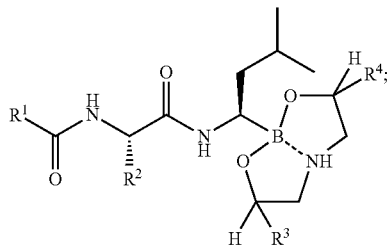

and
(d) converting the boronic ester of Formula I into the boronic acid of Formula IA.

Embodiment 59

A Process for Preparing a Boronic Acid of Formula IA

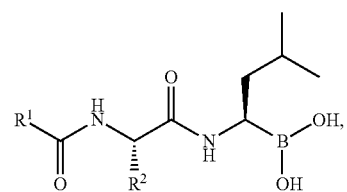

wherein
$R^1$ is 2-(6-phenyl)pyridinyl and $R^2$ is (1R)-1-hydroxyethyl, or $R^1$ is 2-pyrazinyl and
$R^2$ is benzyl;
comprising the steps of
(a) crystallizing a boronic ester of Formula I from a solution of a boronic ester of Formula V

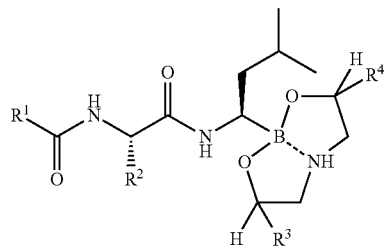

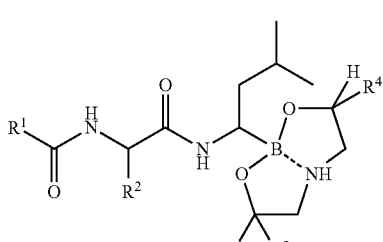

wherein
$R^1$ is 2-(6-phenyl)pyridinyl, $R^2$ is (1R)-1-hydroxyethyl, and $R^3$ and $R^4$ are H;
$R^1$ is 2-(6-phenyl)pyridinyl, $R^2$ is (1R)-1-hydroxyethyl, and $R^3$ and $R^4$ are methyl; or
$R^1$ is 2-pyrazinyl, $R^2$ is benzyl, and $R^3$ and $R^4$ are H; and
(b) converting the boronic ester of Formula I into the boronic acid of Formula IA.

Embodiment 60

The process of any of Embodiments 53 to 59, wherein $R^1$ is 2-(6-phenyl)pyridinyl, $R^2$ is (1R)-1-hydroxyethyl, and $R^3$ and $R^4$ are H.

Embodiment 61

The process of any of Embodiments 53 to 59, wherein $R^1$ is 2-(6-phenyl)pyridinyl, $R^2$ is (1R)-1-hydroxyethyl, and $R^3$ and $R^4$ are methyl.

Embodiment 62

The process of any of Embodiments 53 to 59, wherein $R^1$ is 2-pyrazinyl, $R^2$ is benzyl, and $R^3$ and $R^4$ are H.

Embodiment 63

A Process for Purifying a Compound of Formula VI

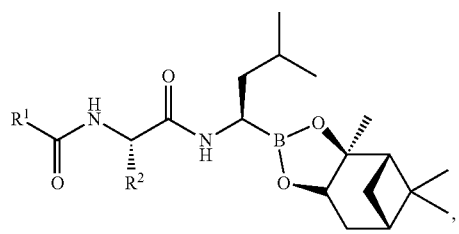

wherein
$R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) converting the compound of Formula VI into the boronic ester of Formula VII

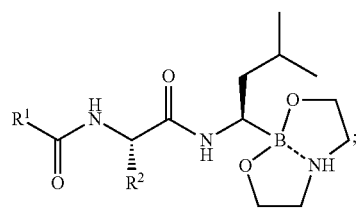

(b) crystallizing the boronic ester of Formula VII from solution;

(c) isolating the crystallized boronic ester of Formula VII from the solution; and (d) converting the isolated boronic ester of Formula VII back into the compound of Formula VI.

Embodiment 64

The process of Embodiment 63, wherein R¹ is 2-(6-phenyl)pyridinyl and R² is (1R)-1-hydroxyethyl.

Embodiment 65

The process of Embodiment 63, wherein R¹ is 2-pyrazinyl and R² is benzyl.

Embodiment 66

A Process for Purifying a Compound of Formula VIII

VIII

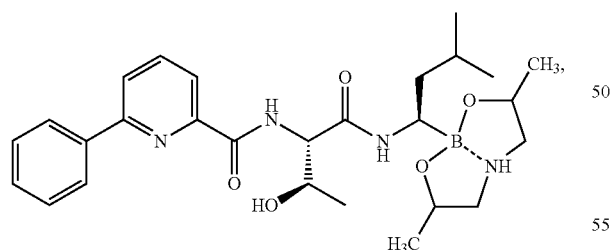

comprising the steps of:

(a) converting the compound of Formula VIII into the boronic ester of Formula IX

IX

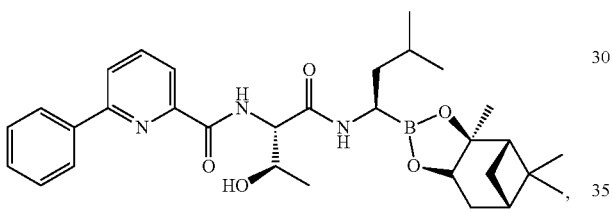

(b) crystallizing the boronic ester of Formula IX from solution;

(c) isolating the crystallized boronic ester of Formula IX from the solution; and (d) converting the isolated boronic ester of Formula IX back into the compound of Formula VIII.

Embodiment 67

A Boronic Ester of Formula IX

IX

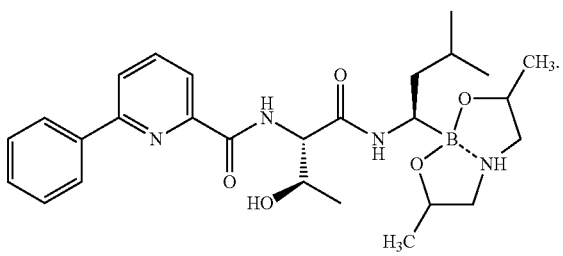

Embodiment 68

A Boronic Ester of Formula X

X

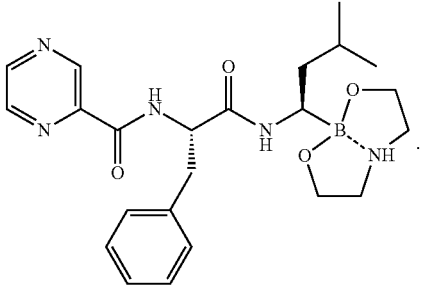

Embodiment 69

A Boronic Ester of Formula XI

XI

EXAMPLES

Methodology and Protocols.
Representative analytical conditions are provided below.

---

Chemical purity of (1R)-1-[(3aS,4S,6S,7aR)-hexahydro-3a,5,5-trimethyl-4,6-methano-1,3,2-benzodioxaborol-2-yl]-3-methylbutylamine by Gas Chromatography (GC)

| | |
|---|---|
| Column | Agilent HP-5, 3 μm film, 30 m × 0.53 mm |
| Injector temperature | 250° C. |
| Injection mode | splitless |
| Injection volume | 0.2 μL |
| Detection | FID at 300° C. |
| Flow | 6.0 mL/minute, constant flow |

| | Rate (° C./min.) | ° C. | Time (min.) |
|---|---|---|---|
| Oven program | | 60 | 0 |
| | 20 | 250 | 5 |

| | |
|---|---|
| Sample solution preparation | Accurately weigh about 10 mg of sample and quantitatively transfer to 10 mL volumetric flask. Completely dissolve the sample and dilute to volume using dichloromethane. |
| Standard solution preparation | Accurately weigh about 10 mg of (1R)-1-[(3aS,4S,6S,7aR)-hexahydro-3a,5,5-trimethyl-4,6-methano-1,3,2-benzodioxaborol-2-yl]-3-methylbutylamine and quantitatively transfer to 10 mL volumetric flask. Completely dissolve and dilute to volume using dichloromethane. |
| Procedure | Inject each solution in the following order: blank, standard solution, blank, duplicate sample solution, standard solution. |
| System suitability | Resolution between (1R)-1-[(3aS,4S,6S,7aR)-hexahydro-3a,5,5-trimethyl-4,6-methano-1,3,2-benzodioxaborol-2-yl]-3-methylbutylamine and the nearest eluting peak is greater than 1.5 |
| Retention times | (1R)-1-[(3aS,4S,6S,7aR)-hexahydro-3a,5,5-trimethyl-4,6-methano-1,3,2-benzodioxaborol-2-yl]-3-methylbutylamine = 11.2 minutes |
| Calculations | Integrate the area under each peak of interest not observed in the blank solution |

---

Chiral purity of (1R)-1-[(3aS,4S,6S,7aR)-hexahydro-3a,5,5-trimethyl-4,6-methano-1,3,2-benzodioxaborol-2-yl]-3-methylbutylamine by GC

| | |
|---|---|
| Column | Astec, β-DM, 0.25 μm film |
| Column dimensions | 30 m × 0.25 mm |
| Injector Temperature | 200° C. |
| Detector Temperature | 250° C. |
| Flow rate | 1.0 mL/minute, Constant Flow |
| Detector | FID |
| Injection volume | 1 μL |
| Injection mode | Split, 20:1 |

| | Rate (° C./min.) | ° C. | Time (min.) |
|---|---|---|---|
| Oven program | | 150 | 1 |
| | 2.5 | 200 | 2 |

| | |
|---|---|
| Sample solution preparation | Add approximately 1 mL of dichloromethane to 10 mg of sample. Add 200 μL pentafluoroproprionic anhydride (PFPA) and cap the vial. Heat at 60° C. for 20 minutes. Remove the solvent under a gentle stream of nitrogen. Reconstitute the residue in 1 mL of dichloromethane. |
| Procedure | Single injection of each solution in the following order: blank, duplicate sample solution. |
| System suitability | Resolution between (1R)-1-[(3aS,4S,6S,7aR)-hexahydro-3a,5,5-trimethyl-4,6-methano-1,3,2-benzodioxaborol-2-yl]-3-methylbutylamine and the corresponding enantiomer peak is greater than 1.5 |
| Retention times | (1R)-1-[(3aS,4S,6S,7aR)-hexahydro-3a,5,5-trimethyl-4,6-methano-1,3,2-benzodioxaborol-2-yl]-3-methylbutylamine = 14.4 minutes<br>Corresponding enantiomer peak = 14.6 minutes |
| Calculations | Integrate the area under each peak of interest not observed in the blank solution |

---

Chemical purity of [(1R)-1-[[(2S,3R)-3-Hydroxy-2-[[(6-phenylpyridin-2-yl)carbonyl]amino]-1-oxobutyl]amino]-3-methylbutyl]boronic acid by high performance liquid chromatography (HPLC)*

| | |
|---|---|
| Column | Waters Symmetry C18 |
| Column dimensions | 150 × 4.6 mm, 3.5 μm |
| Column temperature | 35° C. |
| Mobile phase A | 0.05% TFA in de-ionized water |
| Mobile phase B | 0.05% TFA acetonitrile |
| Flow rate | 1 mL/minute |
| Detector | UV @ 254 nm |
| Injection volume | 10 μL |

| | Time (min.) | % B |
|---|---|---|
| Gradient | 0 | 25 |
| | 2 | 25 |
| | 17 | 35 |
| | 30 | 90 |
| | 35 | 90 |
| | 35.1 | 25 |
| | 42 | 25 |

| | |
|---|---|
| Sample solution preparation | Prepare in duplicate. Dissolve 10 mg of sample in 10 mL of acetonitrile. |
| Standard solution preparation | Prepare an acetonitrile solution containing approximately 1 mg/mL of [(1R)-1-[[(2S,3R)-3-Hydroxy-2-[[(6-phenylpyridin-2-yl)carbonyl]amino]-1-oxobutyl]amino]-3-methylbutyl]boronic acid |
| Procedure | Single injection of each solution in the following order: standard solution, blank, sample solution, blank, standard solution. |
| System suitability | Retention time of [(1R)-1-[[(2S,3R)-3-Hydroxy-2-[[(6-phenylpyridin-2-yl)carbonyl]amino]-1-oxobutyl]amino]-3-methylbutyl]boronic acid is from 16 to 21 minutes.<br>Resolution between [(1R)-1-[[(2S,3R)-3-Hydroxy-2-[[(6-phenylpyridin-2-yl)carbonyl]amino]-1-oxobutyl]amino]-3-methylbutyl]boronic acid and the corresponding D-allo-threonine diastereomer is greater than 1.5. |
| Retention times | [(1R)-1-[[(2S,3R)-3-Hydroxy-2-[[(6-phenylpyridin-2-yl)carbonyl]amino]-1-oxobutyl]amino]-3-methylbutyl]boronic acid = 18.6 minutes<br>Corresponding D-allo-threonine diastereomer = 17.8 minutes |
| Calculations | Integrate the area under each peak of interest |

*Note:
Chemical purity of 6-(2S,3R)-N-[(1R)-1-(1,3,6,2-dioxazaborocan-2-yl)-3-methylbutyl}-3-hydroxy-2-{(6-phenylpyridin-2-yl)formamido]butanamide, (2S)-N-[(1R)-1-(1,3,6,2-dioxazaborocan-2-yl)-3-methylbutyl]-3-phenyl-2-(pyrazin-2-ylformamido)propanamide, and bortezomib were also determined using this method (the boronic esters hydrolyze to the corresponding boronic acids under the analytical conditions employed and the purity of the resulting boronic acids was determined).
Retention times of bortezomib and bortezomib diastereomer = 11.9 minutes and 14.2 minutes, respectively.

| | |
|---|---|
| \multicolumn{2}{c}{Chiral purity of [(1R)-1-[[(2S,3R)-3-Hydroxy-2-[[(6-phenylpyridin-2-yl)carbonyl]amino]-1-oxobutyl]amino]-3-methylbutyl]boronic acid by high performance liquid chromatography (HPLC)*} |
| Column | Chiralpak IC (Vendor: Chiral Tchnologies, Inc) |
| Column dimensions | 250 × 4.6 mm, 5 µm |
| Column temperature | ambient |
| Mobile phase | 92:8 hexanes:isopropyl alcohol (IPA) |
| Flow rate | 1 mL/minute |
| Run time | 30 minutes |
| Detector | UV @ 254 nm |
| Injection volume | 10 µL |
| Sample solution preparation | Dissolve 10 mg of sample in 10 mL of 9:1 IPA:methanol. Prepare in duplicate. |
| Procedure | Inject solutions immediately after preparation. If the HPLC autosampler tray can be thermostatted, set the temperature to 5° C. Use amber glass HPLC vials if the autosampler tray is not shielded from light. Make a single injection of each solution in the following order: blank, sample solution, blank. |
| System suitability | Retention time of [(1S)-1-[[(2S,3R)-3-Hydroxy-2-[[(6-phenylpyridin-2-yl)carbonyl]amino]-1-oxobutyl]amino]-3-methylbutyl]boronic acid is from 8 to 12 minutes. Resolution between [(1R)-1-[[(2S,3R)-3-Hydroxy-2-[[(6-phenylpyridin-2-yl)carbonyl]amino]-1-oxobutyl]amino]-3-methylbutyl]boronic acid and the corresponding (1S) isomer is greater than 1.5. |
| Retention times | [(1S)-1-[[(2S,3R)-3-Hydroxy-2-[[(6-phenylpyridin-2-yl)carbonyl]amino]-1-oxobutyl]amino]-3-methylbutyl]boronic acid = 10.3 minutes<br>[(1R)-1-[[(2S,3R)-3-Hydroxy-2-[[(6-phenylpyridin-2-yl)carbonyl]amino]-1-oxobutyl]amino]-3-methylbutyl]boronic acid = 12.8 minutes<br>[(1R)-1-[[(2R,3R)-3-Hydroxy-2-[[(6-phenylpyridin-2-yl)carbonyl]amino]-1-oxobutyl]amino]-3-methylbutyl]boronic acid = 19.6 minutes |
| Calculations | Integrate the area under the [(1S)-1-[[(2S,3R)-3-Hydroxy-2-[[(6-phenylpyridin-2-yl)carbonyl]amino]-1-oxobutyl]amino]-3-methylbutyl]boronic acid and [(1R)-1-[[(2S,3R)-3-Hydroxy-2-[[(6-phenylpyridin-2-yl)carbonyl]amino]-1-oxobutyl]amino]-3-methylbutyl]boronic acid peaks. Calculate the % area of [(1S)-1-[[(2S,3R)-3-Hydroxy-2-[[(6-phenylpyridin-2-yl)carbonyl]amino]-1-oxobutyl]amino]-3-methylbutyl]boronic acid with respect to [(1R)-1-[[(2S,3R)-3-Hydroxy-2-[[(6-phenylpyridin-2-yl)carbonyl]amino]-1-oxobutyl]amino]-3-methylbutyl]boronic acid. |

*Note:
Chiral purity of 6-(2S,3R)-N-[(1R)-1-(1,3,6,2-dioxazaborocan-2-yl)-3-methylbutyl]-3-hydroxy-2-{(6-phenylpyridin-2-yl)formamido]butanamide was also determined using this method. 1-2 drops of 0.1% TFA/water was added to the sample prior to injection to hydrolyze the ester to the corresponding boronic acid, and the chiral purity of the resulting boronic acid was determined.

Preparation 1. Preparation of (1R)-1-[(3aS,4S,6S,7aR)-hexahydro-3a,5,5-trimethyl-4,6-methano-1,3,2-benzodioxaborol-2-yl]-3-methylbutylamine hydrochloride salt A 20 liter Chemglass® jacketed reactor equipped with overhead stirring, nitrogen sweep, thermocouple with temperature readout, a 1 liter addition funnel, sub-surface gas dispersion tube and auxiliary heater/chiller was charged with 8.0 liters of anhydrous methyl tert-butyl ether. The chiller was set to −40° C. The solvent was cooled to −31.3° C. with agitation. Next, 714.4 g (19.71 mol, 5.0 eq) of HCl(g) was added subsurface over 1.75 hours while maintaining the temperature between −25.7 and −10.0° C. Next, 1.6235 kg (3.964 mol) of N,N-Bis(trimethylsilyl)-(1R)-1-[(3aS,4S,6S,7aR)-hexahydro-3a,5,5-trimethyl-4,6-methano-1,3,2-benzodioxaborol-2-yl]-3-methylbutylamine (obtained by a method similar to that disclosed in U.S. Patent Publication No. 2005/0240047 (Pickersgill et al.), was dissolved in 2.1 liters of methyl tert-butyl ether. Next, the solution was added to the HCl solution over 40 minutes while maintaining the reaction temperature between −25 and −10° C. After addition was complete the reaction was warmed to ambient temperature and the chiller was turned off The reaction was allowed to warm to ambient temperature and was stirred overnight. GC analysis the next morning indicated that the reaction was complete. Next, the reaction was concentrated on the rotary evaporator to a volume of 1-2 liters. 3 liters of heptanes were added to the mixture and the distillation continued to remove 3 more liters of distillate. Next, 6 more liters of heptanes were added portion wise while removing 1 more liter of distillate. The product mixture was transferred to the 20 liter Chemglass® jacketed reactor equipped as previously described and allowed to slowly stir overnight at ambient temperature. The next morning the mixture was cooled to −15 and −10° C. and allowed to agitate for 1 hour. The product was filtered through a medium glass sintered filter funnel equipped with a #1 Whatman® filter paper. The product cake was washed with 2 liters of cold (0° C.) heptane and dried in an oven under vacuum (29 mmHg) at 35° C. and purged with nitrogen. The yield was 996.0 g (84%) with a purity of 93.9 A %, and a diastereomer ratio of 98.75:1.25 (d.e.=97.5%).

Example 1

Preparation of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X)

Step A. Preparation of 6-Phenyl-pyridine-2-carbonyl chloride

A 2-L three neck round bottomed flask equipped with an overhead stirrer, thermocouple, heating mantle with digital temperature controller, condenser and nitrogen inlet/outlet was charged with 100.0 g (0.502 mol) of 6-phenyl-2-pyridinecarboxylic acid and 1500 mL of toluene (Kf<0.02 wt %) then warmed to 40° C. Thionyl chloride (110 mL; 1.51 mol, 3 eq) was then added to the thin slurry via addition funnel over 20 minutes. The thin slurry was heated to 75° C. and stirred overnight (typically 10-16 hr), until it became a clear solution. Reaction was assayed via HPLC for conversion as the methyl ester derivative. After cooling the reaction mixture to room temperature the solvent and excess thionyl chloride were removed in vacuo as follows: Reaction mixture was stripped under full vacuum at 40° C. (bath temperature) to approximately ⅓ its original volume (~500 ml) and then (1000 ml) of fresh toluene was added. Concentration was continued, again stripping to ⅓ original volume (~500 ml) followed by re-dilution with 1000 ml of fresh toluene. The total amount of toluene removed was ~2000 mL.

Step B. Preparation of (2S,3R)-3-Hydroxy-2-[oxo-2-(6-phenyl-pyridin-2-yl)-ethyl}-butyric acid (i.e., acid of Formula II, wherein $R^1$ is 2-(6-phenyl)pyridinyl and $R^2$ is (R)-1-hydroxyethyl)

A 3-L three neck round bottomed flask was equipped with an overhead stirrer, thermocouple, pressure equalizing dropping funnel, nitrogen inlet/outlet and ice/water cooling bath.

L-threonine, 62.8 g (0.53 mol) was added, followed by 117 g (1.1 mol) of sodium carbonate and 1500 mL of deionized water. The aqueous solution was cooled to 10.0° C. During this time the addition funnel was charged with the acid chloride/toluene solution prepared in Step A. This toluene solution was added dropwise to the aqueous reaction over approximately 10 minutes at ~10° C. Once the addition was complete, the reaction was warmed to room temperature (~22-25° C.) and vigorously stirred until it was shown to be complete by HPLC analysis (typically ~3 hr). The reaction mixture was then transferred to a separatory funnel and the two layers were separated. The lower aqueous phase was then recharged to the reaction flask. Methanol (800 mL) was then added to the mixture followed by pH adjustment (target pH=1-2) with 2.5M HCl (~850 mL), keeping the temperature at 15-20° C. Some off-gassing occurred at ~pH=5, followed by precipitation of the product at pH=3. The slurry was allowed to stir at room temperature for 30 minutes post pH adjustment. The white solid was collected by vacuum filtration, (mother liquor losses <2 mg/mL), washed with deionized water (2×500 ml) then dried in a vacuum oven at 40° C. with a nitrogen sweep to a constant weight to provide 141 g (0.471 mol, 94%) of the title compound with an HPLC purity of 99 A % (95 wt %). $^1$H NMR (d6-DMSO, 400 MHz) δ 12.9 (s, 1H, b), 8.71 (d, 1H, J=9.16 Hz), 8.23 (d, 1H, J=7.24 Hz), 8.1 (m, 3H), 8.03 (d, 1H, J=7.0 Hz), 7.55 (m, 3H), 5.34 (s, 1H, b), 4.46 (dd, 1H, J=2.52, 9.16 Hz), 4.34 (dd, 1H, J=1.92, 6.24 Hz), 1.15 (d, 3H, J=6.4 Hz).

Step C. Preparation of N-[(1S,2R)-1[[[(1R)-1-1[(3aS,4S,6S,7aR)-hexahydro-3a,5,5-trimethyl-4,6-methano-1,3,2-benzodioxaborol-2-yl[-3-methylbutyl]amino]carbonyl]2-hydroxypropyl]-6-phenyl-2-pyridinecarboxamide (i.e., (1S,2S,3R,5S)-(+)-2,3-pinanediol boronic ester of Formula IV, wherein $R^1$ is 2-(6-phenyl)pyridinyl and $R^2$ is (R)-1-hydroxyethyl)

A 10 liter jacketed reaction vessel equipped with a thermocouple, stirring shaft with impeller, addition funnel, and low temperature recirculating bath was charged with 156.1 g (0.52 mol, 1.0 eq) of (2S,3R)-3-Hydroxy-2-[oxo-2-(6-phenyl-pyridin-2-yl)-ethyl}-butyric acid, 218.8 g (0.575 mol, 1.1 eq) of O-(7-azabenzotriazol-1-yl)-N,N,N'N'-tetramethyluronium hexafluorophosphate (HATU), 157.7 g (0.522 mol, 1.0 eq) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (98.8:1.2 mixture of isobutyl diastereomers (R:S))], and 2355 mL of N,N-dimethylformamide (DMF). Agitation was begun and the solids dissolved before cooling the reaction mixture to <–25.0° C. Diisopropylethylamine (218.6 mL, 162.2 g, 1.25 mol, 2.4 eq) was charged to the addition funnel and then added dropwise to the reaction mixture over 30~ minutes at –25° C. to –30° C. Once addition was complete the reaction was stirred at –30° C. for six hours. In a separate twenty-two liter four-neck reaction flask equipped with an overhead stirrer and thermocouple was charged 3925 mL of DI water and 3925 mL of ethyl acetate. The reaction mixture was transferred to this flask over five minutes at RT. The lower aqueous layer was separated and discarded. A solution of 393 g of sodium phosphate monobasic, monohydrate in 3925 mL of DI water was prepared and the organic phase was washed with this solution. The lower aqueous phase was again removed and discarded. A solution of 376.9 g of sodium bicarbonate in 4710 mL of DI water was prepared and the organic phase was washed with this solution which had been split into two portions. Once again the lower aqueous phase was separated and discarded. A saturated sodium chloride solution was prepared using 481.4 g of sodium chloride in 3140 mL of DI water and the organic phase was washed with this solution, the layers were separated and the lower aqueous phase discarded. Norit GAC 1240+ carbon (157 g) was added to the organic phase and the suspension was stirred at RT overnight (13.8 hours). The carbon was removed by vacuum filtration through Whatman GF/C glass fiber filter paper, then washed with 350 mL of ethyl acetate. The filtrate was concentrated to a foam on a rotary evaporator at under vacuum with a 33-44° C. bath temperature to provide 231.5 g (0.422 mol, 80.9%) of the title compound as a foam with a chemical purity of 96.4%. The level of threonine isomer was 1.16 A %. $^1$H NMR (d6-DMSO, 400 MHz) δ 8.98 (d, b, 1H, J=2.99 Hz), 8.76 (d, 1H, J=8.55 Hz), 8.2 (m, 3H), 8.11 (t, 1H, J=7.71 Hz), 8.02 (d, 1H, J=7.54 Hz), 7.54 (m, 3H), 5.26 (d, 1H, J=4.95 Hz), 4.49 (dd, 1H, J=4.22, 8.52 Hz), 4.13 (m, 2H), 2.6 (m, b, 1H), 2.19 (m, b, 1H), 2.02 (m, b, 1H), 1.83 (t, 1H, J=5.38 Hz), 1.75 (s, b, 1H), 1.68 (m, b, 1H), 1.62 (d, 1H, J=13.9 Hz), 1.36 (d, 1H, J=10.05 Hz), 1.3 (m, b, 3H), 1.22 (d, 6H, J=11.65 Hz), 1.12 (d, 3H, J=6.26 Hz), 0.84 (d, 6H, J=6.57 Hz), 0.79 (s, 3H).

Note: The inventors have determined that the Norit GAC 1240+ carbon decolorization/purification step may be omitted entirely, since the impurities carried forward are removed in Step D (and optional Step E), and the yield is increased by about 10% (see Example 1A). This is another advantage of the present invention.

Step D. Preparation of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X)

Option 1—Two Step Procedure

A twelve liter four neck round bottom flask was equipped with an overhead stirrer, thermocouple and nitrogen outlet before being charged with a solution of 229.8 g (0.42 mol, 1 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide in 2310 mL of methanol. To this was added 3465 mL of n-heptane, 108 g (1.06 mol, 2.5 eq) of (2-methylpropyl)boronic acid and a solution of 70 mL (84 g, 0.85 mol, 2.0 eq) of 37% hydrochloric acid in 353 mL of DI water. Agitation was begun and the two phase mixture was stirred at RT for 16 hours. The reaction mixture was transferred in portions to a four liter separatory funnel and the lower methanolic phase was separated and returned to the reaction flask. The upper heptane layer was discarded. A fresh charge of 3465 mL of n-heptane was added to the reaction and the reaction was agitated at RT for an additional two hours. Agitation was stopped and the phases were separated and the lower methanolic layer was extracted with n-heptane (2×4600 mL). The heptane phases were discarded and the methanolic phase was concentrated in vacuo with a bath temperature of 40° C. Ethyl acetate (4620 mL) was charged to the evaporation flask and the sticky yellow residue was dissolved before transferring to a twelve-liter reaction flask. A solution of 665.4 g of sodium bicarbonate in 7650 mL of DI water was prepared and used to wash the ethyl acetate layer in two portions (1×4000 mL and 1×3850 mL). A solution of 1059.7 g of sodium chloride in 2700 mL of DI water was prepared and then used to wash the ethyl acetate phase.

After separation of layers the ethyl acetate layer was treated with 47.3 g (0.45 mol, 1.1 eq) of diethanolamine The mixture was allowed to stir at RT overnight. Precipitated solids were collected by vacuum filtration using a closed filtration flask and the wet cake was washed with 500 mL of ethyl acetate. The sealed filter funnel was transferred to a glove box where it was opened and the 481.8 g of wet cake was transferred to two pyrex drying trays which were then placed into a vacuum oven. The product was dried to a constant weight at 23.5 in of Hg and 50° C. over 27 hours to provide 179.7 g (0.372 mol, 88.8%) of the title compound with a chemical purity of 98.6% and a chiral purity of 98.8% de. $^1$H NMR (d6-DMSO, 400 MHz) δ 8.8 (d, 1H, J=8.52 Hz), 8.2 (m, 3H), 8.1 (t, 1H, J=7.68 Hz), 8.0 (dd, 1H, J=6.7, 0.9 Hz), 7.5 (m, 3H), 7.2 (d, 1H), 6.5 (t, b, 1H), 5.1 (d, 1H, J=4.92 Hz), 4.5 (dd, 1H), 4.2 (m, 1H), 3.6 (m, 2H), 3.5 (m, 2H), 3.1 (m, 1H), 3.0 (m, 2H), 2.7 (m, 2H), 1.6 (m, 1H), 1.3 (m, 1H), 1.2 (m, 1H), 1.1 (d, 3H, J=6.32 Hz), 0.8 (2d, 6H, J=6.68, 6.52 Hz).

Option 2—One Step Procedure:

A 50 mL three neck round bottom flask was equipped with a thermocouple, stir bar, nitrogen inlet/outlet, heating mantle and temperature controller. The flask was charged with 2.0 g (3.65 mmol, 1.0 eq) of N-[(1S,2R)-1[[[(1R)-1-[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide and 20 mL of MTBE. The reaction mixture was stirred for approximately 10 minutes until all the solids dissolved. Diethanolamine (0.44 mL, 0.48 g, 4.57 mmol, 1.25 eq) was charged via syringe, along with 2 drops of methanesulfonic acid, to the light yellow solution and the mixture was heated to 50° C. After approximately 30 minutes a white precipitate began to form. Stirring was continued overnight before cooling to room temperature. The solids were collected by vacuum filtration, washed with MTBE (1×20 mL) then dried under vacuum at 60° C. overnight to give 0.92 g (1.9 mmol, 52%) of the title compound as a white solid with a chemical purity of 91.9% and a chiral purity of >99.5% de.

Step E (optional). Purification of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X). A two liter four neck round bottom flask was equipped with an overhead stirrer, thermocouple, condenser, heating mantle, temperature controller and nitrogen outlet before being charged with 175 g (0.363 mol) of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide and 1400 mL (8 volumes) of 95% ethanol. Agitation was begun and the resultant suspension was heated to 75.7° C. over 21 minutes. Once at temperature the solution was stirred for 80 minutes at 74.9-75.8° C. before cooling to 2.7° C. over 80 minutes. The reaction slurry was then stirred at 2.2-6.0° C. overnight (17 hours) to fully crystallize the product. Precipitated solids were collected by vacuum filtration using a closed filtration flask and the wet cake was washed with 350 mL of 95% ethanol. The sealed filter funnel was transferred to a glove box where it was opened and the 203.8 g of wet cake was transferred to a pyrex drying tray which was then placed into a vacuum oven. The product was dried to a constant weight at 23.5 in of Hg and 50° C. over 19 hours to provide 147.3 g (0.306, mol, 84.2%) of the title compound with a chemical purity of 99.76% and an optical purity of >99.8% de.

Example 1A

Optimized Preparation of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X)

Step A. Preparation of 6-Phenyl-pyridine-2-carbonyl chloride

A 1 L three neck round bottomed flask equipped with a stir bar, thermocouple, heating mantle with digital temperature controller, condenser and nitrogen inlet/outlet was charged with 100 g (502 mmol) of 6-phenyl-2-pyridinecarboxylic acid and 500 mL of toluene (Kf<0.02 wt %). Thionyl chloride (119.4 g, 73.2 mL; 1.04 mol, 2 eq) was then added to the thin slurry via addition funnel over 5 minutes. The thin slurry was heated to 75° C. and stirred overnight (typically 10-22 hr), until it became a clear solution. Reaction was assayed via HPLC for conversion as the methyl ester derivative. After cooling the reaction mixture to room temperature the solvent and excess thionyl chloride were removed in vacuo as follows: Reaction mixture was stripped under full vacuum at 40° C. (bath temperature) to approximately ⅓ its original volume (~160 ml) and then (500 ml) of fresh toluene was added. Concentration was continued, again stripping to ⅓ original volume (~160 ml) followed by re-dilution with 500 ml of fresh toluene and concentration to dryness to yield 110.5 g (quantitative) of the acid chloride as a yellow oil. This oil was dissolved in 500 mL of fresh toluene and used in Step B.

Step B. Preparation of (2S,3R)-3-Hydroxy-2-[oxo-2-(6-phenyl-pyridin-2-yl)-ethyl}-butyric acid (i.e., acid of Formula II, wherein $R^1$ is 2-(6-phenyl)pyridinyl and $R^2$ is (R)-1-hydroxyethyl). A 2 L four neck round bottomed flask was equipped with an overhead stirrer, thermocouple, pressure equalizing dropping funnel, nitrogen inlet/outlet and ice/water cooling bath. L-threonine, 62.79 g (527 mmol, 1.05 eq) was added, followed by 117.05 g (1.1 mol, 2.2 eq) of sodium carbonate and 1 L of deionized water. The addition funnel was charged with the acid chloride/toluene solution prepared in Step A. This toluene solution was added dropwise to the aqueous reaction over approximately 20 minutes. The reaction exothermed to 28° C. over the next 1.5 hours. The reaction was allowed to stir overnight at room temperature for convenience, although previous small scale runs indicated it would be complete after 3 hours. The reaction mixture was then transferred to a separatory funnel and the two layers were separated. The lower aqueous phase was then recharged to the reaction flask. Methanol (800 mL) was then added to the mixture followed by pH adjustment (2.3) with 64 M HCl, keeping the temperature at 10-20° C. Some off-gassing occurred at ~pH=5, followed by precipitation of the product at pH=3. The slurry was allowed to stir at room temperature for 2 hours post pH adjustment. The white solid was collected by vacuum filtration, (mother liquor losses <2 mg/mL), washed with deionized water (1×100 mL) then dried in a vacuum oven at 50° C. with a nitrogen sweep to a constant weight. A yield of 126.15 g (420 mmol, 83.7%) was obtained with an HPLC purity of (97.1 A %). $^1$H NMR (d6-DMSO, 400MHz) δ 12.9 (s, 1H, b), 8.71 (d, 1H, J=9.16 Hz), 8.23 (d, 1H, J=7.24 Hz), 8.1 (m, 3H), 8.03 (d, 1H, J=7.0 Hz), 7.55 (m, 3H), 5.34 (s, 1H, b), 4.46 (dd, 1H, J=2.52, 9.16 Hz), 4.34 (dd, 1H, J=1.92, 6.24 Hz), 1.15 (d, 3H, J=6.4 Hz).

Step C. Preparation of N-[(1S,2R)-1[[[(1R)-1-1[(3aS,4S, 6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (i.e., (1S, 2S,3R,5S)-(+)-2,3-pinanediol boronic ester of Formula IV, wherein $R^1$ is 2-(6-phenyl)pyridinyl and $R^2$ is (R)-1-hydroxyethyl). A 2.0 liter round bottom flask equipped with a thermocouple, overhead stirrer, addition funnel and cooling bath was charged with 82.1 g (0.265 mol, 1.0 eq) of 97% (2S,3R)-3-Hydroxy-2-[oxo-2-(6-phenyl-pyridin-2-yl)-ethyl}-butyric acid, 105.9 g (0.278 mol, 1.05 eq) of HATU, 80.0 g (0.265 mol, 1.0 eq) of 99.9% (1R)-1-[(3aS,4S,6S,7aR)-hexahydro-3a,5,5-trimethyl-4,6-methano-1,3,2-benzodioxaborol-2-yl]-3-methylbutylamine hydrochloride salt and 400 mL of N,N-dimethylformamide (DMF, 5 vol). Agitation was begun and the solids dissolved before cooling the reaction mixture to 0° C. Diisopropylethylamine (102.8 g, 2.385 mol, 3.0 eq) was charged to the addition funnel and then added drop-wise to the reaction mixture over 30 minutes at 0-7° C. Once addition was complete the reaction was stirred at 0° C. for one hour until an in process analysis indicated <2 A % (2S,3R)-3-Hydroxy-2-[oxo-2-(6-phenyl-pyridin-2-yl)-ethyl}-butyric acid remaining. In a separate five liter four-neck reaction flask equipped with an overhead stirrer and thermocouple was charged 2000 mL of DI water and 2000 mL of ethyl acetate. The reaction mixture was transferred to this flask over five minutes at RT. The lower aqueous layer was separated and discarded. The upper organic layer was washed with 2.0 L each of 10% aqueous sodium phosphate monobasic, saturated aqueous sodium bicarbonate and brine before drying over sodium sulfate, filtering and concentrating to dryness in vacuo at 33-44° C. bath temperature to yield a light brown foam. The 143.0 g (0.422 mol, 98.6%) of the title compound thus obtained was carried forward to the next reaction as a foam with a chemical purity of 92.2%. $^1$H NMR (d6-DMSO, 400 MHz) δ 8.98 (d, b, 1H, J=2.99 Hz), 8.76 (d, 1H, J=8.55 Hz), 8.2 (m, 3H), 8.11 (t, 1H, J=7.71 Hz), 8.02 (d, 1H, J=7.54 Hz), 7.54 (m, 3H), 5.26 (d, 1H, J=4.95 Hz), 4.49 (dd, 1H, J=4.22, 8.52 Hz), 4.13 (m, 2H), 2.6 (m, b, 1H), 2.19 (m, b, 1H), 2.02 (m, b, 1H), 1.83 (t, 1H, J=5.38 Hz), 1.75 (s, b, 1H), 1.68 (m, b, 1H), 1.62 (d, 1H, J=13.9 Hz), 1.36 (d, 1H, J=10.05 Hz), 1.3 (m, b, 3H), 1.22 (d, 6H, J=11.65 Hz), 1.12 (d, 3H, J=6.26 Hz), 0.84 (d, 6H, J=6.57 Hz), 0.79 (s, 3H).

Step D. Preparation of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X). A 5.0 liter four neck round bottom flask was equipped with an overhead stirrer, thermocouple and nitrogen outlet before being charged with a solution of 130.0 g (237 mmol, 1 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide in 650 mL of methanol (5 volumes). To this was added 1.3 L of n-heptane (10 volumes), 96.8 g (0.951 mol, 4.0 eq) of (2-methylpropyl) boronic acid and 120 mL (240 mmol, 1.0 eq) of 2N hydrochloric acid. Agitation was begun and the two phase mixture was stirred at RT for 20 hours. The reaction mixture was transferred to a separatory funnel and the phases were separated and the lower methanolic layer was extracted with n-heptane (1×1.0 L). The heptane phases were discarded and the methanolic phase was concentrated in vacuo with a bath temperature of 40° C. Ethyl acetate (1.0 L) was charged to the evaporation flask and the sticky yellow residue was dissolved before being washed with saturated aqueous sodium bicarbonate (1×1.0 mL) and brine (1×600 mL). After separation of the layers the ethyl acetate phase assayed at 88.7 A % by HPLC. Approximately 720 mL of this solution containing 73.5 g (66.2 g corrected, 160 mmol) of crude [(1R)-1-[[(2S, 3R)-3-Hydroxy-2-[[(6-phenylpyridin-2-yl)carbonyl]amino]-1-oxobutyl]amino]-3-methylbutyl]boronic acid (i.e., Compound 1) was transferred to a 2.0 L three-neck round bottom flask equipped with a stir bar, thermocouple and nitrogen outlet. Diethanolamine (16.82 g, 160 mmol) was charged and the mixture stirred for 1.5 hours at room temperature. Solids began to precipitate almost immediately. Precipitated solids were collected by vacuum filtration using a closed filtration flask and the wetcake was washed with 100 mL of ethyl acetate. The sealed filter funnel was transferred to a glove box where it was opened and the wetcake was transferred to a pyrex drying tray which was then placed into a vacuum oven. The product was dried to a constant weight at 23.5 in of Hg and 50° C. over 27 hours, providing 65 g (134.8 mmol, 84.2%) of the title compound with a chemical purity of 96.5%. $^1$H NMR (d6-DMSO, 400 MHz) δ 8.8 (d, 1H, J=8.52 Hz), 8.2 (m, 3H), 8.1 (t, 1H, J=7.68 Hz), 8.0 (dd, 1H, J=6.7, 0.9 Hz), 7.5 (m, 3H), 7.2 (d, 1H), 6.5 (t, b, 1H), 5.1 (d, 1H, J=4.92 Hz), 4.5 (dd, 1H), 4.2 (m, 1H), 3.6 (m, 2H), 3.5 (m, 2H), 3.1 (m, 1H), 3.0 (m, 2H), 2.7 (m, 2H), 1.6 (m, 1H), 1.3 (m, 1H), 1.2 (m, 1H), 1.1 (d, 3H, J=6.32 Hz), 0.8 (2d, 6H, J=6.68, 6.52 Hz).

Example 2

Preparation of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X) from (1R)-1-[(3aS,4S, 6S,7aR)-hexahydro-3a,5,5-trimethyl-4,6-methano-1, 3,2-benzodioxaborol-2-yl]-3-methylbutylamine hydrochloride salt of lower chiral purity Step C. Preparation of N-[(1S,2R)-1[[[(1R)-1-1 [(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]6-phenyl-2-pyridinecarboxamide (i.e., (1S,2S,3R,5S)-(+)-2,3-pinanediol boronic ester of Formula IV, wherein $R^1$ is 2-(6-phenyl)pyridinyl and $R^2$ is (R)-1-hydroxyethyl)

A 5-liter 4 necked round bottom flask equipped with a thermocouple, stirring shaft with impeller, addition funnel, and low temperature external cooling bath was charged with 205 g (0.68 mol, 1.0 eq) of (2S,3R)-3-Hydroxy-2-[oxo-2-(6-phenyl-pyridin-2-yl)-ethyl}-butyric acid, 285.5 g (0.75 mol, 1.1 eq) of HATU, 206 g (0.68 mol, 1.0 eq) of (1R)-1-[(3aS, 4S,6S,7aR)-hexahydro-3a,5,5-trimethyl-4,6-methano-1,3,2-benzodioxaborol-2-yl]-3-methylbutylamine hydrochloride salt (87:13 mixture of isobutyl diastereomers (R:S) (74% de)), and 3075 mL of N,N-dimethylformamide (DMF). Agitation was begun and the solids dissolved before cooling the reaction mixture to <−25.0° C. Diisopropylethylamine (285 mL, 211 g, 1.63 mol, 2.4 eq) was charged to the addition funnel and then added drop-wise to the reaction mixture over ~45 minutes at −25° C. to −40° C. Once addition was complete the reaction was stirred at <−30° C. overnight for convenience. In a separate twenty-two liter four-neck reaction flask equipped with an overhead stirrer and thermocouple was charged 5125 mL of DI water and 5125 mL of ethyl acetate. The reaction mixture was transferred to this flask over five minutes at RT. The lower aqueous layer was separated and discarded. A solution of 512.5 g of sodium phosphate monobasic, monohydrate in 5125 mL of DI water was prepared and the organic phase was washed with this solution. The lower aqueous phase was again removed and discarded. A solution of 492 g of sodium bicarbonate in 6150 mL of DI water was prepared and the organic phase was washed with this solution which had been split into two portions. Once again the lower aqueous phase was separated and discarded. A saturated sodium chloride solution was prepared in 4100 mL of DI water and the organic phase was washed with this solution, the layers were separated and the lower aqueous phase discarded. The organic layer was concentrated to a foam on a rotary evaporator under vacuum with a 33-44° C. bath temperature to provide a quantitative yield of the title compound as a foam with a chemical purity of 96.3%. The diastereomer ratio was 87:13 (74% de). $^1$H NMR (d6-DMSO, 400 MHz) δ 8.98 (d, b, 1H, J=2.99 Hz), 8.76 (d, 1H, J=8.55 Hz), 8.2 (m, 3H), 8.11 (t, 1H, J=7.71 Hz), 8.02 (d, 1H, J=7.54 Hz), 7.54 (m, 3H), 5.26 (d, 1H, J=4.95 Hz), 4.49 (dd, 1H, J=4.22, 8.52 Hz), 4.13 (m, 2H), 2.6 (m, b, 1H), 2.19 (m, b, 1H), 2.02 (m, b, 1H), 1.83 (t, 1H, J=5.38 Hz), 1.75 (s, b, 1H), 1.68 (m, b, 1H), 1.62 (d, 1H, J=13.9 Hz), 1.36 (d, 1H, J=10.05 Hz), 1.3 (m, b, 3H), 1.22 (d, 6H, J=11.65 Hz), 1.12 (d, 3H, J=6.26 Hz), 0.84 (d, 6H, J=6.57 Hz), 0.79 (s, 3H).

Step D. Preparation of 6-(2S,3R)—N-[(1R)-1-(1,3,6,2-dioxazaborocan-2-yl)-3-methylbutyl}-3-hydroxy-2{(6-phenylpyridin-2-yl)formamido]butanamide (i.e., boronic ester of Formula X). A five liter four neck round bottom flask was equipped with an overhead stirrer, thermocouple and nitrogen outlet before being charged with a solution of 168 g (0.31 mol, 1 eq) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (portion of the product of Step C) in 1680 mL of methanol. To this was added 2000 mL of n-heptane, 78 g (0.78 mol, 2.5 eq) of (2-methylpropyl)boronic acid and a solution of 50 mL (61.2 g, 0.62 mol, 2.0 eq) of 37% hydrochloric acid in 257 mL of DI water. Agitation was begun and the two phase mixture was stirred at RT for 16 hours. The reaction mixture was transferred in portions to a four liter separatory funnel and the lower methanolic phase was separated and returned to the reaction flask. The upper heptane layer was discarded. A fresh charge of 2000 mL of n-heptane was added to the reaction and the reaction was agitated at RT for an additional two hours. Agitation was stopped and the phases were separated and the lower methanolic layer was extracted with n-heptane (1×2000 mL). The heptane phases were discarded and the methanolic phase was concentrated in vacuo with a bath temperature of 40° C. Ethyl acetate (3000 mL) was charged to the evaporation flask and the sticky yellow residue was dissolved before transferring to a twelve-liter reaction flask. The organic phase was washed with an 8% aqueous sodium bicarbonate solution (2×1200 mL) and with brine (1×1000 mL).

After separation of layers the ethyl acetate layer was treated with 34.0 g (0.32 mol, 1.1 eq) of diethanolamine The mixture was allowed to stir at RT overnight. Precipitated solids were collected by vacuum filtration using a closed filtration flask and the wet cake was washed with 400 mL of ethyl acetate. The sealed filter funnel was transferred to a glove box where it was opened and the 568 g of wet cake was transferred to two pyrex drying trays which were then placed into a vacuum oven. The product was dried to a constant weight at 23.5 in of Hg and 55° C. over 27 hours to provide 139.5 g (0.29 mol, 93.5%) of the title compound. The solids were transferred to a three liter four necked round bottom flask equipped with a thermocouple, condenser, heating mantle with temperature controller, overhead stirrer and nitrogen inlet. The solids were recrystallized from 1130 mL of absolute ethanol at 75° C. After cooling to room temperature overnight the product solids were collected in a sealed filter, washed with 125 mL of absolute ethanol before drying under vacuum at 55° C. overnight. After drying 108.5 g (0.225, 72.6%) of product was obtained as a white solid with a 99.8 A % chemical purity by HPLC and a chiral purity of 99.8% de.

Example 3

Preparation of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1).

A 50 mL three neck round bottom flask equipped with a thermocouple, stir bar and nitrogen outlet was charged with 1.65 g (3 4 mmol) of the boronic ester of Formula X (chemical purity=99.5%, chiral purity >99.5% de), 17 mL of methyl isobutyl ketone and 1.7 mL of 2N hydrochloric acid. The mixture was stirred overnight. The layers of the reaction were separated and the organic layer was dried over magnesium sulfate, filtered and evaporated to dryness in vacuo. The residue was triturated in pentane and the resultant white solid was collected by vacuum filtration before drying in a vacuum oven overnight at 60° C. to give 1.26 g (3.1 mmol, 90%) of the title compound. HPLC indicates a purity of 99.6 A %. Chiral purity >99.5% de. $^1$H NMR (d4-MeOD, 400 MHz) δ 8.17 (m, 2H), 8.13 (m, 1H), 8.05 (m, 2H), 7.5 (m, 3H), 4.75 (d, 1H, J=3.04 Hz), 4.42 (dq, 1H, J=2.92, 6.4), 2.7 (t, b, 1H), 1.61 (m, 1H), 1.35 (t, 2H, J=7.48 Hz), 1.29 (d, 3H, J=6.36 Hz), 0.89 (d, 6H, J=6.52 Hz).

Example 4

Alternative Preparation of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1)

A 250 mL three neck round bottom flask equipped with a thermocouple, stir bar and nitrogen outlet was charged with 12 g (24.9 mmol) of the boronic ester of Formula X (chemical purity=99.6%, chiral purity >99.5% de), 120 mL of methanol and 25 mL of 2N hydrochloric acid. The solids dissolved almost immediately and the reaction was allowed to stir overnight for convenience. The solvents were removed in vacuo and the residue was dissolved in 120 mL of ethyl acetate. The organic phase was washed with 8% aqueous sodium bicarbonate (1×100 mL) and then evaporated to dryness in vacuo. The resultant residue was triturated overnight with 120 mL of pentane to give a white amorphous solid which was collected by vacuum filtration, washed with 50 mL of pentane and dried in a vacuum oven at 35° C. overnight with a nitrogen sweep. This yielded 7.9 g (19.1 mmol, 76.8%) of the title compound with a chemical purity of 99.5 A % and an optical purity of 99.8% de.

Example 5

Purification of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1)

Compound 1 (10 g, 24.2 mmol) that had been severely degraded by heating in a vacuum oven at 90° C. overnight and having a chemical purity of only 56 A % was charged to 250 mL three necked round bottom flask equipped with a stir bar and nitrogen outlet. Ethyl acetate (100 mL) was then charged and the mixture stirred at room temperature until all solids had dissolved. Diethanolamine (2.71 g, 25.5 mmol, 1.05 eq) was added and almost immediately solids began to precipitate. The reaction was stirred at room temperature overnight before the light yellow solids were collected by vacuum filtration and washed with 60 mL of ethyl acetate. The chemical purity had been upgraded to 90.7 A %. The crude wet solids were recrystallized from 80 mL of absolute ethanol to give material with a chemical purity of 98.8 A %. A second absolute ethanol recrystallization yielded, after vacuum drying at 55° C. overnight, 4.6 g (9.54 mmol, 70% corrected for SM purity) of ester as a white solid with a chemical purity of 99.2 A %. No optical isomer was detected in the HPLC so chiral purity was >99.8% de.

Example 6

Preparation of (2S)—N-[(1R)-1-(1,3,6,2-dioxazaborocan-2-yl)-3-methylbutyl]-3-phenyl-2-(pyrazin-2-ylformamido)propanamide (i.e., boronic ester of Formula XI)

Step A. Preparation of Pyrazine-2-carbonyl chloride

A 500 ml three neck round bottomed flask equipped with a stir bar, thermocouple, heating mantle with digital temperature controller, condenser and nitrogen inlet/outlet was charged with 15 g (0.12 mol) of pyrazine carboxylic acid, 225 mL of toluene (Kf<0.02 wt %) and 26.4 ml (43 g, 0.36 mol) of thionyl chloride. The thin slurry was heated to 75° C. and stirred overnight (10-16 hr). After cooling the reaction mixture to room temperature the solvent and excess thionyl chloride were removed in vacuo as follows: Reaction mixture was stripped under full vacuum at 60° C. (bath temperature) to approximately ⅓ its original volume and then (175 ml) of fresh toluene was added. Concentration was continued, again stripping to ⅓ original volume followed by re-dilution with 225 ml of fresh toluene to provide the pyrazine acid chloride in a toluene solution.

Step B. Preparation of (S)-3-Phenyl-2-[(pyrazine-2-carbonyl)-amino]-propionic acid (i.e., acid of Formula II, wherein $R^1$ is 2-pyrazinyl and $R^2$ is benzyl). A second 500 ml three neck round bottomed flask was equipped with a stir bar, thermocouple, pressure equalizing dropping funnel, nitrogen inlet/outlet and ice/water cooling bath. L-Phenylalanine, 20.2 g (0.122 mol) was added, followed by 28.2 g (0.266 mol) of sodium carbonate and 225 mL of deionized water. The aqueous solution was cooled to 10.0° C. During this time the addition funnel was charged with the acid chloride/toluene solution prepared in Step A (~125 mL). This toluene solution was added dropwise to the aqueous reaction over approximately 10 minutes at ~10° C. Once the addition was complete, the reaction was warmed to room temperature (~22-25° C.) and vigorously stirred for 3 h. The reaction mixture was then transferred to a separatory funnel and the two layers were separated. The lower aqueous phase was then recharged to the reaction flask. Methanol (125 mL) was then added to the red solution followed by pH adjustment (target pH=1-2) with 3.0 M HCl (~175 mL), keeping the temperature at 15-20° C. Some off-gassing occurred at ~pH=5, followed by precipitation of the product at pH=3. The slurry was allowed to stir at room temperature for 30 minutes at ambient temperature post pH adjustment. The resulting pink solid precipitate was collected by vacuum filtration, (mother liquor losses <2 mg/mL), washed with deionized water (1×50 ml) then dried in a vacuum oven at 40° C. with a nitrogen sweep to a constant weight to provide 11.92 g (0.43.9 mmol, 36%) of the title compound with an HPLC purity of 99 A %. $^1$H NMR (d6-DMSO, 400 MHz) δ 13.04 (s, 1H), 9.14 (d, 1H, J=1.44 Hz), 8.88 (dd, 2H, J=2.48, 6.16 Hz), 8.75 (dd, 1H, J=1.52, 2.4 Hz), 7.25 (m, 4H), 7.18 (m, 1H), 4.75 (dt, 1H, J=5.48, 8.08 Hz), 3.2 (dd, 2H, J=1.79, 5.32 Hz).

Step C. Preparation of N-[(1S)-1[[[(1R)-1-[3aS,4S,6S,7aR)-hexahydro-3a,5,5-trimethyl-4,6-methano-1,3,2-benzodioxaborol-2-yl]-3-methylbutyl]amino]carbonyl]-2-benzyl] 2-pyrazine carboxamide (i.e., (1S,2S,3R,5S)-(+)-2,3-pinanediol boronic ester of Formula IV, wherein $R^1$ is 2-pyrazinyl and $R^2$ is benzyl). A 500 ml three neck round bottomed flask equipped with a stir bar, addition funnel, thermocouple, nitrogen inlet/outlet and cooling bath was charged with 11 g (99.9 mmol) of (S)-3-Phenyl-2-[(pyrazine-2-carbonyl)-amino]-propionic acid, 15.5.0 g (40.6 mmol) of O-(7-azabenzotriazol-1-yl)-N,N,N'N'-tetramethyluronium hexafluorophosphate (HATU), 12.2 g (40.6 mmol) of (1R)-1-[(3aS,4S,6S,7aR)-hexahydro-3a,5,5-trimethyl-4,6-methano-1,3,2-benzodioxaborol-2-yl]-3-methylbutylamine hydrochloride salt (87:13 mixture of isobutyl diastereomers (R:S)) and 165 mL of N,N-dimethylformamide (DMF). The pale yellow reaction solution was cooled to −35° C. where 12.6 g (17 mL, 97.3 mmol) of N,N-di-isopropyl ethyl amine was added dropwise over six minutes at −34° C. to −35° C. The resulting solution was then stirred overnight at −40 to −11° C. The reaction mixture was quenched onto 600 ml of a 1:1 cold water/ethyl acetate mixture. After transferring into a separatory funnel the layers were separated. The organic phase was then washed successively with 10% aqueous sodium hydrogen phosphate (1×200 mL), 8% aqueous sodium bicarbonate (2×200 mL) and saturated sodium chloride (1×200 mL). The product solution was dried over magnesium sulfate then filtered. The filtrate was evaporated to dryness in vacuo to give 19.57 g (37 7 mmol, 93%) of the title compound as a light brown foam with an HPLC purity of 92 A %. $^1$H NMR (d6-DMSO, 400 MHz) δ 9.15 (d, 1H, J=1.44 Hz), 8.87 (d, 1H, J=2.48 Hz), 8.7 (m, 3H), 7.25 (m, 4H), 7.18 (m, 1H), 4.89 (q, 1H, J=6.88, 15.4 Hz), 4.13 (dd, 1H, J=1.8, 8.56 Hz), 3.15 (d, 2H, J=6.88 Hz), 2.7 (m, b, 1H), 2.22 (m, b, 1H), 2.05 (m, b, 1H), 1.87 (t, 1H, J=5.40 Hz), 1.81 (s, b, 1H), 1.67 (d, b, 1H), 1.52 (m, b, 1H), 1.13-1.33 (m, 9H), 0.83 (dd, 6H, J=2.48, 6.56 Hz), 0.80 (s, 3H).

Step D. Preparation of (2S)—N-[(1R)-1-(1,3,6,2-dioxazaborocan-2-yl)-3-methylbutyl]-3-phenyl-2-(pyrazin-2-ylformamido)propanamide (i.e., boronic ester of Formula XI). A one liter four neck round bottomed flask was equipped with an overhead stirrer, thermocouple and nitrogen inlet/outlet then charged with 19.0 g (36.6 mmol) of N-[(1S)-1[[[(1R)-1-[(3aS,4S,6S,7aR)-hexahydro-3a,5,5-trimethyl-4,6-methano-1,3,2-benzodioxaborol-2-yl]-3-methylbutyl] amino]carbonyl]-2-benzyl]2-pyrazine carboxamide, 9.32 g (91.5 mmol) of isobutylboronic acid, 190 mL of methanol, 34.7 mL (69.4 mmol) of 2M aqueous hydrochloric acid and 285 mL of heptane. The two phase reaction was stirred at room temperature overnight until an IPC showed <2% starting material remaining by area. The reaction mixture was transferred to a separatory funnel and the layers were separated. The lower methanol layer was washed with heptanes (2×250 mL) before being removed to a one-liter round bottomed flask and evaporating to dryness in vacuo. The resulting residue was dissolved in 300 mL of ethyl acetate which was washed with 8% aqueous sodium bicarbonate (2×200 mL) and brine (1×300 mL), before transferring to a clean one liter three neck round bottom flask equipped as above.

To the ethyl acetate solution was added 4.1 g (38.4 mmol) of diethanolamine and the mixture was stirred at room temperature over the weekend. The resulting solids were collected by vacuum filtration, washed with ethyl acetate (1×30 mL) then dried in a vacuum oven at 50° C. overnight to provide the title compound as a white solid (15.8 g, 34.9 mmol, 95.2%), which was shown by HPLC to be a 91:9 mixture of diastereomers (i.e., 82% de).

Step E (optional). Purification of (2S)—N-[(1R)-1-(1,3,6,2-dioxazaborocan-2-yl)-3-methylbutyl]-3-phenyl-2-(pyrazin-2-ylformamido)propanamide (i.e., boronic ester of Formula XI). (2S)—N-[(1R)-1-(1,3,6,2-dioxazaborocan-2-yl)-3-methylbutyl]-3-phenyl-2-(pyrazin-2-ylformamido) propanamide was charged to a 250 ml three roundbottom flask equipped with a stir bar, thermocouple, heating mantle, controller, condenser and nitrogen inlet/outlet. Ethanol (absolute, 128 mL) was then charged to the flask and heated to reflux. Not all the solids dissolved and these were removed by vacuum filtration and later shown to be enriched (2:8) in the undesired isomer. The filtrate was returned to the round bottom flask and cooled to room temperature to crystallize the product which was isolated by vacuum filtration, washed with cold absolute ethanol (1×50 ml), and dried in a vacuum oven at 50° C. overnight to provide 11.6 g (25.6 mmol, 70%) of the title compound as a 94:6 mixture of diastereomers (i.e., 88% de). The chemical purity was >99.9 A %. 1H NMR (d6-DMSO, 400 MHz) δ 9.10 (d, 1H, J=1.4 Hz), 8.88 (d, 1H, J=2.48 Hz), 8.83 (d, 1H, J=8.84 Hz), 8.75 (dd, 1H, J=1.52, 2.32 Hz), 7.3 (m, 5H), 6.55 (s, b, 1H), 4.75 (m, 1H), 3.65 (m, 2H), 3.55 (m, 1H), 3.45 (m, 1H), 2.9-3.2 (m, 4H), 2.8 (m, 1H), 2.7 (m, 2H), 1.56 (m, 1H), 1.33 (dt, 1H, J=4.04, 13.80 Hz), 1.18 (dt, 1H, J=3.48, 9.88 Hz), 0.8 (dd, 6H, J=6.64, 12.56 Hz).

Example 7

Preparation of bortezomib

A 100 ml three neck round bottom flask was equipped with a stir bar, thermocouple and nitrogen inlet/outlet then charged with 5.0 g (10.4 mmol) of (2S)—N-[(1R)-1-(1,3,6,2-dioxazaborocan-2-yl)-3-methylbutyl]-3-phenyl-2-(pyrazin-2-ylformamido)propan-amide (i.e., boronic ester of Formula XI), 50 ml of methanol and 10.4 ml of 2N aqueous hydrochloric acid. The reaction was stirred at room temperature overnight before removing the solvent in vacuo at 40° C. The resulting residue was dissolved in 50 ml of ethyl acetate and washed with saturated sodium bicarbonate (1×50 mL) before once again concentrating the organic to dryness in vacuo. The residue was then triturated overnight at room temperature with 50 mL of pentane under nitrogen. The resulting free flowing solids were collected by vacuum filtration, washed with pentane (1×20 ml) then dried in a vacuum oven at 30° C. overnight to provide 3.29 g (8.56 mmol, 82.3%) of the title compound as a white solid. HPLC analysis indicated chemical purity >99.8 A % and a 93.5:6.5 ratio of diastereomers (i.e., 87% de).

1H NMR (d4-MeOH, 400 MHz) δ 9.15 (d, 1H, J=1.36 Hz), 8.77 (d, 1H, J=2.48 Hz), 8.68 (dd, 1H, J=1.52, 2.44 Hz), 7.27 (m, 4H), 7.21 (m, 1H), 5.05 (t, 1H, J=7.68 Hz), 3.2 (m, 2H), 2.66 (t, 1H, J=7.56 Hz), 1.39 (m, 1H), 1.17 (t, 2H, J=7.12 Hz), 0.83 (dd, 6H, J=5.32, 6.40 Hz).

Example 8

Preparation of 6-Phenyl-pyridine-2-carboxylic acid {(1S,2R)-1-[(R)-1-(4,8-dimethyl-[1,3,6,2-dioxaborocan-2-yl)-3-methylbutylcarbamoyl]-2-2-hydroxypropyl]amide (i.e., boronic ester of Formula IX)

A 50 mL four neck round bottom flask was equipped with a stir bar, thermocouple, heating mantle with temperature controller, condenser and nitrogen inlet then charged with 2.0 g (3.65 mmol) of N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide (chemical purity=95.7%, chiral purity about 97.5% de (based on the fact that the (1R)-1-[(3aS,4S,6S,7aR)-hexahydro-3a,5,5-trimethyl-4,6-methano-1,3,2-benzodioxaborol-2-yl]-3-methylbutylamine used to make the N-[(1S,2R)-1[[[(1R)-1-1[(3aS,4S,6S,7aR)-hexahydro-3a,5,5-trimethyl-4,6-methano-1,3,2-benzodioxaborol-2-yl]-3-methylbutyl]amino]carbonyl]2-hydroxypropyl]-6-phenyl-2-pyridinecarboxamide had a 97.5% de)), 30 mL of t-butyl methyl ether (MTBE) and 0.61 g (94.56 mmol, 1.25 eq) of diisopropanolamine The resultant yellow solution was stirred at 20-25° C. for 16 hours at which point only a small amount of solid had formed. An additional 1.2 g (9 mmol, 2.5 eq) of diisopropanolamine was charged and the mixture was heated at 40° C. for 16 hours before cooling to room temperature. The white solid was collected by vacuum filtration, washed with 15 mL of MTBE then dried under vacuum overnight at 33° C. to yield 1.31 g (2.55 mmol, 70%) of the desired product based on 1H NMR. The chemical purity was 96.8 A % and no diastereomer was detected by HPLC (>99.8% de).

Example 9

Storage Stability of 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X)

Storage Conditions.

Bulk solid state drug substance was put in polyethylene (PE) double bag in high-density polyethylene (HDPE) containers and the containers were stored under three conditions: (a) 4° C., (b) 25° C./60% relative humidity (RH), and (c) 40° C./75% RH.

Stability Testing.

6-(2S,3R)—N-[(1R)-1-(1,3,6,2-dioxazaborocan-2-yl)-3-methylbutyl}-3-hydroxy-2-{(6-phenylpyridin-2-yl)formamido]butanamide converts to [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1) as soon as it is in the presence of an aqueous phase. Therefore, HPLC analysis of purity was of the [(1R)-1-[[(2S,3R)-3-Hydroxy-2-[[(6-phenylpyridin-2-yl)carbonyl]amino]-1-oxobutyl]amino]-3-methylbutyl]boronic acid hydrolysis product. Stability was tested at time zero (T0), and after storage for one month (1M), six months (6M) and (except for the 40° C./75% RH conditions) one year (12M).

Stability Results.
Appearance

| Conditions | 4° C. | 25° C./60% RH | 40° C./75% RH |
| --- | --- | --- | --- |
| T0 | White to off-white powder | White to off-white powder | White to off-white powder |
| 1 M | White to off-white powder | White to off-white powder | White to off-white powder |
| 6 M | White to off-white powder | White to off-white powder | White to off-white powder |
| 12 M | White to off-white powder | White to off-white powder | NA |

|  | Conditions | | |
| --- | --- | --- | --- |
|  | 4° C./ambient RH | 25° C./60% RH | 40° C./75% RH |
|  | Time | | |
|  | T0 | 1 M | 6 M | 12 M | 1 M | 6 M | 12 M | 1 M | 6 M |
| Chemical purity (%) | 99.5 | 99.8 | 99.9 | 99.9 | 99.6 | 99.8 | 99.9 | 99.7 | 99.8 |
| Impurity by HPLC (%) | | | | | | | | | |
| RRT = 0.49 | | ND | 0.06 | ND | ND | 0.09 | 0.08 | 0.07 | 0.10 | 0.10 |
| RRT = 1.18 | | 0.50 | 0.17 | ND | 0.07 | 0.32 | 0.06 | 0.08 | 0.18 | 0.11 |

Example 9A

Comparative Storage Stability of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1)

Three (3) separate batches of Compound 1 were tested for storage stability. The batches are identified as Batch A, Batch B, and Batch C below.

Storage Conditions.

Bulk solid state drug substance was put in polyethylene (PE) double bag in high-density polyethylene (HDPE) containers and the containers were stored under the indicated conditions.

Stability Results.
Batch A

Appearance

| Conditions | 4° C./ambient RH | 25° C./60% RH | 40° C./75% RH |
| --- | --- | --- | --- |
| T0 | White to off-white powder | White to off-white powder | White to off-white powder |
| 3 Months (3 M) | White to off-white powder | White to off-white powder | White to off-white powder |
| 6 Months (6 M) | White to off-white powder | White to off-white powder | White to off-white powder |

Purity

|  | Conditions | | |
| --- | --- | --- | --- |
|  | 4° C./ambient RH | 25° C./60% RH | 40° C./75% RH |
|  | Time | | |
|  | T0 | 3 M | 6 M | 3 M | 6 M | 3 M | 6 M |
| HPLC Purity (%) | 95.3* | 94.5 | 94.1 | 94.4 | 94.1 | 93.2 | 88.7 |

*estimated

Batch B—Stored at 5° C./Ambient RH

|  | Time | | | |
| --- | --- | --- | --- | --- |
| Test | T0 | 1 Month | 3 Month | 6 Month |
| Appearance | White powder | White powder | White powder | White powder |
| Assay by HPLC (anhydrous) (%) | 101.7 | 97.1 | 94.0 | 93.5 |
| Assay by HPLC (as-is) (%) | 94.4 | 90.6 | 87.5 | 85.1 |
| Total Impurities (%) | 0.6 | 3.0 | 5.9 | 7.3 |
| Water Content (%) | 6.5 | 6.0 | 6.1 | 8.2 |

Batch C—Stored at 5° C./Ambient RH

| Test | Time | | | | |
|---|---|---|---|---|---|
| | T0 | 1 Month | 3 Month | 6 Month | 12 Month |
| Appearance | Yellowish solid | White to yellow powder or solid | White to yellow powder or solid | Off-white powder | Off-white powder |
| Assay by HPLC (anhydrous) (%) | 98.1 | 97.0 | 102.4 | 99.9 | 95.9 |
| Assay by HPLC (as-is) (%) | 92.9 | 91.4 | 94.6 | 91.0 | 87.0 |
| HPLC Purity (%) | 98.2 | 97.2 | 96.2 | 96.3 | 96.2 |
| Water Content (%) | 4.16 | 4.59 | 6.48 | 7.74 | 8.16 |

Example 10

Comparative bioavailability of bortezomib and (2S)—N-[(1R)-1-(1,3,6,2-dioxazaborocan-2-yl)-3-methylbutyl]-3-phenyl-2-(pyrazin-2-ylformamido) propanamide (i.e., boronic ester of Formula XI)

General Methods.

Three adult male Sprague Dawley rats were used in each treatment group. The rats were fasted overnight prior to oral dose administration. Intravenous administration was via the lateral tail vein and oral doses were administered by gavage. The compound was administered iv in a vehicle of 3% DMSO:30% Solutol:67% phosphate buffered saline. Oral dosing was in phosphate buffered saline.

For blood collection, each rat (unanesthetized) was placed in a clear Plexiglas® restraining tube, and blood samples (approximately 0.25 mL) were drawn from a lateral tail vein into heparinized collection tubes at predetermined sampling times (0.083, 0.25, 0.5, 1, 2, 4, and 6 hours post dose). No pre-dose samples were obtained. The exception to this procedure was the last sampling time in which the animals were sacrificed by decapitation and trunk blood was obtained rather than blood via a tail vein. The blood samples were placed on wet ice until centrifuged to separate plasma. The plasma fraction was transferred into clean dry tubes, frozen on dry ice and stored at approximately −20° C. pending analysis.

Plasma was prepared for high performance liquid chromatography (HPLC)/mass spectrometric analysis according to standard protocol following protein precipitation with acetonitrile containing an internal standard. The plasma samples were then analyzed for both bortezomib and alprenolol (internal standard) via HPLC coupled with tandem mass spectrometry.

The plasma concentration data for all rats were entered into Excel spreadsheets in preparation for pharmacokinetic analysis. Pharmacokinetic parameters for bortezomib were estimated for each rat by non-compartmental analysis (Gibaldi M, Perrier D. Pharmacokinetics, $2^{nd}$ edition, Marcel Dekker, New York, Chapter 11, 1982) of the plasma concentration versus time data using WinNonlin software (Professional Version 4.1, Pharsight Corporation, Palo Alto, Calif., 1997).

The maximum plasma concentration (Cmax) was the highest observed plasma concentration after an oral dose; tmax was the corresponding time when Cmax was observed. The terminal rate constant for elimination from plasma ($\beta$) was estimated by linear regression of the terminal portion of the semi-logarithmic plasma concentration versus time curve. The apparent terminal half-life ($t_{1/2}$) was calculated as 0.693 divided by $\beta$. The area under the plasma concentration versus time curve from time zero to the time of the last measurable concentration ($AUC_{0-t}$) after a single dose was determined by the linear trapezoidal rule. The area from zero to infinity ($AUC_{0-\infty}$) was calculated as the sum of $AUC_{0-t}$ and the area extrapolated from the last measurable concentration to infinity ($C_{last}/\beta$). Concentrations pre dose were all assumed to be zero for the purpose of calculation of the AUC. Oral bioavailability was determined by dividing the dose normalized oral $AUC_{0-\infty}$ by the $AUC_{0-\infty}$ from iv dosing and multiplying by 100 to express the ratio as a percent.

Results.

The mean±SEM. pharmacokinetic parameters for bortezomib in male Sprague Dawley rats administered as single iv and oral doses of bortezomib itself ("Velcade") or its diethanolamine ester ("DEA Adduct"; i.e., boronic ester of Formula XI) are shown below.

| 0.8 mg/kg, i.v. | | 4 mg/kg, p.o. | Velcade | DEA Adduct |
|---|---|---|---|---|
| $t_{1/2}$, h | 0.8 ± 0.1 | $C_{max}$, ng/mL | 157 ± 55 | 404 ± 59 |
| $AUC_{0-t}$, ng * h/mL | 459 ± 127 | $t_{max}$, h | 0.25 ± 0 | 0.25 ± 0 |
| $AUC_{0-\infty}$, ng * h/mL | 472 ± 127 | $AUC_{0-t}$, ng * h/mL | 176 ± 41 | 382 ± 47 |
| Vd, L/kg | 2.4 ± 0.8 | $AUC_{0-\infty}$, ng * h/mL | 210 ± 44 | 431 ± 58 |
| CL, mL/min/kg | 34 ± 11 | $t_{1/2}$, h | 2.3 ± 0.3 | 1.9 ± 0.1 |
| Mean ± SEM, n = 3 | | Oral Bioavailability, % | 9 ± 2 | 18 ± 2 |

Figure 2:
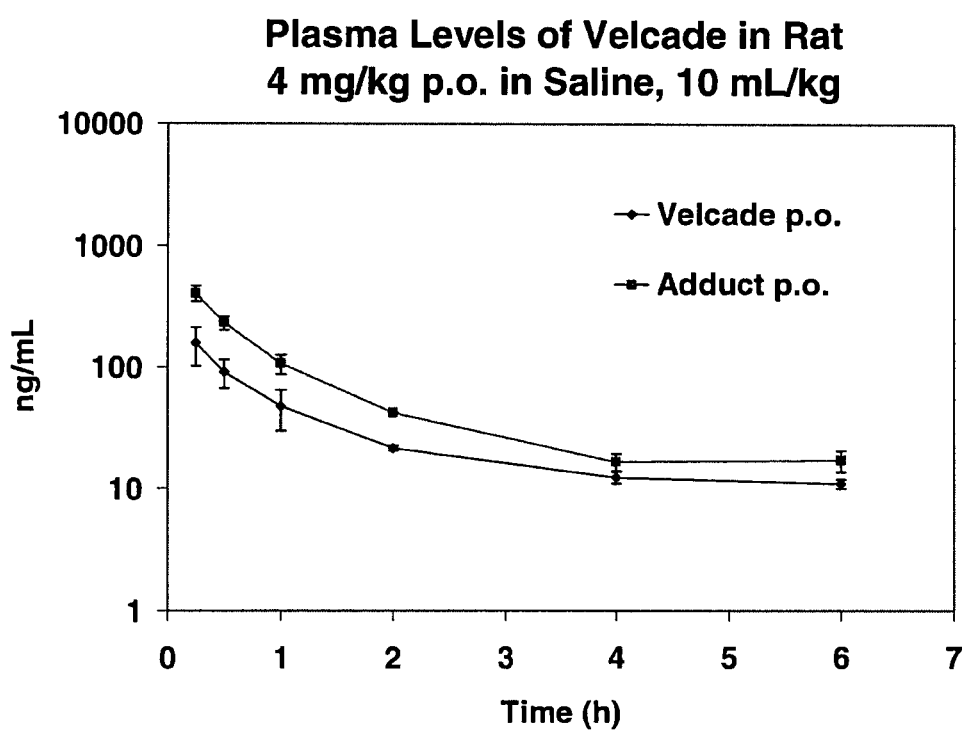
FIG. 2 depicts plasma levels of Velcade® in rat at 4 mg/kg p.o in saline, 10 mL/kg (after oral administration only).

The corresponding mean±SEM. plasma concentration versus time profiles are shown in FIGS. 1 and 2.

After bolus iv administration of bortezomib at 0.8 mg/kg, the mean half-life was 0.8±0.1 h. The mean plasma clearance rate (CL) was 34±11 mL/min/kg and the mean volume of distribution ($V_d$) was 2.4±0.8 L/kg.

After administration of a single 4 mg/kg oral dose of bortezomib, the mean $C_{max}$ was 157±55 ng/mL at a $t_{max}$ of 0.25 h. The area under the curve ($AUC_{0-t}$) through 6 hours post dose was 176±41 ng*h/mL. $AUC_{0-\infty}$ was estimated to be 210±44 ng*h/mL. This AUC value was used with the AUC at 1 mg/kg iv to calculate an estimated oral bioavailability of 9±2%.

After administration of a single 4 mg-eq/kg oral dose of the boronic ester of Formula XI, the mean $C_{max}$ was 404±59 ng/mL at a $t_{max}$ of 0.25 h. The area under the curve ($AUC_{0-t}$) through 6 hours post dose was 382±47 ng*h/mL. $AUC_{0-\infty}$ was estimated to be 431±58 ng*h/mL. This AUC value was used to with the AUC at 1 mg/kg iv to calculate an estimated oral bioavailability of 18±2%.

Based on these results it can be concluded that bortezomib is poorly bioavailable (<10%) in the male Sprague Dawley rat. However, the oral bioavailability of the parent compound can be increased approximately two fold (18%) by administration of an equivalent oral dose of the DEA adduct.

Example 11

Comparative Bioavailability of Bortezomib and (2S)—N-[(1R)-1-(1,3,6,2-dioxazaborocan-2-yl)-3-methylbutyl]-3-phenyl-2-(pyrazin-2-ylformamido) propanamide (i.e., boronic ester of Formula XI)

General Methods.

The experiment was performed as in Example 10.

Results.

After administration of a single 4 mg/kg oral dose of bortezomib, the mean $C_{max}$ was 208±15 ng/mL at a $t_{max}$ of 0.25 h. The area under the curve ($AUC_{0-t}$) through 6 hours post dose was 209±8 ng*h/mL. AUC0-∞ was estimated to be 243±6 ng*h/mL.

After administration of a single 4 mg-eq/kg oral dose of the boronic ester of Formula XI, the mean $C_{max}$ was 302±105 ng/mL at a $t_{max}$ of 0.25 h. The area under the curve ($AUC_{0-t}$) through 6 hours post dose was 427±121 ng*h/mL. AUC0-∞ was estimated to be 457±123 ng*h/mL.

Relative to the administration of the parent compound, the plasma level exposure of bortezomib was increased when the DEA adduct (compound of Formula XI) was administered orally. The oral exposure was increased by ~1.5 as determined by the $C_{max}$ and ~2 fold as determined by the AUC. This result is consistent with the results of Example 10.

| 4 mg/kg, p.o. | Velcade | DEA Adduct |
|---|---|---|
| $C_{max}$ (ng/mL) | 208 ± 15 | 302 ± 105 |
| $T_{max}$ (h) | 0.25 ± 0 | 0.25 ± 0 |
| $AUC_{0-t}$ (ng * h/mL) | 209 ± 8 | 427 ± 121 |
| $AUC_{0-\infty}$ (ng * h/mL) | 243 ± 6 | 457 ± 123 |
| $T_{1/2}$ (h) | 2.3 ± 0.5 | 1.3 ± 0.1 |

Figure 3:
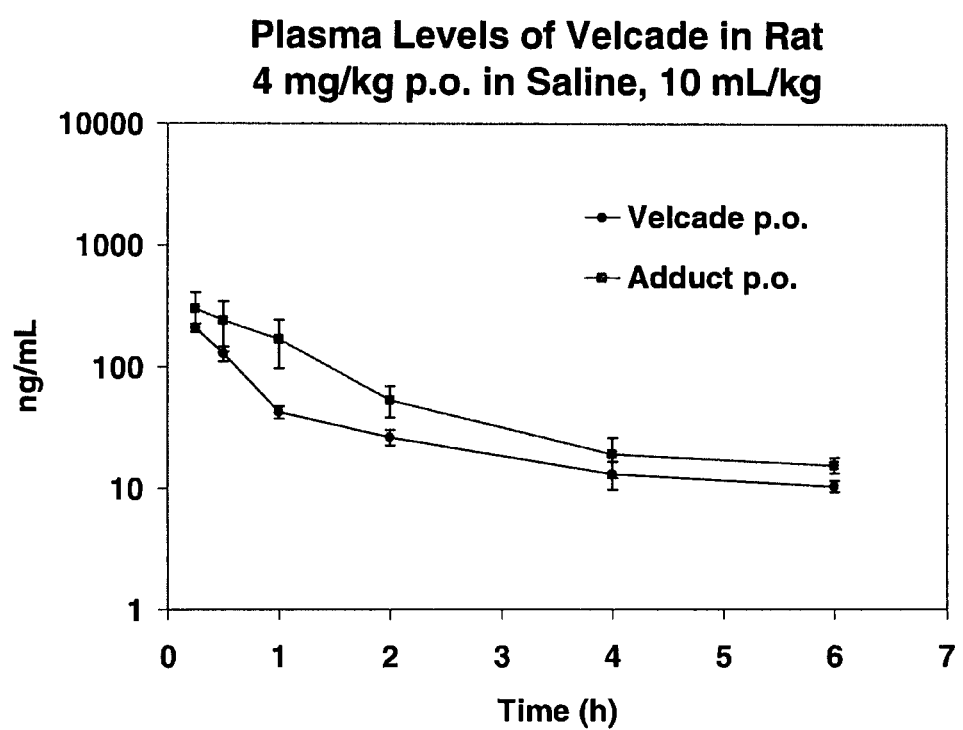
FIG. 3 depicts plasma levels of Velcade® in rat at 4 mg/kg p.o in saline, 10 mL/kg.
Figure 4:
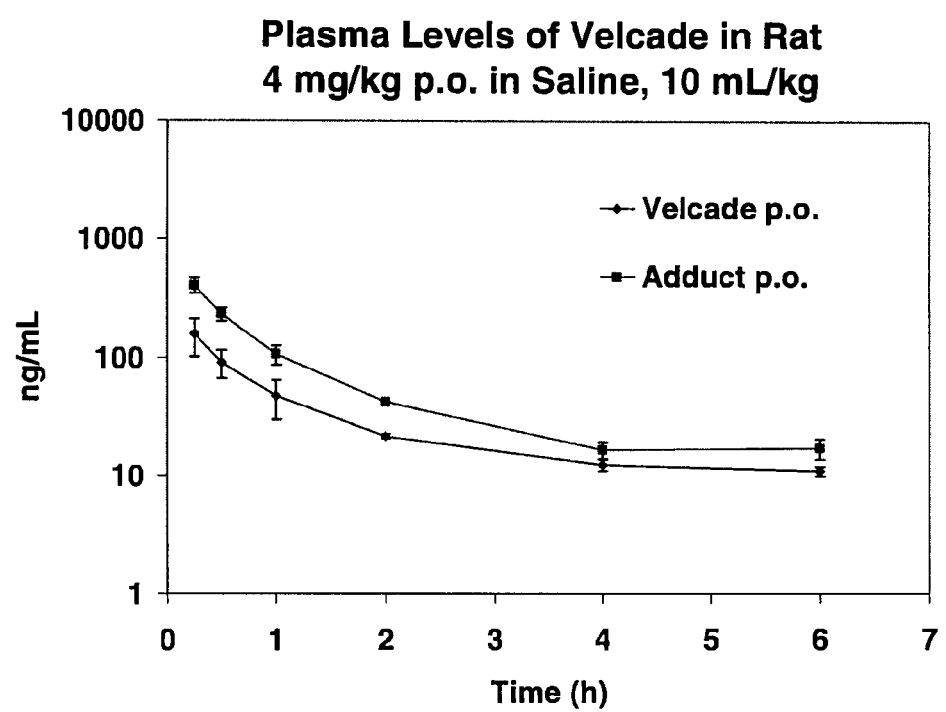
FIG. 4 depicts plasma levels of Velcade® in rat at 4 mg/kg p.o in saline, 10 mL/kg (from Example 10).

The corresponding mean±SEM plasma concentration versus time profiles are shown in FIGS. 3 and 4.

Example 12

Comparative Bioavailability of Bortezomib and (2S)—N-[(1R)-1-(1,3,6,2-dioxazaborocan-2-yl)-3-methylbutyl]-3-phenyl-2-(pyrazin-2-ylformamido) propanamide (i.e., boronic ester of Formula XI)

General Methods.

The experiment was performed as in Examples 10 and 11, except that both the bortezomib and its DEA adduct (compound of Formula XI) were administered orally using a vehicle that contained 0.6% DMSO and 2% Solutol HS-15 (polyethylene glycol 660 hydroxystearate) in PBS. Solutol has been reported to be an inhibitor of the Pgp transporter in vitro.

Results.

| 4 mg/kg, p.o. | Velcade | DEA Adduct |
|---|---|---|
| $C_{max}$ (ng/mL) | 463 ± 190 | 522 ± 217 |
| $T_{max}$ (h) | 0.25 ± 0 | 0.25 ± 0 |
| $AUC_{0-t}$ (ng * h/mL) | 372 ± 119 | 426 ± 154 |
| $AUC_{0-\infty}$ (ng * h/mL) | 403 ± 125 | 459 ± 165 |
| $T_{1/2}$ (h) | 2.0 ± 0.4 | 2.2 ± 0.3 |

The Solutol formulation appeared to affect the pharmacokinetics of bortezomib more than its DEA adduct, resulting in similar bioavailability for the two compounds when administered in this formulation. However, this study is not considered reliable because Solutol appears to negatively affect similar formulations of the related compound 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X). Specifically, although pharmacokinetic experiments performed with saline formulations of the boronic ester of Formula X were valid and reproducible, corresponding experiments using Solutol formulations were highly variable and irreproducible.

Example 13

Lyophilized Formulation of [(1R)-1-[[(2S,3R)-3-Hydroxy-2-[[(6-phenylpyridin-2-yl)carbonyl]amino]-1-oxobutyl]amino]-3-methylbutyl]boronic acid (i.e., Compound 1) Prepared From 6-(2S,3R)—N-[(1R)-1-(1,3,6,2-dioxazaborocan-2-yl)-3-methylbutyl}-3-hydroxy-2-{(6-phenylpyridin-2-yl)formamido]butanamide (i.e., boronic ester of Formula X)

Mannitol (39.2 mg) and Kleptose® HP (hydroxypropyl-β-cyclodextrin; 49 mg) are dissolved in sterile water for injection (598.633 mg) at room temperature. Boronic ester of Formula X (1.167 mg) is dispersed in tert-butanol (312 mg) by magnetic stirring protected from light at room temperature during 10 minutes. A few mL of the Mannitol/Kleptose® solution is poured into the boronic ester of Formula X dispersion in order to solubilize the boronic ester of Formula X. After forming a solution, the remaining Mannitol/Kleptose® solution is added. The solution is stirred for a few minutes while protected from light. The pH is adjusted with phosphoric acid down to pH 4.0±0.2. The solution is filtered through a sterile disposable PVDF filter of 0.22 nm (Stericup Millipore®) to form a clear solution. 4 mL of the solution is transferred into a 10 mL bottle and then freeze-dried. The freeze-dried formulation contains >3.99 mg Compound 1 and <0.01 mg boronic ester of Formula X.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

All publications referenced herein are incorporated by reference in their entireties for all purposes.

What is claimed:

1. A boronic ester of Formula I

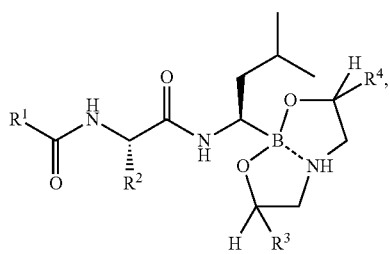

I wherein
- $R^1$ is 2-(6-phenyl)pyridinyl, $R^2$ is (1R)-1-hydroxyethyl, and $R^3$ and $R^4$ are H;
- $R^1$ is 2-(6-phenyl)pyridinyl, $R^2$ is (1R)-1-hydroxyethyl, and $R^3$ and $R^4$ are methyl; or
- $R^1$ is 2-pyrazinyl, $R^2$ is benzyl, and $R^3$ and $R^4$ are H.

2. The boronic ester of claim 1, wherein the boronic ester is Formula IX

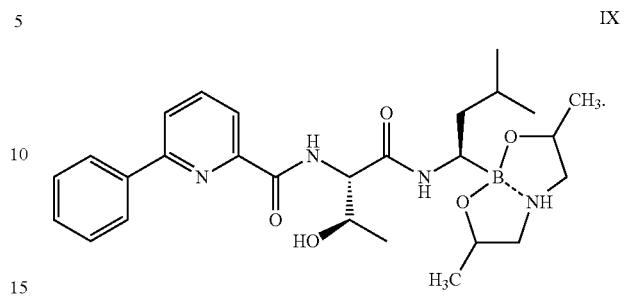

IX

3. The boronic ester of claim 1, wherein the boronic ester is Formula X

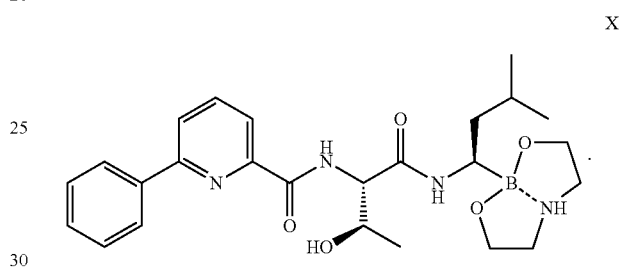

X

4. The boronic ester of claim 1, wherein the boronic ester is Formula XI

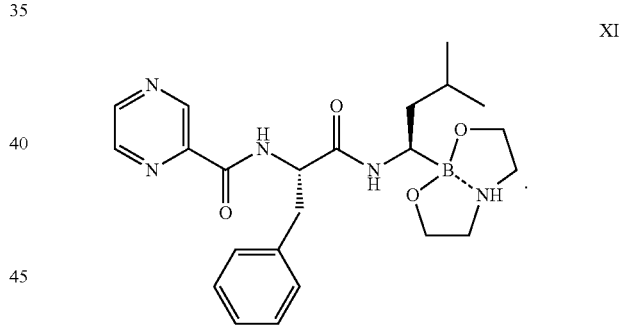

XI

5. A process for preparing a pharmaceutical composition, comprising the step of combining the boronic ester of any of claims 1-4 with a pharmaceutically acceptable carrier, diluent, or excipient.

6. A process for preparing a pharmaceutical composition of a boronic acid of Formula IA

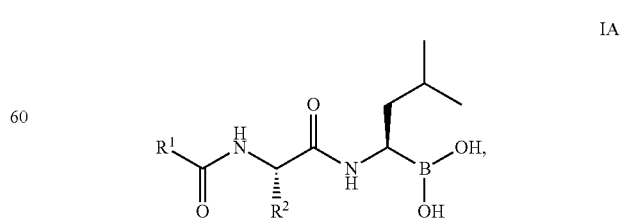

IA wherein $R^1$ is 2-(6-phenyl)pyridinyl and $R^2$ is (1R)-1-hydroxyethyl, or $R^1$ is 2-pyrazinyl and $R^2$ is benzyl;

comprising the steps of:
(a) converting a boronic ester of any of claims 1-4 into a boronic acid of Formula IA; and
(b) combining the boronic acid of Formula IA with a pharmaceutically acceptable carrier, diluent, or excipient.

7. The process of claim 6, wherein $R^1$ is 2-(6-phenyl)pyridinyl and $R^2$ is (1R)-1-hydroxyethyl.

8. The process of claim 6, wherein $R^1$ is 2-pyrazinyl and $R^2$ is benzyl.

9. A process for purifying a boronic acid of Formula IA

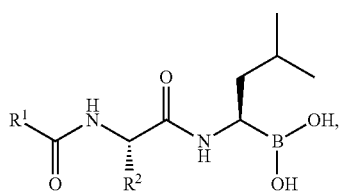

IA wherein
$R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) converting the boronic acid of Formula IA into a boronic ester of Formula VII

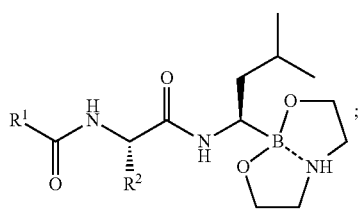

VII (b) crystallizing the boronic ester of Formula VII from solution;
(c) isolating the crystallized boronic ester of Formula VII from the solution; and
(d) converting the isolated boronic ester of Formula VII back into the boronic acid of Formula IA.

10. The process of claim 9, wherein $R^1$ is 2-(6-phenyl)pyridinyl and $R^2$ is (1R)-1-hydroxyethyl.

11. The process of claim 9, wherein $R^1$ is 2-pyrazinyl and $R^2$ is benzyl.

12. A process for preparing a boronic acid of Formula IA

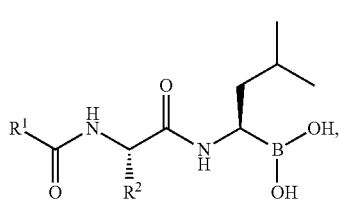

IA wherein
$R^1$ is 2-(6-phenyl)pyridinyl and $R^2$ is (1R)-1-hydroxyethyl, or $R^1$ is 2-pyrazinyl and $R^2$ is benzyl;
comprising the steps of:
(a) preparing a boronic ester of Formula V

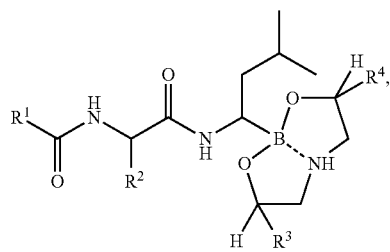

V wherein
$R^1$ is 2-(6-phenyl)pyridinyl, $R^2$ is (1R)-1-hydroxyethyl, and $R^3$ and $R^4$ are H;

$R^1$ is 2-(6-phenyl)pyridinyl, $R^2$ is (1R)-1-hydroxyethyl, and $R^3$ and $R^4$ are methyl;

or $R^1$ is 2-pyrazinyl, $R^2$ is benzyl, and $R^3$ and $R^4$ are H;

(b) crystallizing a boronic ester of Formula I from a solution of the boronic ester of Formula V

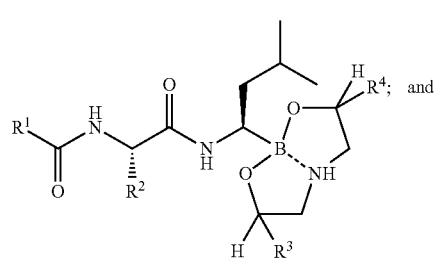

I (c) converting the boronic ester of Formula I into the boronic acid of Formula IA.

13. The process of claim 12, wherein $R^1$ is 2-(6-phenyl)pyridinyl, $R^2$ is (1R)-1-hydroxyethyl, and $R^3$ and $R^4$ are H.

14. The process of claim 12, wherein $R^1$ is 2-(6-phenyl)pyridinyl, $R^2$ is (1R)-1-hydroxyethyl, and $R^3$ and $R^4$ are methyl.

15. The process of claim 12, wherein $R^1$ is 2-pyrazinyl, $R^2$ is benzyl, and $R^3$ and $R^4$ are H.

* * * * *